US011608308B2

(12) United States Patent
Verdin et al.

(10) Patent No.: US 11,608,308 B2
(45) Date of Patent: Mar. 21, 2023

(54) MEDIUM CHAIN FATTY ACID ESTERS OF BETA-HYDROXYBUTYRATE AND BUTANEDIOL AND COMPOSITIONS AND METHODS FOR USING SAME

(71) Applicants: The J. David Gladstone Institutes, San Francisco, CA (US); The Regents of the University of California, Oakland, CA (US); Ithaca College, Ithaca, NY (US)

(72) Inventors: Eric Verdin, Mill Valley, CA (US); Scott Michael Ulrich, Brooktondale, NY (US); John C. Newman, San Francisco, CA (US)

(73) Assignees: The J. David Gladstone Institutes, San Francisco, CA (US); The Regents of The University Of California, Oakland, CA (US); Ithaca College, Ithaca, NY (US)

(*) Notice: Subject to any disclaimer, the term of this patent is extended or adjusted under 35 U.S.C. 154(b) by 0 days.

(21) Appl. No.: 17/110,236

(22) Filed: Dec. 2, 2020

(65) Prior Publication Data
US 2021/0171432 A1 Jun. 10, 2021

Related U.S. Application Data

(63) Continuation of application No. 16/306,524, filed as application No. PCT/US2017/035826 on Jun. 2, 2017, now Pat. No. 10,889,538.

(60) Provisional application No. 62/346,975, filed on Jun. 7, 2016.

(51) Int. Cl.
C07C 69/34 (2006.01)
A61P 25/28 (2006.01)
G02B 1/04 (2006.01)
A61K 31/23 (2006.01)
A23L 33/12 (2016.01)
A61P 9/10 (2006.01)
A61P 13/12 (2006.01)
A61P 25/08 (2006.01)
A61P 25/16 (2006.01)
A61P 35/00 (2006.01)

(52) U.S. Cl.
CPC .............. *C07C 69/34* (2013.01); *A23L 33/12* (2016.08); *A61K 31/23* (2013.01); *A61P 9/10* (2018.01); *A61P 13/12* (2018.01); *A61P 25/08* (2018.01); *A61P 25/16* (2018.01); *A61P 25/28* (2018.01); *A61P 35/00* (2018.01); *G02B 1/04* (2013.01); *A23V 2002/00* (2013.01); *A23V 2200/322* (2013.01); *A23V 2250/54* (2013.01)

(58) Field of Classification Search
CPC .................................................. C07C 69/34
See application file for complete search history.

(56) References Cited

U.S. PATENT DOCUMENTS

| | | |
|---|---|---|
| 4,263,216 A | 4/1981 | Volpenhein |
| 5,008,126 A | 4/1991 | Klemann et al. |
| 5,126,373 A | 6/1992 | Brunengraber et al. |
| 5,413,922 A | 5/1995 | Matsuyama et al. |
| 5,474,775 A | 12/1995 | Traitler et al. |
| 6,287,591 B1 | 9/2001 | Semple et al. |
| 8,642,654 B2 | 2/2014 | Clarke et al. |
| 9,138,420 B2 | 9/2015 | D'agostino et al. |
| 10,245,242 B1 | 4/2019 | Millet |
| 10,562,839 B2 | 2/2020 | Verdin et al. |
| 10,647,658 B2 | 5/2020 | Verdin et al. |
| 10,889,538 B2 | 1/2021 | Verdin et al. |
| 2006/0046286 A1 | 3/2006 | Watanabe et al. |
| 2007/0078279 A1 | 4/2007 | Mettler |
| 2008/0009467 A1 | 1/2008 | Henderson |
| 2013/0041048 A1 | 2/2013 | Chen et al. |
| 2014/0194509 A1 | 7/2014 | Clarke et al. |
| 2014/0308719 A1 | 10/2014 | Clarke et al. |
| 2015/0085217 A1 | 3/2015 | Nanjo et al. |
| 2016/0108442 A1 | 4/2016 | Adelstein et al. |
| 2019/0248730 A1 | 8/2019 | Verdin et al. |
| 2019/0262415 A1 | 8/2019 | King et al. |
| 2019/0359551 A1 | 11/2019 | Verdin et al. |
| 2019/0382333 A1 | 12/2019 | Verdin et al. |
| 2020/0140371 A1 | 5/2020 | Verdin et al. |
| 2021/0094900 A1 | 4/2021 | Scott |

FOREIGN PATENT DOCUMENTS

| | | |
|---|---|---|
| AU | 3251000 A | 11/2000 |
| CN | 101426763 A | 5/2009 |
| CN | 105592888 A | 5/2016 |
| DE | 19703471 A1 | 8/1998 |
| EP | 0054435 A1 | 6/1982 |
| EP | 0316993 A1 | 5/1989 |
| EP | 0384189 A2 | 8/1990 |
| JP | S57131747 A | 8/1982 |
| JP | H01160917 A | 6/1989 |
| JP | H02219598 A | 9/1990 |
| JP | H06179642 A | 6/1994 |
| JP | 2009173677 A | 8/2009 |
| JP | 2012500264 A | 1/2012 |
| JP | 2013520454 A | 6/2013 |

(Continued)

OTHER PUBLICATIONS

U.S. Office Action dated Feb. 19, 2020 issued in U.S. Appl. No. 16/306,524.

(Continued)

*Primary Examiner* — Kamal A Saeed
(74) *Attorney, Agent, or Firm* — Tom Hunter; Weaver Austin Villeneuve & Sampson LLP

(57) ABSTRACT

Aspects of the present disclosure include fatty acid β-hydroxyester compounds (e.g., fatty acid esters of β-hydroxybutyrate), fatty acid esters of butanediol, and pharmaceutically acceptable salts thereof. Also provided are pharmaceutical compositions having one or more fatty acid β-hydroxyester compounds and/or one or more fatty acid esters of butanediol. Methods for treating a subject by administering one or more esters to the subject are also provided. Kits containing one or more of the subject esters are also described.

28 Claims, 52 Drawing Sheets

(56) References Cited

FOREIGN PATENT DOCUMENTS

| WO | WO 2007/095262 A2 | 8/2007 |
|---|---|---|
| WO | WO-2010021766 A1 | 2/2010 |
| WO | WO-2010120300 A1 | 10/2010 |
| WO | WO-2011101171 A1 | 8/2011 |
| WO | WO-2016123229 A1 | 8/2016 |
| WO | WO-2017011294 A1 | 1/2017 |
| WO | WO 2017/213999 A1 | 12/2017 |
| WO | WO 2019/018683 A1 | 1/2019 |
| WO | WO-2019147503 A1 | 8/2019 |

OTHER PUBLICATIONS

U.S. Notice of Allowance dated Sep. 3, 2020 issued in U.S. Appl. No. 16/306,524.
U.S. Notice of Allowance dated Oct. 3, 2019 issued in U.S. Appl. No. 16/525,437.
U.S. Office Action dated Sep. 13, 2019 issued in U.S. Appl. No. 16/528,524.
U.S. Final Office Action dated Feb. 4, 2020 issued in U.S. Appl. No. 16/528,524.
U.S. Notice of Allowance dated Mar. 6, 2020 issued in U.S. Appl. No. 16/528,524.
PCT International Search Report and Written Opinion dated Nov. 1, 2018, issued in PCT/US18/42948.
PCT International Preliminary Report on Patentability and Written Opinion dated Jan. 21, 2020, issued in PCT/US18/42948.
PCT International Search Report and Written Opinion dated Oct. 16, 2017, issued in PCT/US17/35826.
PCT International Preliminary Report on Patentability and Written Opinion dated Dec. 11, 2018, issued in PCT/US17/35826.
Australian Office Action dated Nov. 19, 2020 issued in AU 2017278099.
EP Extended Search Report dated Feb. 6, 2020 issued in EP 17810768.6.
EP Office Action dated Jan. 20, 2021 issued in EP 17810768.6.
Mexican Office Action dated Sep. 3, 2020 issued in MX/a/2018/015302.
Russian Office Action dated Oct. 14, 2020 issued in RU2018143895.
Singapore Office Action (with Search Report and Written Opinion) dated Feb. 13, 2020, issued in SG 11201810765P.
Brownlow, et al. (2013) "Ketogenic Diet Improves Motor Performance but Not Cognition in Two Mouse Models of Alzheimer's Pathology" *PLoS One*, 8(9): e75713 (10 pages).
Cipollone, et al. (2000) "Formation of micelles and liposomes from carnitine amphiphiles" *European Journal of Medicinal Chemistry*, 35(10): 903-911.
Database Registry (Nov. 16, 1984), Abstract No. 50343-39-0, 1 page.
Hashim, et al. (2014) "Ketone body therapy: from the ketogenic diet to the oral administration of ketone ester" *Journal of Lipid Research*, 55(9): 1818-1826 (9 pages).
Henderson (2008) "Ketone bodies as a therapeutic for Alzheimer's disease" *J. Am. Soc. Exp. Neurotherapeutics* 5(3): 470-480.
Jones, et al. (1973) "Potential Oviposition Inducers for Corn Earworm" *Annals of the Entomological Society of America*, 66(5): 921-925.
Newman and Verdin (2017) "β-Hydroxybutyrate: A Signaling Metabolite" *Annual Review of Nutrition* 37:51-76.
PubChem CID 124560026 (2017) "Compound Summary—[(3S)-3-Hydroxybutyl] (3S)-3-hydroxybutanoate", create date: Apr. 10, 2017, 11 pages; Downloaded from URL: https://pubchem.ncbi.nlm.nih.gov/compound/124560026.
PubChem CID 249225 (2005) "Compound Summary—Propane-1,3-diyl dipentanoate", create date: Mar. 26, 2005, 9 pages; Downloaded from URL: https://pubchem.ncbi.nlm.nih.gov/compound/249225.
Rijpstra, et al. (2007) "Structural Identification of the [beta]-Hydroxy Fatty Acid-Based Diester Preen Gland Waxes of Shorebirds" *Journal of Natural Products*, 70(11): 1804-1807.
Stano, et al. (2004) "Novel Camptothecin Anologue (Gimatecan)-Containing Liposomes Prepared by the Ethanol Injection Method" *Journal of Liposome Research*, 14(1-2): 87-109 [XP008059476].
Yang, et al. (2016) "Lipidation of Cysteine or Cysteine-Containing Peptide Using the Thiol-Ene Reaction (CLipPA)" *European Journal of Organic Chemistry*, 2608-2616 (9 pages).
Abraham, et al. (1998) "Novel glycine containing glucolipids from the alkane using bacterium Alcanivorax borkumensis" Biochimica et Biophysica Acta, 1393(1): 57-62.
AU office action dated Nov. 24, 2021, in application No. AU2018304380.
Budin, et al. (2018) "Efficient synthesis of the ketone body ester (R)-3-hydroxybutyryl-(R)-3-hydroxybutyrate and its (S,S) enantiomer" Bioorganic Chemistry, 80: 560-564.
Chinese Office Action dated Jul. 7, 2021 issued CN 201780041428.2.
Dzulkefly, et al. (2007) "Chemical Modification of Sago Starch by Solventless Esterification with Fatty Acid Chlorides" The Malaysian Journal of Analytical Sciences 11(2): 395-399.
EP Extended Search Report dated Mar. 17, 2021 issued in EP 18835222.3.
Hofer, et al. (1985) "Reactivity of carbonyl compounds with ketenes in the presence of titanium or zirconium alkoxides" Helvetica Chimica Acta, 68(4): 969-974.
International Preliminary Report on Patentability and Written Opinion dated Jul. 28, 2020, issued in PCT/US2019/014345.
International Search Report and Written Opinion dated Apr. 10, 2019, issued in PCT/US2019/014345.
JP Office Action dated Apr. 26, 2021 issued in JP 2018-564979.
KR Office Action dated Nov. 2, 2021 issued in KR 10-2019-7000530.
Menhour, et al. (2015) "A stereocontrolled synthesis of the hydrophobic moiety of rhamnolipids" Tetrahedron Letters, 56(9): 1159-1161.
Mohrig, et al. (2007) "Novel Syn Intramolecular Pathway in Base-Catalyzed 1,2-Elimination Reactions of β-Acetoxy Esters" Journal of Organic Chemistry, 72(3): 793-798.
Ohlinger, et al. (2003) "Improved processing stability in the hydrogenation ofdimethyl maleate to y-butyrolactone, 1,4-butanediol and tetrahydrofuran" Chemical Engineering Science 58: 1453-61.
Russian Second Office Action dated Mar. 11, 2021 issued in RU2018143895.
Shimazu, et al. (2013) "Suppression of Oxidative Stress by—Hydroxy butyrate, an Endogenous Histone Deacetylase Inhibitor" Science, 339(6116):211-214 (NIH Public Access Author Manuscript—9 pages) DOI: 10.1126/science. 1227166; Retrieved from the Internet: URL:https://www.ncbi.nlm.nih.gov/pmc/articles/PMC3735349/pdf/nihms486017.pdf.
Sleiman, et al. (2016) "Exercise promotes the expression of brain derived neurotrophic factor (BDIMF) through the action of the ketone body phydroxy butyrate" eLIFE, 5:015092 (21 pages) DOI:10.7554/eLife.15092.
Studenikin, et al. (2004) "Ketogenic diet in epileptic children" Academic research paper on clinical medicine, 3(1): 47-51 [English Abstract].
Zerkowski, et al. (2008) "Structured Estolides: Control of Length and Sequence" Journal of the American Oil Chemists' Society, 85(3): 277-284.
CN Office Action dated May 18, 2022, in Application No. CN201780041428 with English translation.
EP Office Action dated May 27, 2022, in Application No. EP17810768.6.
JP Office Action dated Jun. 13, 2022 in Application No. JP20200502652 With English translation.
Mattson, A. et al., "Resolution of Diols with C2-Symmetry by Lipase Catalysed Transesterification", Tetrahedron: Asymmetry, 1993, vol. 4, No. 5, pp. 925-930.
CAS Registry No. 4196-69-4~1445584-56-4.
CAS Registry No. 83549-93-3~132999-82-7.
AU Office action dated Apr. 7, 2022, in Application No. AU2021203726.
IL Office Action dated Jul. 17, 2022 in Application No. IL272173.
KR Office Action dated Jul. 20, 2022 in Application No. KR20197000530 With English translation.

(56) References Cited

OTHER PUBLICATIONS

MX Office Action dated Jun. 21, 2022, in Application No. MX/a/2020/000734 with English translation.
U.S. Non-Final office Action dated Sep. 13, 2022 in U.S. Appl. No. 16/631,374.
U.S. Restriction Requirement dated Apr. 8, 2022 for U.S. Appl. No. 16/631,374.

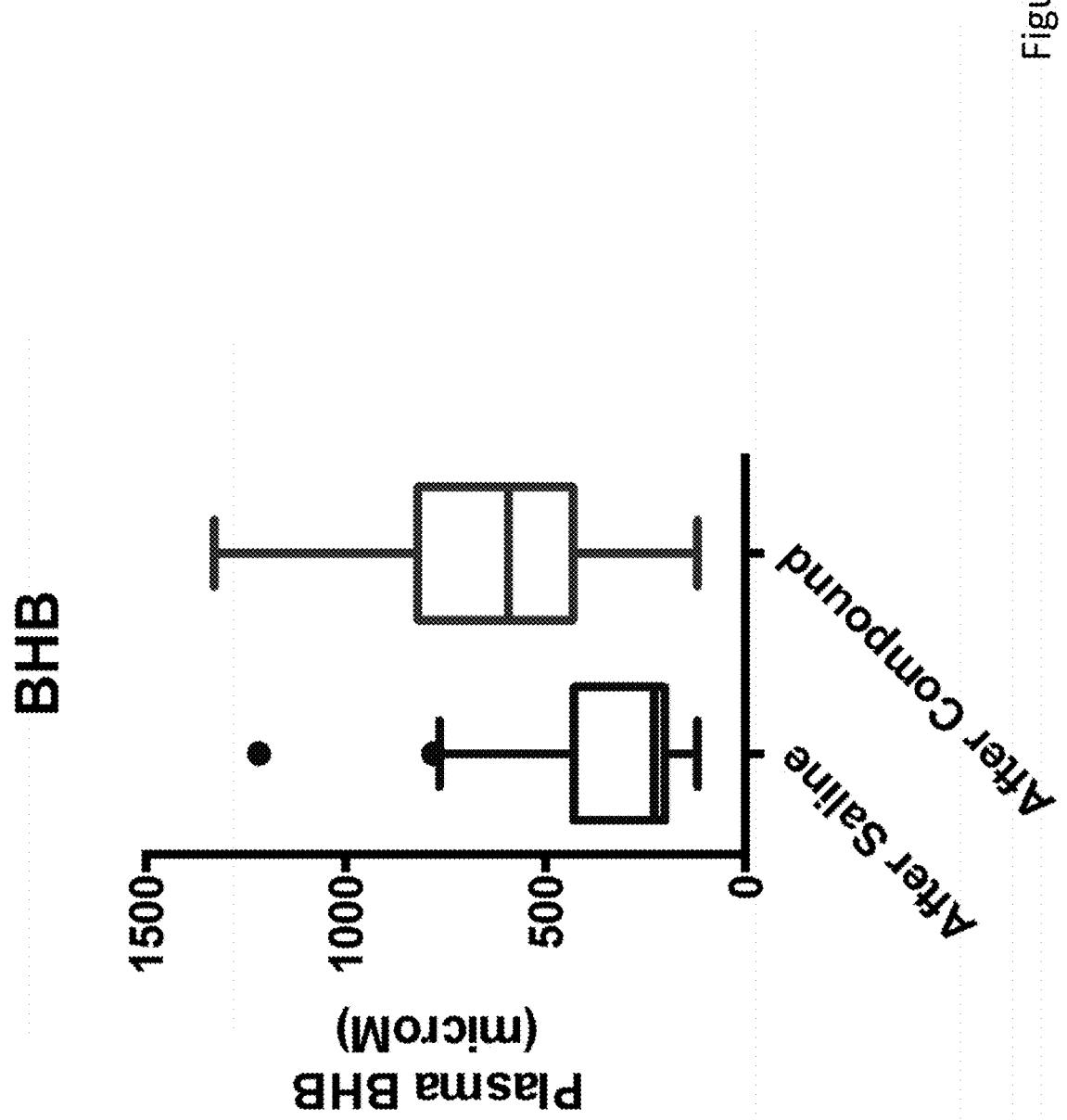

MEDIUM CHAIN FATTY ACID ESTERS OF BETA-HYDROXYBUTYRATE AND BUTANEDIOL AND COMPOSITIONS AND METHODS FOR USING SAME

CROSS-REFERENCE TO RELATED APPLICATIONS

This application is a continuation of U.S. Non-Provisional application Ser. No. 16/306,524, filed on Nov. 30, 2018, which is a U.S. 371 National Phase of PCT/US2017/035826, filed on Jun. 2, 2017, which claims priority to, and benefit of U.S. Provisional Patent Application No. 62/346,975, filed on Jun. 7, 2016, all of which are herein incorporated by reference in their entirety.

STATEMENT REGARDING FEDERALLY SPONSORED RESEARCH

This invention was made with government support under Grant Nos. R24 DK085610 and K08 AG048354 awarded by the National Institutes of Health. The government has certain rights in the invention.

INTRODUCTION

Ketogenic diets and ketone bodies are of interest for the treatment of a variety of human disorders including epilepsy, dementia and diseases of aging. Ketone bodies are small compounds created from fat that serve as a substitute for sugar when the body's energy stores are depleted, such as when fasting or during strenuous exercise. Ketogenic diets stimulate the production of ketone bodies by containing very little sugar or other carbohydrates. The primary ketone bodies in humans are acetoacetate (AcAc) and β-hydroxybutyrate (BHB). Ketogenic diets are used clinically as a therapy for epilepsy, but they are often difficult to adhere to for long periods of time. The extremely high fat content (and low carbohydrate content) can make foods of a ketogenic diet unpalatable, and sometimes cause gastrointestinal problems, kidney stones, high cholesterol and other side effects.

BHB is a metabolic intermediate that is a currency for generating cellular energy, but also has several signaling functions separate from energy production. Either or both of the energy and signaling functions may be important for BHB's effects on human disease. During times of scarce glucose, for example during fasting or strenuous exercise, BHB is the currency by which energy stored in adipose tissue is turned into fuel that can be used by cells throughout the body to sustain their functions. Fat mobilized from adipose tissue is transported to the liver and converted into BHB. BHB circulates in the blood to all tissue. After being absorbed into a cell, BHB is broken down in the mitochondria to generate acetyl-CoA that is further metabolized into ATP. This is the canonical "energy currency" function of BHB.

In addition, BHB may have several signaling functions. Most of these are independent of its function as an energy currency, in that they are actions of the BHB molecule itself, and are not generally secondary effects of its metabolism into acetyl-CoA and ATP. Signaling functions may include: 1) inhibition of class I and IIa histone deacetylases, with resulting changes in histone modifications and gene expression, as well as changes in acetylation state and activity of non-histone proteins; 2) metabolism into acetyl-CoA results in increased cellular production of acetyl-coA to serve as substrate for acetyltransferase enzymes, resulting in similar changes in histone and non-histone protein acetylation as deacetylase inhibition; 3) covalent attachment to histones and possibly other proteins in the form of lysine-β-hydroxybutyrylation, which may have similar effects as lysine-acetylation; 4) binding and activation of hydroxycarboxylic acid receptor 2 (HCAR2) receptor with resultant alterations in adipose tissue metabolism; 5) binding and inhibition of free fatty acid receptor 3 (FFAR3) receptor with resultant changes in sympathetic nervous system activation and whole-body metabolic rate; and 6) inhibition of the NOD-like receptor 3 (NLRP3) inflammasome.

SUMMARY

Aspects of the present disclosure include fatty acid β-hydroxyester compounds (e.g., fatty acid esters of β-hydroxybutyrate), fatty acid esters of butanediol, and pharmaceutically acceptable salts thereof. Also provided are pharmaceutical compositions having one or more fatty acid β-hydroxyester compounds and/or one or more fatty acid esters of butanediol. Methods for treating a subject by administering one or more esters to the subject are also provided. Kits containing one or more of the subject esters are also described.

BRIEF DESCRIPTION OF THE DRAWINGS

FIG. 6a depicts plasma concentration over 6 hours after injection of C6 and C8 esters of β-hydroxybutyrate. FIG. 6b depicts plasma concentration over 6 hours after injection of C6 and C8 esters of butanediol. FIG. 6c depicts plasma concentration over 4 hours after injection of C6 and C8 esters of β-hydroxybutyrate.

(FIG. 7a) 23-hour EEG recorded 2 days after starting KD shows ~30% spike reduction compared to prior baseline on control diet. Overnight fast shows no change. (FIG. 7b) Hourly spike totals during 23-hour EEG recordings. (FIG. 7c) Spike reductions in individual mice, normalized to each mouse's baseline recording (filled circles, $P<0.05$; bar=median). (FIG. 7d) Movement was similar in all diet conditions, as was (FIG. 7e) overall normalized gamma activity. (FIG. 7f) Best-fit linear regression lines with 95% CI for scatterplots of per-minute spikes and movement. APPJ20 normally have lower spikes with higher exploratory movement; on KD spikes are lower at all movement levels. (FIG. 7g) Best-fit linear regression lines with 95% CI for scatterplots of per-minute normalized gamma activity and movement showing no change in the rate of induction of gamma activity by movement on KD. (FIG. 7h) overall mean gamma power is unchanged on KD. P values via T-test for two-way comparisons and ANOVA with Tukey's correction for multiple comparisons. N=9-12 mice per condition; data for A, B, D, E show N=7 that completed all conditions with high-quality data.

(FIG. 8a) Experimental timeline. (FIG. 8b) In seven 50-minute EEGs, APPJ20 on KD had ~40% reduced spikes compared to mice on control diet. (FIG. 8c) Mean spikes/min across the 50 min recording period; spikes for mice on control diet rise as exploratory activity wanes late in recordings. (FIG. 8d) Best-fit linear regression lines with 95% CI for scatterplots of per-minute spikes and movement shows that on KD spikes are lower at all movement levels. (FIG. 8e) Total movement (beam breaks) during post-habituation open fields on Day 53 and 72 showing that exploration is similar between APP on KD and NTG control. (FIGS. 8f-h) total movement (FIG. 8O, rearings (FIG. 8g), and center movements (FIG. 8h) are all similar between APP on KD and NTG control, showing successful habituation. P values via T-test for two-way comparisons and ANOVA with Tukey's correction for multiple comparisons. N=4-6 per group.

(FIG. 9a) Change in body weights for APPJ20 and NTG mice on either KD or control diet, started at 2 months of age. (FIG. 9b) Plasma BHB levels are the mean of six morning measurements taken about every two weeks from the start of the study. (FIGS. 9c, 9d) Survival curves for APPJ20 males and females, respectively, on KD vs control diet. There were no deaths among NTG mice. (FIGS. 9e-9h) Morris water maze performed three months after start of diets. Probe trials were done 24 hours after the final hidden-platform training; reverse training began 24 hours after initial probe trial. APP mice on KD showed improved learning in both initial and reverse training (FIGS. 9e, 9g) but no difference in probe trials (FIGS. 9f, 9h). P values via T-test for two-way comparisons and ANOVA with Tukey's correction for multiple comparisons. N=21-26 per genotype-diet group at start of study; N=11-14 per group for water maze.

FIGS. 10a-10f demonstrate that compounds described herein that are metabolized to BHB immediately reduce epileptiform spikes. (FIG. 10a) Schematic of example ketogenic compounds having a medium-chain fatty acid ester-linked to BHB. (FIGS. 10b-10f) Group of mice was injected with both C6-BHB and normal saline on different days, with EEGs recorded before and after each injection. (FIG. 10b) Injection of C6-BHB increased blood BHB levels, measured approximately 70-80 minutes after injection (following EEG). (FIG. 10c) Injection of C6-BHB reduces spikes compared to both pre-injection baselines and injection of saline. (FIG. 10d) Plot of average spikes over the 50-minute EEG recording shows consistent reduction after C6-BHB injection, similar to KD. (FIG. 10e) Analysis of spike reduction after C6-BHB, compared to after saline, at the individual mouse level shows significant reductions for most mice (filled circles, $P<0.05$; bar=median). (FIG. 10f) Difference in spikes between C6-BHB and saline injection was most pronounced when mice were at rest (and gamma activity is lowest), similar to KD. P values via T-test for two-way comparisons and ANOVA with Tukey's correction for multiple comparisons. N=22, analysis limited to 17 mice that completed all conditions with high-quality data.

DEFINITIONS

Figure 1A:
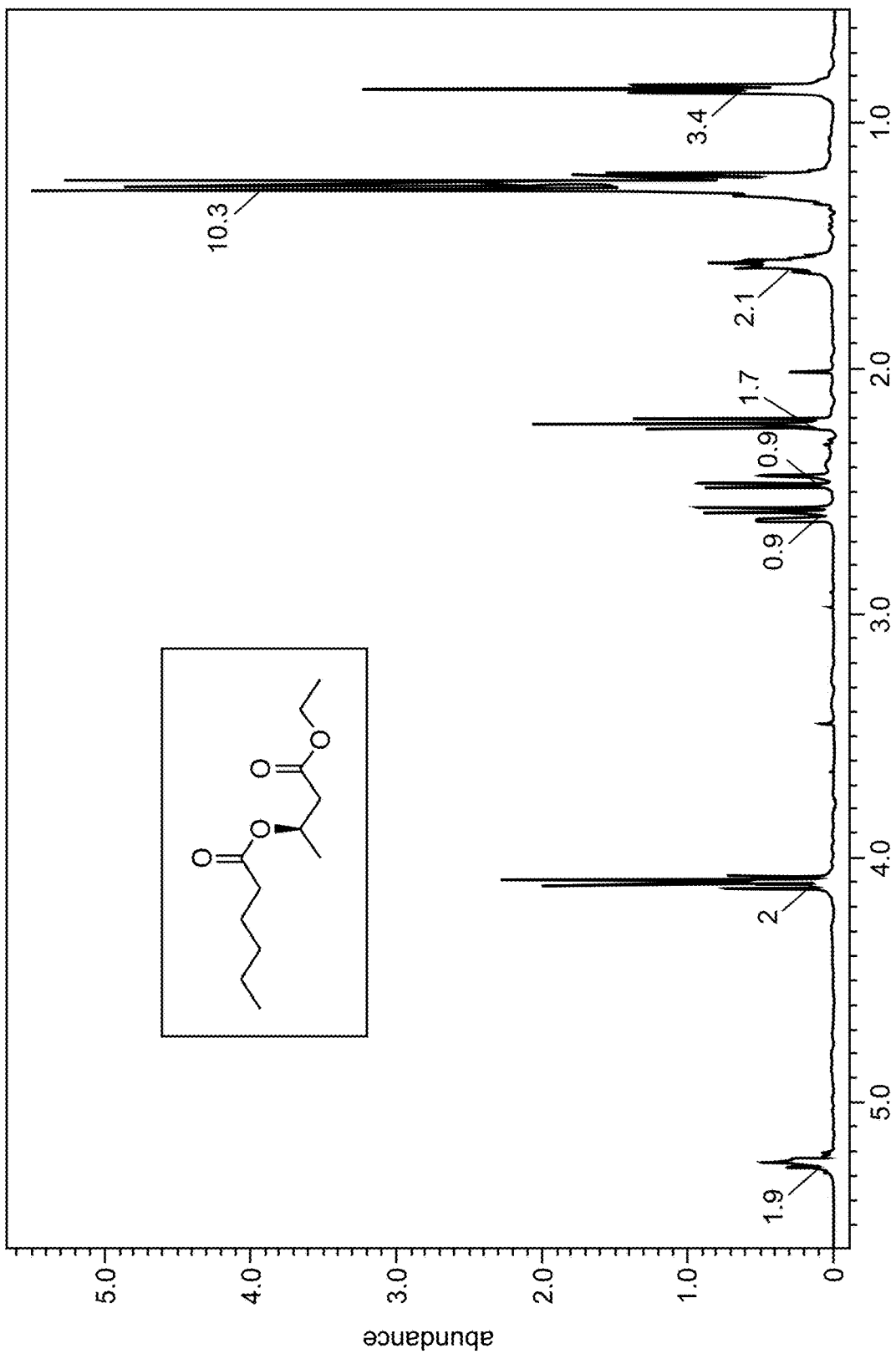
FIGS. 1a and 1b depict the $^1$H-NMR and GC-MS, respectively, of a C6-substituted ester of β-hydroxybutyrate according to certain embodiments.

As used herein, the terms "treatment," "treating," and the like, refer to obtaining a desired pharmacologic and/or physiologic effect. The effect may be prophylactic in terms of completely or partially preventing a condition, disease, pathological process or symptom thereof and/or may be therapeutic in terms of a partial or complete cure for a condition, disease, pathological process and/or adverse effect attributable to the condition, disease or pathological process. "Treatment," as used herein, includes, e.g., any treatment of a condition, disease or pathological process in a mammal, particularly in a human, and includes: (a) preventing the condition, disease or pathological process from occurring in a subject which may be predisposed to the condition, disease or pathological process but has not yet been diagnosed as having it; (b) inhibiting the condition or disease, i.e., arresting its development; and (c) relieving the condition, disease, or pathological process i.e., causing regression of the condition, disease or pathological process.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a compound that, when administered to a mammal or other subject for treating a disease, is sufficient to effect such treatment for the disease. The "therapeutically effective amount" will vary depending on the compound or the cell, the disease and its severity and the age, weight, etc., of the subject to be treated.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Active agent" refers a chemical substance or compound that exerts a pharmacological action and is capable of treating, preventing or ameliorating one or more conditions/maladies (e.g., Alzheimer's disease) as described herein. Examples of active agents of interest include fatty acid β-hydroxyester compounds (e.g., fatty acid esters of β-hydroxybutyrate) and fatty acid esters of butanediol.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent.

DEFINITION OF SELECT CHEMICAL TERMINOLOGY

The nomenclature of certain compounds or substituents are used in their conventional sense, such as described in chemistry literature including but not limited to Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene ($—CH_2—$), ethylene ($—CH_2CH_2—$), the propylene isomers (e.g., $—CH_2CH_2CH_2—$ and $—CH(CH_3)CH_2—$) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)$R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —C(O)N$R^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —O$R^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)O$R^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenylnapthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —N$R^{37}R^{38}$—, =N—N=, —N=N—, —N=N—N$R^{39}R^{40}$, —P$R^{41}$—, —P(O)$_2$—, —PO$R^{42}$—, —O—P(O)$_2$—, —S—O—, —S—(O)—, —SO$_2$—, —Sn$R^{43}R^{44}$— and the like, $R^{38}$, $R^{39}$, $R^{40}$, $R^{41}$, $R^{42}$, $R^{43}$ and $R^{44}$ where $R^{37}$, are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, O-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, O-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O)$_2$O$^-$, —OS(O)$_2$R$^{60}$, —P(O)(O$^-$)$_2$, —P(O) (OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C (O)O$^-$—, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. In certain embodiments, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O) OR$^{60}$, —C(O)NR$^{60}$R$^{61}$, —C(O)O$^-$, —NR$^{62}$C(O)NR$^{60}$R$^{61}$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O), —OP(O)(OR$^{60}$)(OR$^{61}$), —C(O)R$^{60}$, —C(O)OR$^{60}$, —C(O) NR$^{60}$R$^{61}$, —C(O)O$^-$. In certain embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(O R$^{60}$) (OR$^{61}$), —C(O)R$^{60}$, —C(O)OR$^{60}$, —C(O)O$^-$, where R$^{60}$, R$^{61}$ and R$^{62}$ are as defined above. For example, a substituted group may bear a methylenedioxy substituent or one, two, or three substituents selected from a halogen atom, a (1-4C) alkyl group and a (1-4C)alkoxy group.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

DETAILED DESCRIPTION

The present disclosure provides fatty acid β-hydroxyester compounds (e.g., fatty acid esters of β-hydroxybutyrate), fatty acid esters of butanediol, and pharmaceutically acceptable salts thereof. Also provided are pharmaceutical compositions having one or more fatty acid β-hydroxyester compounds and/or one or more fatty acid esters of butanediol.

The present disclosure further provides methods for treating a subject by administering one or more fatty acid β-hydroxyester compounds and/or one or more esters of butanediol to the subject. In some embodiments, methods include treating Alzheimer's disease in a subject diagnosed as having Alzheimer's disease by administering to the subject one or more fatty acid β-hydroxyester compounds described herein and/or one or more esters of butanediol described herein. In some instances, the amount of the one or more of the fatty acid β-hydroxyester compounds and/or the one or more esters of butanediol administered to the subject is sufficient to reduce epileptiform activity in the subject. In certain instances, the amount of the one or more fatty acid β-hydroxyester compounds and/or the one or more esters of butanediol administered to the subject is sufficient to increase cognition in the subject.

The present disclosure further provides methods for treating one or more of epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, Niemann-Pick Type C disease, age-related macular degeneration, gout, atherosclerosis, rheumatoid arthritis and multiple sclerosis by administering one or more of the fatty acid β-hydroxyester compounds described herein and/or one or more of the esters of butanediol described herein to the subject.

The present disclosure also provides compounds, the administration of which provide for increased ketone body concentration in a subject. The fatty acid β-hydroxyester compounds (e.g., fatty acid esters of β-hydroxybutyrate) and fatty acid esters of butanediol as described herein release, via ester hydrolysis, β-hydroxybutyrate or butanediol which increase ketone body concentration in the subject and a supplemental source of medium chain fatty acids that provide for sustained ketone body production by the subject. In some embodiments, the present disclosure provides fatty acid esters of β-hydroxybutyrate which hydrolyze, after administration, to β-hydroxybutyrate and medium chain fatty acids. In these embodiments, the release of β-hydroxybutyrate provides for an increase in ketone body concentration in the subject and the hydrolyzed medium chain fatty acids provide a substrate for sustained physiological production of ketone bodies. In other embodiments, the present disclosure provides fatty acid esters of butanediol which hydrolyze after administration to butanediol and medium chain fatty acids. In these embodiments, the release of butanediol provides for an increase in ketone body production in the subject and the hydrolyzed medium chain fatty acids provide an additional substrate for sustained physiological production of ketone bodies.

Fatty Acid β-Hydroxyester Compounds and Fatty Acid Esters of Butanediol

Fatty acid β-hydroxyester compounds and fatty acid esters of butanediol suitable for practicing the subject methods (described in greater detail below) include a compound of Formulae I and II, as described below.

Compounds of Formulae I and II

The compositions of the present disclosure include compounds of formulae I and II, shown below. Pharmaceutical compositions and methods of the present disclosure also contemplate compounds of formulae I and II.

In one of its composition aspects, the present embodiments provide a compound of formula I:

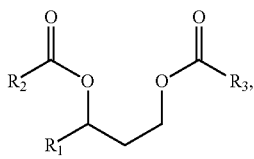

(I)

wherein
$R_1$ is selected from hydrogen, alkyl and substituted alkyl; and
$R_2$ and $R_3$ are independently unsubstituted or substituted alkyl;
and salts, solvates or hydrates thereof.

In formula I, $R_1$ is selected from hydrogen, alkyl and substituted alkyl. In certain instances, $R_1$ is hydrogen. In other instances, $R^1$ is alkyl. In other instances, $R_1$ is substituted alkyl. In certain instances, $R_1$ is alkyl, such as $C_1$-$C_6$ alkyl, including $C_1$-$C_3$ alkyl. In certain instances, $R_1$ is methyl, ethyl, n-propyl, isopropyl, n-butyl, iso-butyl or t-butyl. In certain instances, $R_1$ is methyl.

In formula I, $R_2$ is selected from alkyl and substituted alkyl. In certain instances, $R_2$ is alkyl. In other instances, $R_2$ is substituted alkyl. In certain instances, $R_2$ is alkyl, such as $C_4$-$C_{30}$ alkyl, including $C_6$-$C_8$ alkyl. In certain instances, $R_2$ is hexyl or octyl ($C_6$ or $C_8$). In certain instances, $R_2$ is hexyl ($C_6$). In certain instances, $R_2$ is octyl ($C_8$).

In formula I, $R_3$ is selected from alkyl and substituted alkyl. In certain instances, $R_3$ is alkyl. In other instances, $R_3$ is substituted alkyl. In certain instances, $R_3$ is alkyl, such as $C_4$-$C_{30}$ alkyl, including $C_6$-$C_8$ alkyl. In certain instances, $R_3$ is hexyl or octyl ($C_6$ or $C_8$). In certain instances, $R_3$ is hexyl ($C_6$). In certain instances, $R_3$ is octyl ($C_8$).

In formula I according to certain embodiments, $R_1$ is methyl and $R_2$ and $R_3$ are independently hexyl. In certain instances, $R_1$ is methyl and $R_2$ and $R_3$ are independently octyl. In other instances, $R_1$ is methyl and $R_2$ is hexyl and $R_3$ octyl. In other instances $R_1$ is methyl and $R_2$ is octyl and $R_3$ is hexyl.

In certain embodiments, fatty acid esters of 1,3-butanediol of interest are enantiomerically pure (<95% ee). 1,3-butanediol is metabolized to BHB by alcohol dehydrogenase and aldehyde dehydrogenase, both of which act on the 1' hydroxyl group and are not specific to the chirality of the 3' group. Therefore, R-1,3-butanediol is metabolized to R—BHB, and S-1,3-butanediol is metabolized to S-BHB by these enzymes.

The compounds described in this application include 1,3-butanediol ester-linked to one or more fatty acids or BHB ester-linked to one or more fatty acids. The compounds are chiral, because the 1,3-butanediol and BHB moieties are chiral. However, it is important to note that the fatty acid moiety can only be metabolized to R—BHB in the body, due to the stereospecificity of beta-hydroxybutyrate dehydrogenase described above. Therefore, a compound that includes S-BHB linked to a fatty acid will ultimately generate one unit of S-BHB but also several units of R—BHB. In certain embodiments, none of the compounds described herein generate exclusively S-BHB when fully metabolized in the body.

In certain embodiments, the differences in metabolism between R—BHB and S-BHB are important for their relative efficacy in treating human diseases. As described above, only R—BHB can be readily metabolized to acetyl-CoA and ATP, fulfilling the "energy currency" function of BHB. If efficacy in treating a disease is based upon this energy function of BHB, then R—BHB will be substantially more effective than S-BHB. However, in some instances the efficacy of BHB in some human diseases may rely upon the signaling functions of BHB, rather than the energy function. Several of the signaling functions of interest may include, but are not limited to, HCAR2 inhibition, inflammasome inhibition and inhibition of deacetylase enzymes. In these embodiments, where S-BHB has a similar molecular effect as R—BHB, then the slower metabolism of S-BHB may provide a longer duration of action in the body.

In another composition aspect, the present embodiments provide a compound of formula Ia:

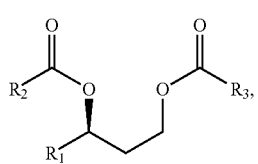

(Ia)

wherein
$R^1$ is selected from hydrogen, alkyl and substituted alkyl; and
$R_2$ and $R_3$ are independently unsubstituted or substituted alkyl;
and salts, solvates or hydrates thereof.

In formula Ia, $R_1$ is selected from hydrogen, alkyl and substituted alkyl. In certain instances, $R_1$ is hydrogen. In other instances, $R^1$ is alkyl. In other instances, $R_1$ is substituted alkyl. In certain instances, $R^1$ is alkyl, such as $C_1$-$C_6$ alkyl, including $C_1$-$C_3$ alkyl. In certain instances, $R_1$ is methyl, ethyl, n-propyl, isopropyl, n-butyl, iso-butyl or t-butyl. In certain instances, $R_1$ is methyl.

In formula Ia, $R_2$ is selected from alkyl and substituted alkyl. In certain instances, $R_2$ is alkyl. In other instances, $R_2$ is substituted alkyl. In certain instances, $R_2$ is alkyl, such as $C_4$-$C_{30}$ alkyl, including $C_6$-$C_8$ alkyl. In certain instances, $R_2$ is hexyl or octyl ($C_6$ or $C_8$). In certain instances, $R_2$ is hexyl ($C_6$). In certain instances, $R_2$ is octyl ($C_8$).

In formula Ia, $R_3$ is selected from alkyl and substituted alkyl. In certain instances, $R_3$ is alkyl. In other instances, $R_3$ is substituted alkyl. In certain instances, $R_3$ is alkyl, such as $C_4$-$C_{30}$ alkyl, including $C_6$-$C_8$ alkyl. In certain instances, $R_3$ is hexyl or octyl ($C_6$ or $C_8$). In certain instances, $R_3$ is hexyl ($C_6$). In certain instances, $R_3$ is octyl ($C_8$).

In formula Ia according to certain embodiments, $R_1$ is methyl and $R_2$ and $R_3$ are independently hexyl. In certain instances, $R_1$ is methyl and $R_2$ and $R_3$ are independently octyl. In other instances, $R_1$ is methyl and $R_2$ is hexyl and $R_3$ octyl. In other instances $R_1$ is methyl and $R_2$ is octyl and $R_3$ is hexyl.

In certain embodiments, fatty acid esters of butanediol of interest include a compound of formula BDE-1a-BDE-1b:

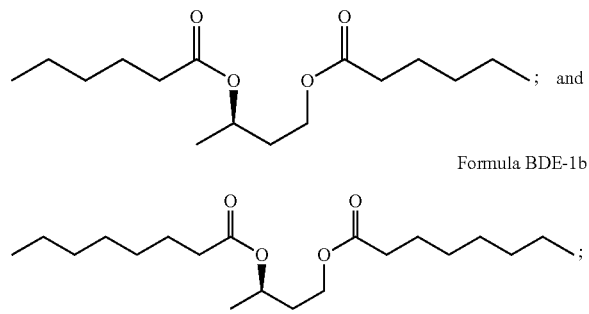

Formula BDE-1a

Formula BDE-1b and salts, solvates or hydrates thereof.

In another composition aspect, the present embodiments provide a compound of formula Ib:

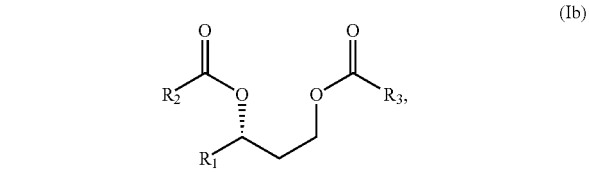

(Ib)

wherein
$R^1$ is selected from hydrogen, alkyl and substituted alkyl; and
$R_2$ and $R_3$ are independently unsubstituted or substituted alkyl.
and salts, solvates or hydrates thereof.

In formula Ib, $R_1$ is selected from hydrogen, alkyl and substituted alkyl. In certain instances, $R_1$ is hydrogen. In other instances, $R^1$ is alkyl. In other instances, $R_1$ is substituted alkyl. In certain instances, $R_1$ is alkyl, such as $C_1$-$C_6$ alkyl, including $C_1$-$C_3$ alkyl. In certain instances, $R_1$ is methyl, ethyl, n-propyl, isopropyl, n-butyl, iso-butyl or t-butyl. In certain instances, $R_1$ is methyl.

In formula Ib, $R_2$ is selected from alkyl and substituted alkyl. In certain instances, $R_2$ is alkyl. In other instances, $R_2$ is substituted alkyl. In certain instances, $R_2$ is alkyl, such as $C_4$-$C_{30}$ alkyl, including $C_6$-$C_8$ alkyl. In certain instances, $R_2$ is hexyl or octyl ($C_6$ or $C_8$). In certain instances, $R_2$ is hexyl ($C_6$). In certain instances, $R_2$ is octyl ($C_8$).

In formula Ib, $R_3$ is selected from alkyl and substituted alkyl. In certain instances, $R_3$ is alkyl. In other instances, $R_3$ is substituted alkyl. In certain instances, $R_3$ is alkyl, such as $C_4$-$C_{30}$ alkyl, including $C_6$-$C_8$ alkyl. In certain instances, $R_3$ is hexyl or octyl ($C_6$ or $C_8$). In certain instances, $R_3$ is hexyl ($C_6$). In certain instances, $R_3$ is octyl ($C_8$).

In formula Ib according to certain embodiments, $R_1$ is methyl and $R_2$ and $R_3$ are independently hexyl. In certain instances, $R_1$ is methyl and $R_2$ and $R_3$ are independently octyl. In other instances, $R_1$ is methyl and $R_2$ is hexyl and $R_3$ octyl. In other instances $R_1$ is methyl and $R_2$ is octyl and $R_3$ is hexyl.

In another composition aspect, the present embodiments provide a compound of formula II:

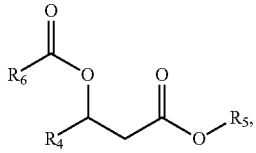

(II)

wherein
$R_4$ is selected from hydrogen, alkyl and substituted alkyl; and
$R_5$ and $R_6$ are independently unsubstituted or substituted alkyl;
and salts, solvates or hydrates thereof.

In formula II, $R_4$ is selected from hydrogen, alkyl and substituted alkyl. In certain instances, $R_4$ is hydrogen. In other instances, $R_4$ is alkyl. In other instances, $R_4$ is substituted alkyl. In certain instances, $R_4$ is alkyl, such as $C_1$-$C_6$ alkyl, including $C_1$-$C_3$ alkyl. In certain instances, $R_4$ is methyl, ethyl, n-propyl, isopropyl, n-butyl, iso-butyl or t-butyl. In certain instances, $R_4$ is methyl.

In formula II, $R_5$ is selected from alkyl and substituted alkyl. In certain instances, $R_5$ is alkyl. In other instances, $R_5$ is substituted alkyl. In certain instances, $R_5$ is alkyl, such as $C_4$-$C_{30}$ alkyl, including $C_6$-$C_8$ alkyl. In certain instances, $R_5$ is hexyl or octyl ($C_6$ or $C_8$). In certain instances, $R_5$ is hexyl ($C_6$). In certain instances, $R_5$ is octyl ($C_8$).

In formula II, $R_6$ is selected from alkyl and substituted alkyl. In certain instances, $R_6$ is alkyl. In other instances, $R_6$ is substituted alkyl. In certain instances, $R_6$ is alkyl, such as $C_4$-$C_{30}$ alkyl, including $C_6$-$C_8$ alkyl. In certain instances, $R^3$ is hexyl or octyl ($C_6$ or $C_8$). In certain instances, $R_6$ is hexyl (C6). In certain instances, $R^3$ is octyl ($C_8$).

In formula II according to certain embodiments, $R_4$ is methyl and $R_5$ and $R_6$ are independently hexyl. In certain instances, $R_4$ is methyl and $R_5$ and $R_6$ are independently octyl. In other instances, $R_4$ is methyl and $R_5$ is hexyl and $R_6$ octyl. In other instances $R_4$ is methyl and $R_5$ is octyl and $R_6$ is hexyl.

In certain embodiments, fatty acid β-hydroxyester compounds of interest are enantiomerically pure (<95% ee). R—BHB is the normal product of human metabolism. This chiral specificity is introduced by the enzyme that catalyzes the final step in BHB synthesis, beta-hydroxybutyrate dehydrogenase. This enzyme reduces the 3' carbonyl group of acetoacetate to the 3' hydroxyl group of BHB. The same enzyme is also required for utilization of BHB, by catalyzing the same reaction in reverse. As a result of the chiral specificity of β-hydroxybutyrate dehydrogenase, only R—BHB is produced by normal metabolism, and only R—BHB can be readily broken down into acetyl-CoA and ATP. Fasting, exercise, caloric restriction, ketogenic diet, and any other state that result in endogenous production of BHB will produce only R—BHB.

S-BHB itself is not a normal product of human metabolism. However, S-BHB-CoA is a transient intermediate in the final round of beta-oxidation of fatty acids. Under normal circumstances it should not persist long enough to leave the mitochondrion or circulate in the blood. Experiments involving infusions of labeled R—BHB, S-BHB, or mixtures into rats or pigs found that S-BHB is mostly converted to R—BHB; the molecular pathway for this is not known, but may be through conversion of S-BHB to acetyl-CoA, and then production of R—BHB from that acetyl-CoA. At least some of the S-BHB is eventually converted to $CO_2$, presumably after being metabolized to acetyl-CoA that is then metabolized in the TCA cycle. S-BHB may be metabolized much more slowly than R—BHB, so that infusion of the same amount of S-BHB may result in higher blood levels of S-BHB for a longer time, than a similar infusion of R—BHB would generate blood levels of R—BHB.

In another composition aspect, the present embodiments provide a compound of formula IIa:

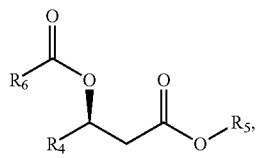
(IIa)

wherein
$R_4$ is selected from hydrogen, alkyl and substituted alkyl; and
$R_5$ and $R_6$ are independently unsubstituted or substituted alkyl;
and salts, solvates or hydrates thereof.

In formula IIa, $R_4$ is selected from hydrogen, alkyl and substituted alkyl. In certain instances, $R_4$ is hydrogen. In other instances, $R_4$ is alkyl. In other instances, $R_4$ is substituted alkyl. In certain instances, $R_4$ is alkyl, such as $C_1$-$C_6$ alkyl, including $C_1$-$C_3$ alkyl. In certain instances, $R_4$ is methyl, ethyl, n-propyl, isopropyl, n-butyl, iso-butyl or t-butyl. In certain instances, $R_4$ is methyl.

In formula IIa, $R_5$ is selected from alkyl and substituted alkyl. In certain instances, $R_5$ is alkyl. In other instances, $R_5$ is substituted alkyl. In certain instances, $R_5$ is alkyl, such as $C_4$-$C_{30}$ alkyl, including $C_6$-$C_8$ alkyl. In certain instances, $R_5$ is hexyl or octyl ($C_6$ or $C_8$). In certain instances, $R_5$ is hexyl ($C_6$). In certain instances, $R_5$ is octyl ($C_8$).

In formula IIa, $R_6$ is selected from alkyl and substituted alkyl. In certain instances, $R_6$ is alkyl. In other instances, $R_6$ is substituted alkyl. In certain instances, $R_6$ is alkyl, such as $C_4$-$C_{30}$ alkyl, including $C_6$-$C_8$ alkyl. In certain instances, $R^3$ is hexyl or octyl ($C_6$ or $C_8$). In certain instances, $R_6$ is hexyl ($C_6$). In certain instances, $R^3$ is octyl ($C_8$).

In formula IIa according to certain embodiments, $R_4$ is methyl and $R_5$ and $R_6$ are independently hexyl. In certain instances, $R_4$ is methyl and $R_5$ and $R_6$ are independently octyl. In other instances, $R_4$ is methyl and $R_5$ is hexyl and $R_6$ octyl. In other instances $R_4$ is methyl and $R_5$ is octyl and $R_6$ is hexyl.

In certain embodiments, fatty acid β-hydroxyester compounds of interest include a β-hydroxybutyrate compound of formula BHE-2a-BHE-2d:

Formula BHE-2a

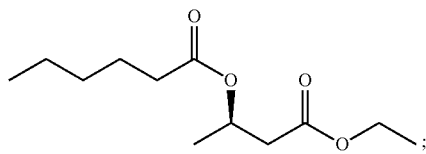

Formula BHE-2b

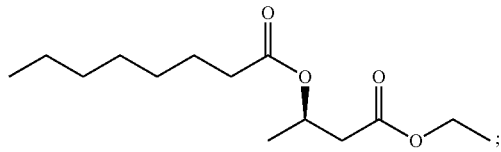

Formula BHE-2c

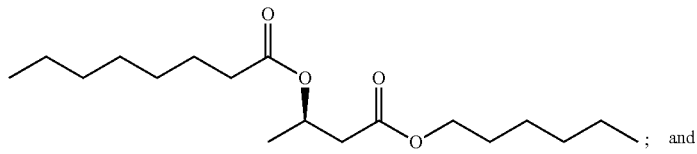
; and

Formula BHE-2d

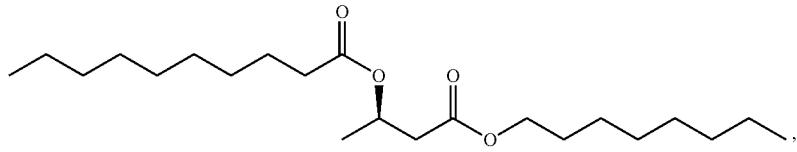
, and salts, solvates or hydrates thereof.

In another composition aspect, the present embodiments provide a compound of formula IIa:

(IIb)
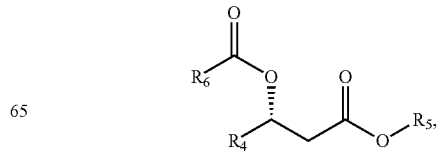

wherein $R_4$ is selected from hydrogen, alkyl and substituted alkyl; and $R_5$ and $R_6$ are independently unsubstituted or substituted alkyl;

and salts, solvates or hydrates thereof.

In formula IIb, $R_4$ is selected from hydrogen, alkyl and substituted alkyl. In certain instances, $R_4$ is hydrogen. In other instances, $R_4$ is alkyl. In other instances, $R_4$ is substituted alkyl. In certain instances, $R_4$ is alkyl, such as $C_1$-$C_6$ alkyl, including $C_1$-$C_3$ alkyl. In certain instances, $R_4$ is methyl, ethyl, n-propyl, isopropyl, n-butyl, iso-butyl or t-butyl. In certain instances, $R_4$ is methyl.

In formula IIb, $R_5$ is selected from alkyl and substituted alkyl. In certain instances, $R_5$ is alkyl. In other instances, $R_5$ is substituted alkyl. In certain instances, $R_5$ is alkyl, such as $C_4$-$C_{30}$ alkyl, including $C_6$-$C_8$ alkyl. In certain instances, $R_5$ is hexyl or octyl ($C_6$ or $C_8$). In certain instances, $R_5$ is hexyl ($C_6$). In certain instances, $R_5$ is octyl ($C_8$).

In formula IIb, $R_6$ is selected from alkyl and substituted alkyl. In certain instances, $R_6$ is alkyl. In other instances, $R_6$ is substituted alkyl. In certain instances, $R_6$ is alkyl, such as $C_4$-$C_{30}$ alkyl, including $C_6$-$C_8$ alkyl. In certain instances, $R^3$ is hexyl or octyl ($C_6$ or $C_8$). In certain instances, $R_6$ is hexyl ($C_6$). In certain instances, $R^3$ is octyl ($C_8$).

In formula IIb according to certain embodiments, $R_4$ is methyl and $R_5$ and $R_6$ are independently hexyl. In certain instances, $R_4$ is methyl and $R_5$ and $R_6$ are independently octyl. In other instances, $R_4$ is methyl and $R_5$ is hexyl and $R_6$ octyl. In other instances $R_4$ is methyl and $R_5$ is octyl and $R_6$ is hexyl.

Formulations, Dosages, and Routes of Administration

Pharmaceutically acceptable carriers preferred for use with active agents (and optionally one or more additional therapeutic agent) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent (and optionally one or more additional therapeutic agent) may also be lyophilized using means well known in the art, for subsequent reconstitution and use according to the invention.

Formulations

The subject fatty acid β-hydroxyester compounds and/or the subject fatty acid esters of butanediol may be administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc. For the purposes of the following description of formulations, "active agent" includes an active agent as described above, e.g., a fatty acid β-hydroxyester compound or a fatty acid ester of butanediol as described herein, and optionally one or more additional therapeutic agents.

In a subject method, an active agent may be administered to the host using any convenient protocol. Thus, an active agent can be incorporated into a variety of formulations for therapeutic administration. For example, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent is formulated as a gel, as a solution, or in some other form suitable for intravaginal administration. In a further exemplary embodiment, an active agent is formulated as a gel, as a solution, or in some other form suitable for rectal (e.g., intrarectal) administration.

In pharmaceutical dosage forms, an active agent may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an active is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent as described herein may be provided and/or administered as a food supplement, e.g., in combination with one or more components of a ketogenic diet. Exemplary ketogenic diets and components thereof are described for example in U.S. Pat. No. 6,207,856, the disclosure of which is incorporated by reference herein.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

Unit dosage forms for intravaginal or intrarectal administration such as syrups, elixirs, gels, and suspensions may be provided wherein each dosage unit, for example, teaspoonful, tablespoonful, tablet, unit gel volume, or suppository, contains a predetermined amount of the composition containing one or more active agents.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 25% (w/w), e.g. about 5% to about 20%, including from 5% to 15%.

An active agent can be administered as an injectable. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration comprises an active agent formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

An active agent will in some embodiments be formulated for rectal delivery. A subject formulation for intrarectal administration comprises an active agent formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfate, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range of an active agent is one which provides up to about 1 g to about 100 g, e.g., from about 1 g to about 90 g, from about 2.5 g to about 80 g, from about 5.0 g to about 70 mg, from about 7.5 g to about 60 g, from about 10 g to about 50 g, from about 12.5 g to about 40 g, from about 15 g to about 30 g, or from 5 g to 20 g of an active agent can be administered in a single dose.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of an active agent is administered. In other embodiments, multiple doses of an active agent are administered. Where multiple doses are administered over a period of time, an active agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

Accordingly the amount of active agent administered to the subject per day may range from 10 grams/day to 500 grams/day, such as from 15 grams/day to 450 grams/day, such as from 25 grams/day to 400 grams/day, such as from 50 grams/day to 300 grams/day and including from 100 grams/day to 200 grams/day.

Where two different active agents are administered, a first active agent and a second active agent can be administered in separate formulations. A first active agent and a second active agent can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

It should be noted that where a particular, method, dosage, dosage regimen, route of administration, etc. described herein would be inappropriate due to the form of a compound of the present disclosure, e.g., due to the presence of a salt form of a compound of the present disclosure, the form of the compound may be selected for the method, dosage, dosage regimen, route of administration, etc. accordingly. For example, where the presence of a salt form of a compound of the present disclosure would be inappropriate (e.g., due to the presence of a detrimental amount of salt in a dosage form), the form of the compound provided for the particular method, dosage, dosage regimen, route of administration, etc., may specifically exclude a salt form of the compound.

Routes of Administration

An active agent is administered to an individual using any available method and route suitable for drug delivery, including in vivo and ex vivo methods, as well as systemic and localized routes of administration.

Conventional and pharmaceutically acceptable routes of administration include oral, intranasal, intramuscular, intratracheal, transdermal, subcutaneous, intradermal, topical application, intravenous, vaginal, nasal, and other parenteral routes of administration. In some embodiments, an active agent is administered orally. In some embodiments, an active agent is administered via an intravaginal route of administration. In other embodiments, an active agent is administered via an intrarectal route of administration. Routes of administration may be combined, if desired, or adjusted depending upon the agent and/or the desired effect. The composition can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent can also be delivered to the subject by enteral administration. Enteral routes of administration include, but are not necessarily limited to, oral and rectal (e.g., using a suppository) delivery.

The term "treatment" as used herein can refer to an amelioration of the symptoms associated with the pathological condition afflicting the host, where amelioration is used in a broad sense to refer to at least a reduction in the magnitude of a parameter, e.g. symptom, associated with the pathological condition being treated, e.g., the presence of abnormal epileptiform spikes. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

The compounds and compositions described herein may be administered to a variety of hosts (wherein the term "host" is used interchangeably herein with the terms "subject" and "patient"). In certain embodiments, the subject is a "mammal" or is "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. Human subjects may be of both genders and at any stage of development (i.e., neonates, infant, juvenile, adolescent, adult), where in certain embodiments the human subject is a juvenile, adolescent or adult. While the present disclosure may be administered to a human subject, it is to be understood that the subject fatty acid β-hydroxyester compounds and fatty acid esters of butanediol may also be administered to animal subjects (that is, in "non-human subjects") such as, but not limited to, birds, mice, rats, dogs, cats, livestock and horses.

Kits, Containers, Devices, Delivery Systems

Kits with unit doses of the active agent, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the subject compositions. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

In some embodiments, the delivery system is a delivery system that provides for injection of a formulation comprising an active agent subcutaneously, intravenously, or intramuscularly. In other embodiments, the delivery system is a vaginal or rectal delivery system.

In some embodiments, an active agent is packaged for oral administration. The present invention provides a packaging unit comprising daily dosage units of an active agent. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a subject delivery system comprises an injection device. Exemplary, non-limiting drug delivery devices include injections devices, such as pen injectors, and needle/syringe devices. Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; the disclosures of each of which are incorporated by reference herein; and the like. The medication delivery pen can be disposable, or reusable and refillable.

The present invention provides a delivery system for vaginal or rectal delivery of an active agent to the vagina or rectum of an individual. The delivery system comprises a device for insertion into the vagina or rectum. In some embodiments, the delivery system comprises an applicator for delivery of a formulation into the vagina or rectum; and a container that contains a formulation comprising an active agent. In these embodiments, the container (e.g., a tube) is adapted for delivering a formulation into the applicator. In other embodiments, the delivery system comprises a device that is inserted into the vagina or rectum, which device includes an active agent. For example, the device is coated with, impregnated with, or otherwise contains a formulation comprising the active agent.

In some embodiments, the vaginal or rectal delivery system is a tampon or tampon-like device that comprises a subject formulation. Drug delivery tampons are known in the art, and any such tampon can be used in conjunction with a subject drug delivery system. Drug delivery tampons are described in, e.g., U.S. Pat. No. 6,086,909, the disclosure of which is incorporated by reference herein. If a tampon or tampon-like device is used, there are numerous methods by which an active agent can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal or rectal ring. Vaginal or rectal rings usually consist of an inert elastomer ring coated by another layer of elastomer containing an active agent to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal or rectal delivery system is a vaginal or rectal sponge. The active agent is incorporated into a silicone matrix which is coated onto a cylindrical drug-free polyurethane sponge, as described in the literature.

Pessaries, tablets, and suppositories are other examples of drug delivery systems which can be used, e.g., in carrying out a method of the present disclosure. These systems have been described extensively in the literature.

Bioadhesive microparticles constitute still another drug delivery system suitable for use in the present invention. This system is a multi-phase liquid or semi-solid preparation which does not seep from the vagina or rectum as do many suppository formulations. The substances cling to the wall of the vagina or rectum and release the drug over a period of time. Many of these systems were designed for nasal use but can be used in the vagina or rectum as well (e.g. U.S. Pat. No. 4,756,907, the disclosure of which is incorporated by reference herein). The system may comprise microspheres with an active agent; and a surfactant for enhancing uptake of the drug. The microparticles have a diameter of 10-100 μm and can be prepared from starch, gelatin, albumin, collagen, or dextran.

Another system is a container comprising a subject formulation (e.g., a tube) that is adapted for use with an applicator. The active agent is incorporated into creams, lotions, foams, paste, ointments, and gels which can be applied to the vagina or rectum using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R. Gennaro, ed., 1995. The choice of suitable carriers will depend on the exact nature of the particular vaginal or rectal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079, the disclosure of which is incorporated by reference herein.

Treatment Methods

The present disclosure also provides methods for treating a subject by administering one or more fatty acid β-hydroxyester compound and/or one or more esters of butanediol to the subject or a pharmaceutically acceptable salt thereof. In some embodiments, methods include administering one or more fatty acid β-hydroxyester compound or pharmaceutically acceptable salt thereof to the subject. In other embodiments, methods include administering one or more esters of butanediol or a pharmaceutically acceptable salt thereof to the subject. In certain embodiments, methods include administering a combination of one or more fatty acid β-hydroxyester compound or a pharmaceutically acceptable salt thereof and one or more esters of butanediol or a pharmaceutically acceptable salt thereof to the subject. Where both a fatty acid β-hydroxyester compound and an esters of butanediol are administered to the subject, in certain instances, the mass ratio of fatty acid β-hydroxyester compound to ester of butanediol ranges from 10:1 to 1:1, such as from 9:1 to 1.5:1, such as from 8:1 to 2:1, such as from 7:1 to 2.5:1, such as from 6:1 to 3:1 and including from 5:1 to 4:1. In other instances the mass ratio of fatty acid β-hydroxyester compound to ester of butanediol ranges from 1:10 to 1:1 such as from 1:9 to 1:1, such as from 1:8 to 1:1.5, such as from 1:7 to 1:2, such as from 1:6 to 1:2.5 and including from 1:5 to 1:3.

In some embodiments, methods include treating one or more of Alzheimer's disease, epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, Niemann-Pick Type C disease, age-related macular degeneration, gout, atherosclerosis, rheumatoid arthritis and multiple sclerosis by administering one or more of the fatty acid β-hydroxyester compounds and/or one or more of the esters of butanediol described herein to a subject.

In certain embodiments, methods include treating Alzheimer's disease by administering to the subject one or more of the fatty acid β-hydroxyester compounds and/or one or more esters of butanediol described herein. In some instances, the amount (as described above) of the one or more fatty acid β-hydroxyester compounds and/or one or more esters of butanediol administered to the subject is sufficient to reduce epileptiform activity in the subject. For example, the subject methods may include administering an amount of the subject fatty acid β-hydroxyester compounds or esters of butanediol sufficient to reduce epileptiform activity by 5% or more, such as 10% or more, such as 15% or more, such as 25% or more, such as 40% or more, such as 50% or more, such as 75% or more, such as 90% or more, such as 95% or more, such as 99% or more and including reducing epileptiform activity by 99.9% or more.

In other instances, the amount of the one or more fatty acid β-hydroxyester compounds and/or one or more esters of butanediol administered to the subject is sufficient to increase cognition in the subject. For example, the subject methods may include administering an amount of the subject fatty acid β-hydroxyester compounds or fatty acid esters of butanediol sufficient to increase cognition in the subject by 5% or more, such as 10% or more, such as 15% or more, such as 25% or more, such as 40% or more, such as 50% or more, such as 75% or more, such as 90% or more, such as 95% or more, such as 99% or more and including increasing cognition in the subject by 99.9% or more.

In yet other instances, the amount of the one or more fatty acid β-hydroxyester compounds and/or one or more esters of butanediol administered to the subject is sufficient to reduce the rate of decline of cognition in the subject. For example, the subject methods may include administering an amount of the subject fatty acid β-hydroxyester compounds or fatty acid esters of butanediol sufficient to decrease the rate of decline of cognition in the subject by 5% or more, such as 10% or more, such as 15% or more, such as 25% or more, such as 40% or more, such as 50% or more, such as 75% or more, such as 90% or more, such as 95% or more, such as 99% or more and including reducing the rate of decline in cognition in the subject by 99.9% or more.

Cognition level in a subject may be assessed by any convenient protocol, including but not limited to the Montreal Cognitive Assessment (MoCA), St. Louis University Mental State Exam (SLUMS), Mini Mental State Exam (MMSE), and, for research purposes, Alzheimer's Disease Assessment Scale, Cognition (ADAS-Cog), as well as assessments including Activities of Daily Living (ADLs) and Instrumental Activities of Daily Living (IADLs).

In certain embodiments, the amount of the one or more fatty acid (3-hydroxyester compounds and/or one or more esters of butanediol administered to the subject is sufficient to improve a subject's daily function such as determined by assessments by Activities of Daily Living (ADLs) and Instrumental Activities of Daily Living (IADLs).

In other embodiments, the amount of the one or more fatty acid (3-hydroxyester compounds and/or one or more esters of butanediol administered to the subject is sufficient to reduce agitated behaviors in the subject. For example, the subject methods may include administering an amount of the subject fatty acid (3-hydroxyester compounds or fatty acid esters of butanediol sufficient to reduce agitated behaviors in the subject by 5% or more, such as 10% or more, such as 15% or more, such as 25% or more, such as 40% or more, such as 50% or more, such as 75% or more, such as 90% or more, such as 95% or more, such as 99% or more and including reducing agitated behaviors in the subject in the subject by 99.9% or more. Agitated behavior may be assessed by any convenient protocol such as assessed by the Neuropsychiatric Inventory (NPI).

In yet other embodiments, the amount of the one or more fatty acid (3-hydroxyester compounds and/or one or more esters of butanediol administered to the subject is sufficient to reduce delirium in the subject. For example, the subject methods may include administering an amount of the subject fatty acid (3-hydroxyester compounds or fatty acid esters of butanediol sufficient to reduce delirium in the subject by 5% or more, such as 10% or more, such as 15% or more, such as 25% or more, such as 40% or more, such as 50% or more, such as 75% or more, such as 90% or more, such as 95% or more, such as 99% or more and including reducing delirim in the subject in the subject by 99.9% or more.

In still other embodiments, the amount of the one or more fatty acid β-hydroxyester compounds and/or one or more esters of butanediol administered to the subject is sufficient to reduce stress experienced by a caregiver to the subject. For example, the subject methods may include administering an amount of the subject fatty acid β-hydroxyester compounds or fatty acid esters of butanediol sufficient to reduce stress experienced by a caregiver to the subject by 5% or more, such as 10% or more, such as 15% or more, such as 25% or more, such as 40% or more, such as 50% or more, such as 75% or more, such as 90% or more, such as 95% or more, such as 99% or more and including reducing stress experienced by a caregiver to the subject in the subject by 99.9% or more. Caregiver stresses may be assessed by any convenient protocol such as assessed by the the Perceived Stress Scale (PSS).

In practicing the subject methods, protocols for specific subjects may vary, such as for example by age, weight, severity of the pain, the general health of the subject, as well as the particular concentration of the fatty acid β-hydroxyester compound and/or fatty acid ester of butanediol being administered. In embodiments, the dosage delivered during administration may vary, in some instances, ranging from 5 mg to 800 mg. As such, depending on the physiology of the subject as well as the desired therapeutic effect, the dosage of provided by subject methods may range, from 5 to 800 mg, such as 10 to about 500 mg, such as 20 to 400 mg, such as 25 to 350 mg, such as 30 to 300 mg, such as 40 to 250 mg and including 40 to 200 mg.

Therefore, the dosage interest may vary, ranging from about 0.1 g/kg to 25 g/kg per day, such as from 0.1 g/kg to 20 g/kg per day, such as 0.1 g/kg to 18 g/kg per day, such as 0.1 g/kg to 15 g/kg per day, such as 0.1 g/kg to 10 g/kg per day, and including 0.1 g/kg to 5 g/kg per day, such as from 0.5 g/kg to 10 g/kg per day, such as from 0.5 g/kg to 9 g/kg per day, such as from 0.5 g/kg to 8 g/kg per day, such as from 0.5 g/kg to 5 g/kg per day, such as from 0.5 g/kg to 3 g/kg per day, such as from 0.5 g/kg to 2 g/kg per day and including from 0.5 g/kg to 1 g/kg per day. In certain instances, the dosage is 1 g/kg per day. In other embodiments, the dosage may range from 0.1 to 6.5 g/kg four times per day (QID), such as 0.1 to 5 g/kg QID, such as 0.1 g/kg to 4 g/kg QID. In other embodiments, the oral dosage may range from 0.01 g/kg to 8.5 g/kg three times per day (TID), such as 0.1 g/kg to 6 g/kg TID, such as 0.1 g/kg to 5 g/kg TID, and including as 0.1 g/kg to 4 g/kg TID. In yet other embodiments, the oral dosage may range from 0.1 g/kg to 13 g/kg two times per day (BID), such as 0.1 g/kg to 12 g/kg BID, such as 5 g/kg to 10 g/kg BID, including 0.1 g/kg to 8 g/kg BID. The amount of compound administered will depend on the physiology of the subject, the absorptivity of fatty acid β-hydroxyester compound and/or fatty acid ester of butanediol by the subject, as well as the magnitude of therapeutic effect desired. Dosing schedules may include, but is not limited to administration five times per day, four times per day, three times per day, twice per day, once per day, three times per week, twice per week, once per week, twice per month, once per month, and any combination thereof.

In some embodiments, the subject methods may include chronic administration requiring the subject methods and compositions in multiple doses over an extended period, for example over one month and for up to 10 years.

The duration between dosage intervals in a multiple dosage interval treatment regimen may vary, depending on the physiology of the subject or by the treatment regimen as determined by a health care professional. In certain instances, the duration between dosage intervals in a multiple dosage treatment regimen may be predetermined and follow at regular intervals. As such, the time between dosing intervals may vary and may be 0.5 hours or longer, such as 1 hour or longer, such as 2 hours or longer, such as 4 hours or longer, such as 8 hours or longer, such as 12 hours or longer, such as 16 hours or longer, such as 24 hours or longer, such as 48 hours or longer and including 72 hours or longer.

In certain embodiments, the subject methods include administering one or more fatty acid β-hydroxyester compounds or pharmaceutically acceptable salts thereof and/or one or more esters of butanediol or pharmaceutically acceptable salts thereof to the subject in combination with a ketogenic diet. The phrase "ketogenic diet" is used herein in its conventional sense to refer to a diet, which provides, after consumption, digestion and metabolism, ketone bodies as a major source of energy. Ketone bodies physiologically provided by the ketogenic diet include acetoacetate, β-hydroxybutyrate and acetone. Suitable ketogenic diets may include, but are not limited those described in Fenton et al., ICAN 2009, 1:338; Neal et al., Lancet Neurology 2008, 7:500; Hartman and Vinning, Epilepsia 2007, 1:31; Kossoff et al., Epilepsia 2009, 50:304 the disclosures of which are herein incorporated by reference. In practicing the subject methods, the subject fatty acid β-hydroxyester compounds or pharmaceutically acceptable salts thereof and/or esters of butanediol or pharmaceutically acceptable salts thereof may be administered before, after or in conjunction with the ketogenic diet. In certain embodiments, the subject methods include administering the subject fatty acid β-hydroxyester compounds or pharmaceutically acceptable salts thereof and/or esters of butanediol or pharmaceutically acceptable salts thereof prior to commencing the ketogenic diet. In other embodiments, methods include administering the subject fatty acid β-hydroxyester compounds or pharmaceutically acceptable salts thereof and/or esters of butanediol or pharmaceutically acceptable salts thereof after completing one or more intervals of a ketogenic diet. In still other embodiments, methods include administering the subject fatty acid β-hydroxyester compounds or pharmaceutically acceptable salts thereof and/or esters of butanediol or pharmaceutically acceptable salts thereof in conjunction with the ketogenic diet.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-48 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A compound of formula I:

Formula I wherein
$R_1$ is H or C(1-6) alkyl or substituted alkyl; and
$R_2$ and $R_3$ are independently unsubstituted or substituted C(4-30) alkyl.

2. The compound according to 1, wherein $R_1$ is an unsubstituted C(1-6) alkyl.

3. The compound according to 2, wherein $R_1$ is methyl.

4. The compound according to any one of 1-3, wherein $R_2$ and $R_3$ are independently unsubstituted C(6-18) alkyl.

5. The compound according to any one of 1-3, wherein $R_2$ and $R_3$ are independently unsubstituted C6 alkyl.

6. The compound according to any one of 1-3, wherein $R_2$ and $R_3$ are independently unsubstituted C8 alkyl.

7. A compound according to 1, wherein the compound is of formula Ia:

Formula Ia wherein
R₁ is H or C(1-6) alkyl or substituted alkyl; and
R₂ and R₃ are independently unsubstituted or substituted C(4-30) alkyl.

8. The compound according to 7, wherein R₁ is an unsubstituted C(1-6) alkyl.

9. The compound according to 8, wherein R₁ is methyl.

10. The compound according to any one of 7-9, wherein R₂ and R₃ are independently unsubstituted C(6-18) alkyl.

11. The compound according to any one of 7-9, wherein R₂ and R₃ are independently unsubstituted C6 alkyl.

12. The compound according to any one of 7-9, wherein R₂ and R₃ are independently unsubstituted C8 alkyl.

13. A compound according to 1, wherein the compound is of formula Ib:

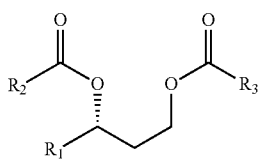

Formula Ib wherein
R₁ is H or C(1-6) alkyl or substituted alkyl; and
R₂ and R₃ are independently unsubstituted or substituted C(4-30) alkyl.

14. The compound according to 13, wherein R₁ is an unsubstituted C(1-6) alkyl.

15. The compound according to 14, wherein R₁ is methyl.

16. The compound according to any one of β-15, wherein R₂ and R₃ are independently unsubstituted C(6-18) alkyl.

17. The compound according to any one of β-15, wherein R₂ and R₃ are independently unsubstituted C6 alkyl.

18. The compound according to any one of β-15, wherein R₂ and R₃ are independently unsubstituted C8 alkyl.

19. A composition comprising a compound according to any one of 1-18 and a pharmaceutically acceptable carrier.

20. A method comprising administering to a subject in need thereof, a therapeutically effective amount of a compound according to any one of 1-18 or a composition according to 19.

21. The method according to 20, wherein the therapeutically effective amount is sufficient to reduce epileptiform activity in the brain of the subject.

22. A method for treating one or more of Alzheimer's disease, epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, Niemann-Pick Type C disease, age-related macular degeneration, gout, atherosclerosis, rheumatoid arthritis and multiple sclerosis comprising:
administering to a subject a therapeutically effective amount of a compound according to any one of 1-18 or a composition according to 19.

23. The method according to 22, wherein the therapeutically effective amount is sufficient to reduce epileptiform activity in the brain of the subject.

24. A method of reducing epileptiform activity in the brain of a subject, the method comprising administering to the subject a therapeutically effective amount of a compound according to any one of 1-18 or a composition according to 19.

25. A food supplement comprising a compound according to any one of 1-18.

26. A composition comprising:
a food supplement comprising a compound according to any one of 1-18; and
one or more additional components of a ketogenic diet.

27. The composition according to 26, wherein the compound is present in the composition in an amount of from about 1% w/w to about 25% w/w.

28. The composition according to 26, wherein the compound is present in the composition in an amount of from about 5% w/w to about 15% w/w.

29. The composition according to 26, wherein the compound is present in the composition in an amount of about 10% w/w.

30. The composition according to 26, wherein the ketogenic diet comprises a ratio by mass of fat to protein and carbohydrates of from about 2:1 to about 10:1.

31. The composition according to 30, wherein the ketogenic diet comprises a ratio by mass of fat to protein and carbohydrates of from about 3:1 to about 6:1.

32. The composition according to 30, wherein the ketogenic diet comprises a ratio by mass of fat to protein and carbohydrates of about 4:1.

33. A compound of formula II:

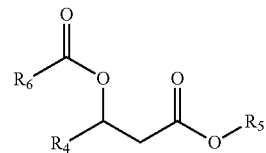

Formula II wherein
R4 is H or C(1-6) alkyl or substituted alkyl; and
R5 and R6 are independently unsubstituted or substituted C(4-30) alkyl.

34. The compound according to 33, wherein R4 is an unsubstituted C(1-6) alkyl.

35. The compound according to 34, wherein R4 is methyl.

36. The compound according to any one of 33-35, wherein R5 and R6 are independently unsubstituted C(6-18) alkyl.

37. The compound according to any one of 33-35, wherein R5 and R6 are independently unsubstituted C6 alkyl.

38. The compound according to any one of 33-35, wherein R5 and R6 are independently unsubstituted C8 alkyl.

39. A compound according to 33, wherein the compound is of formula Ia:

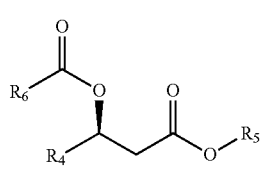

Formula IIa wherein
R4 is H or C(1-6) alkyl or substituted alkyl; and
R5 and R6 are independently unsubstituted or substituted C(4-30) alkyl.

40. The compound according to 39, wherein R4 is an unsubstituted C(1-6) alkyl.
41. The compound according to 40, wherein R4 is methyl.
42. The compound according to any one of 39-41, wherein R5 and R6 are independently unsubstituted C(6-18) alkyl.
43. The compound according to any one of 39-41, wherein R5 and R6 are independently unsubstituted C6 alkyl.
44. The compound according to any one of 39-41, wherein R5 and R6 are independently unsubstituted C8 alkyl.
45. A compound according to 33, wherein the compound is of formula Ib:

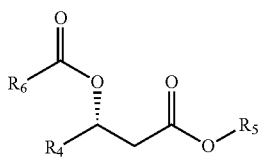

Formula IIb wherein
R4 is H or C(1-6) alkyl or substituted alkyl; and
R5 and R6 are independently unsubstituted or substituted C(4-30) alkyl.
46. The compound according to 45, wherein R4 is an unsubstituted C(1-6) alkyl.
47. The compound according to 46, wherein R4 is methyl.
48. The compound according to any one of 45-47, wherein R5 and R6 are independently unsubstituted C(6-18) alkyl.
49. The compound according to any one of 45-47, wherein R5 and R6 are independently unsubstituted C6 alkyl.
50. The compound according to any one of 45-47, wherein R5 and R6 are independently unsubstituted C8 alkyl.
51. A composition comprising a compound according to any one of 33-50 and a pharmaceutically acceptable carrier.
52. A method comprising administering to a subject in need thereof, a therapeutically effective amount of a compound according to any one of 33-50 or a composition according to 51.
53. The method according to 52, wherein the therapeutically effective amount is sufficient to reduce epileptiform activity in the brain of the subject.
54. A method for treating one or more of Alzheimer's disease, epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, Niemann-Pick Type C disease, age-related macular degeneration, gout, atherosclerosis, rheumatoid arthritis and multiple sclerosis comprising:
administering to a subject a therapeutically effective amount of a compound according to any one of 33-50 or a composition according to 51.
55. The method according to 54, wherein the therapeutically effective amount is sufficient to reduce epileptiform activity in the brain of the subject.
56. A method of reducing epileptiform activity in the brain of a subject, the method comprising administering to the subject a therapeutically effective amount of a compound according to any one of 33-50 or a composition according to 51.
57. A food supplement comprising a compound according to any one of 33-50.

58. A composition comprising:
a food supplement comprising a compound according to any one of 33-50; and
one or more components of a ketogenic diet.
59. The composition according to 58, wherein the compound is present in the composition in an amount of from about 1% w/w to about 25% w/w.
60. The composition according to 58, wherein the compound is present in the composition in an amount of from about 5% w/w to about 15% w/w.
61. The composition according to 58, wherein the compound is present in the composition in an amount of about 10% w/w.
62. The composition according to 58, wherein the ketogenic diet comprises a ratio by mass of fat to protein and carbohydrates of from about 2:1 to about 10:1.
63. The composition according to 58, wherein the ketogenic diet comprises a ratio by mass of fat to protein and carbohydrates of from about 3:1 to about 6:1.
64. The composition according to 58, wherein the ketogenic diet comprises a ratio by mass of fat to protein and carbohydrates of about 4:1.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.
General Synthetic Procedures
The ketone esters described herein, may be prepared by chemical synthesis protocols known to those of skill in the art (See e.g., Green et al., "Protective Groups in Organic Chemistry," (Wiley, 2nd ed. 1991); Harrison et al., "Compendium of Synthetic Organic Methods," Vols. 1 8 (John Wiley and Sons, 1971 1996); "Beilstein Handbook of Organic Chemistry," Beilstein Institute of Organic Chemistry, Frankfurt, Germany; Feiser et al., "Reagents for Organic Synthesis," Volumes 1 17, (Wiley Interscience); Trost et al., "Comprehensive Organic Synthesis," (Pergamon Press, 1991); "Theilheimer's Synthetic Methods of Organic Chemistry," Volumes 1 45, (Karger, 1991); March, "Advanced Organic Chemistry," (Wiley Interscience), 1991; Larock "Comprehensive Organic Transformations," (VCH Publishers, 1989); Paquette, "Encyclopedia of Reagents for Organic Synthesis," (John Wiley & Sons, 1995), Bodanzsky, "Principles of Peptide Synthesis," (Springer Verlag, 1984); Bodanzsky, "Practice of Peptide Synthesis," (Springer Verlag, 1984). Further, starting materials may be obtained from commercial sources or via well-established synthetic procedures.

β-Hydroxyesters Compounds

β-hydroxyester compounds described herein may be obtained via synthetic routes as generically illustrated below:

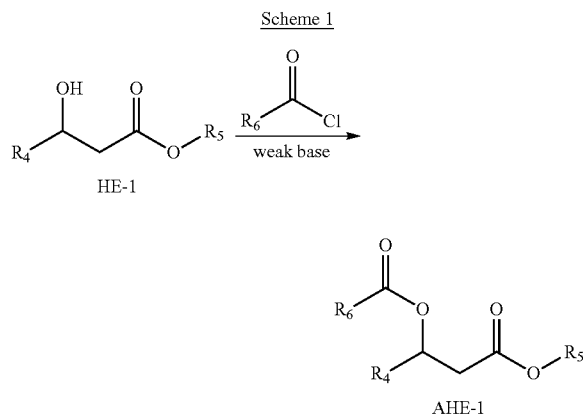

In Scheme 1, the hydroxyl group of β-hydroxyester HE-1 is deprotonated with a weak base (e.g., pyridine) and reacted with a substituted acyl chloride to give acyl-substituted β-hydroxyester AHE-1. $R_4$ may be H or a substituted or unsubstituted C(1-6) alkyl; $R_5$ and $R_6$ are independently substituted or unsubstituted C(4-30) alkyl.

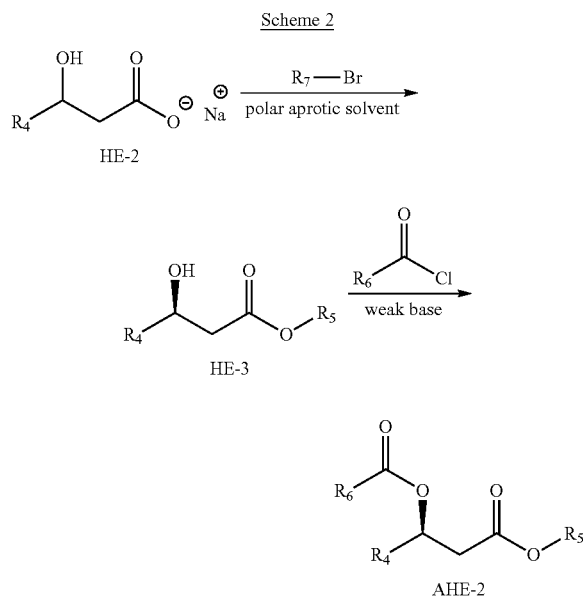

In Scheme 2, sodium β-hydroxyester HE-2 is reacted in a polar aprotic solvent (e.g., dimethylformamide) with an alkyl bromide to give alkyl β-hydroxyester HE-3. Deprotonation of the hydroxyl group of β-hydroxyester KE-3 with a weak base (e.g., pyridine) and reaction with a substituted acyl chloride gives acyl-substituted β-hyrdoxyester AHE-2. $R_4$ may be H or a substituted or unsubstituted C(1-6) alkyl; $R_6$ and $R_7$ are independently substituted or unsubstituted C(4-30) alkyl.

Example 1—Synthesis of acyl substituted ethyl β-hydroxybutyrate

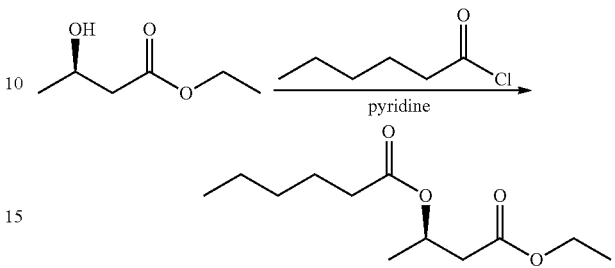

Figure 1B:
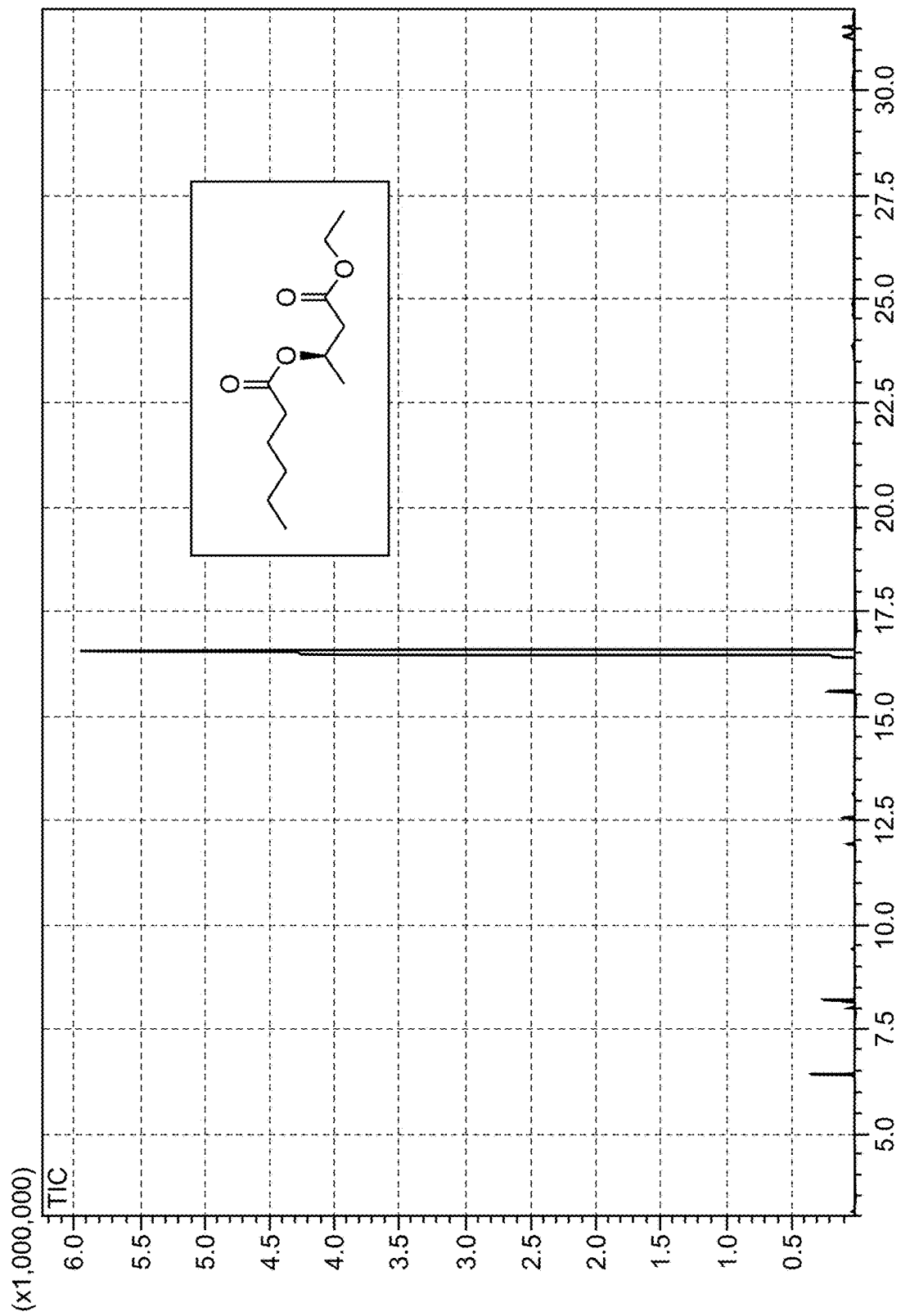
Figure 2A:
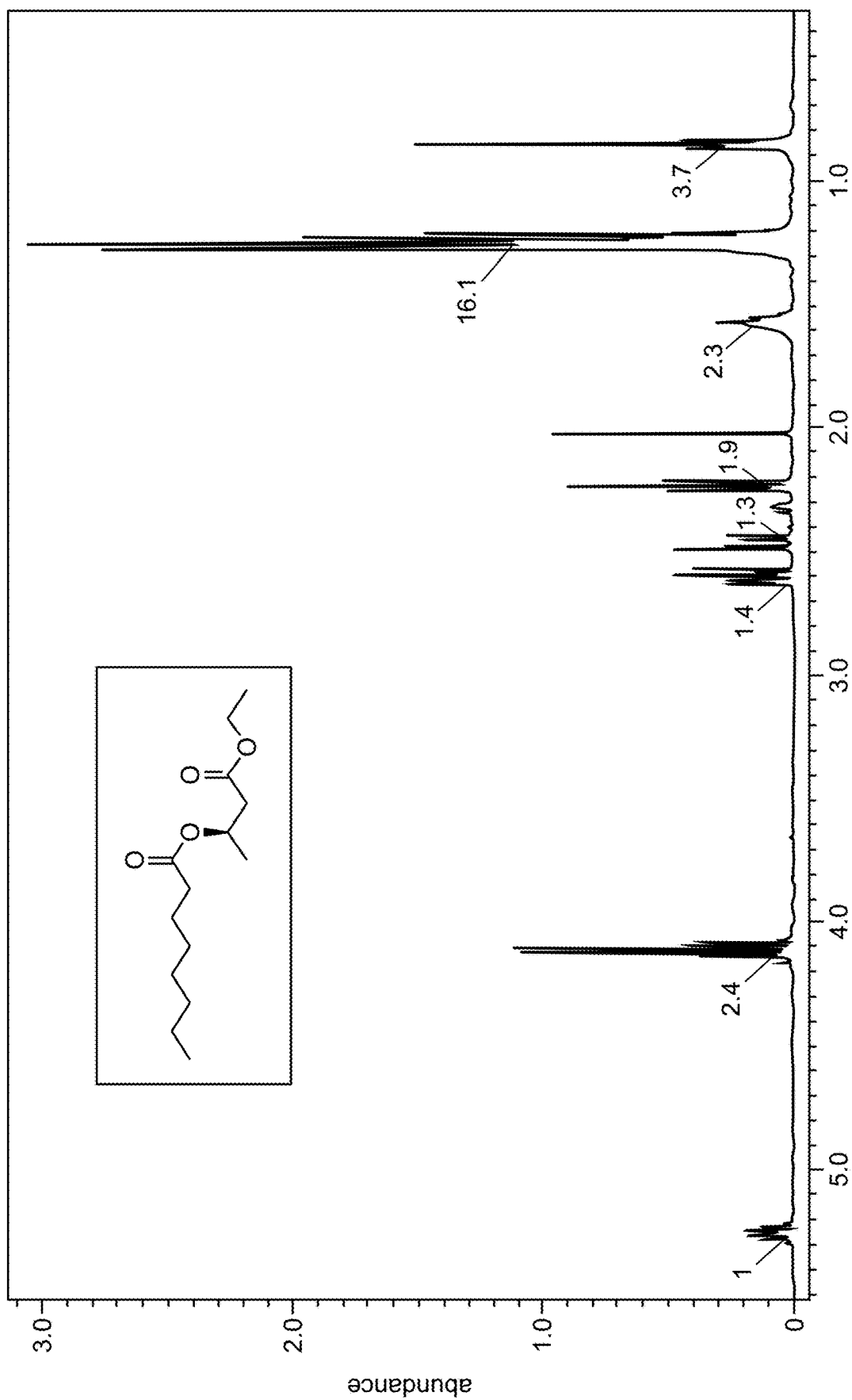
FIGS. 2a and 2b depict the $^1$H-NMR and GC-MS, respectively, of a C8-substituted ester of β-hydroxybutyrate according to certain embodiments.
Figure 2B:
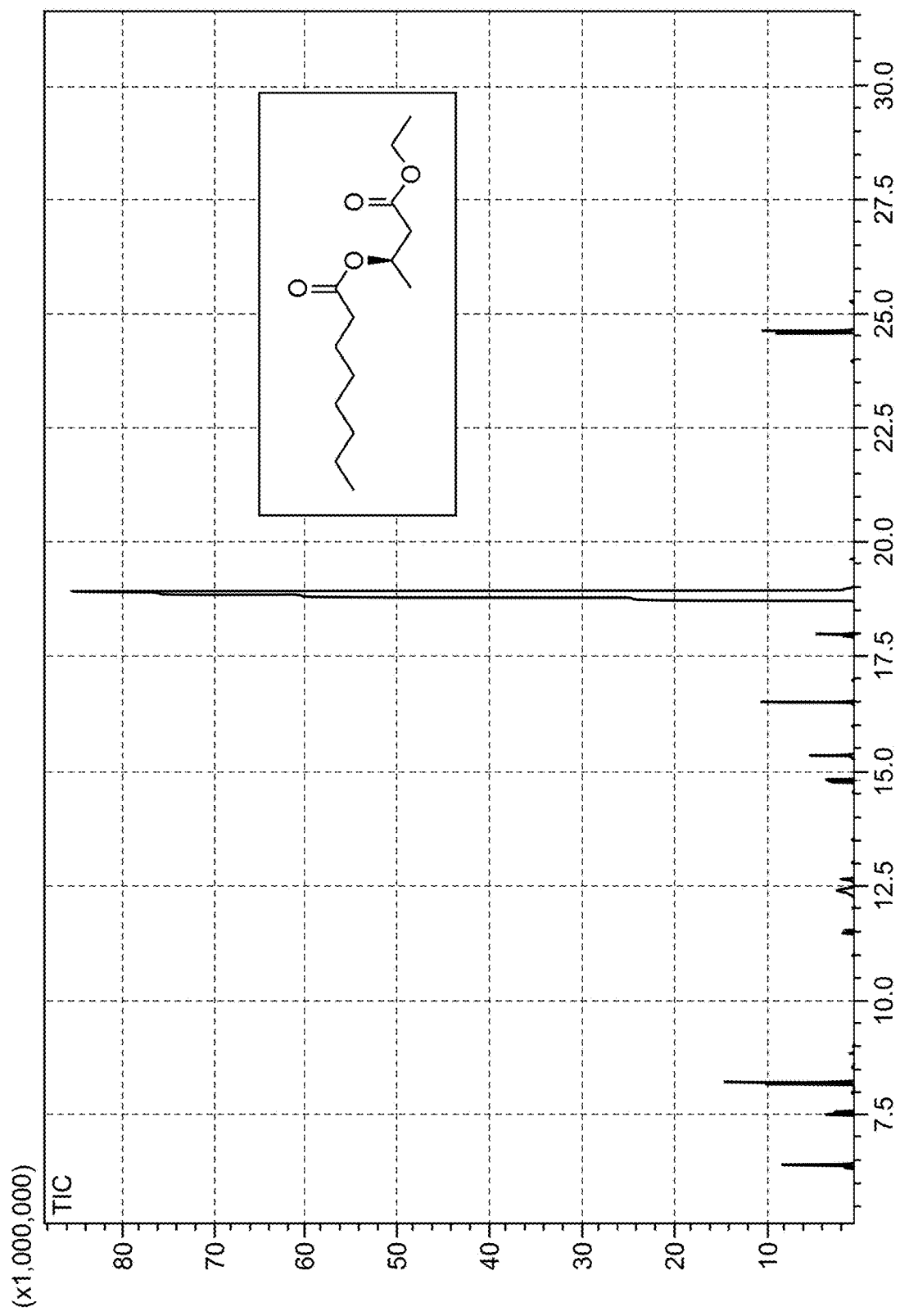

As depicted in Scheme 3, one molar equivalent of R-ethyl β-hydroxybutyrate is dissolved in pyridine to a concentration of 0.2 molar. The solution is placed under nitrogen atmosphere and cooled to 0° C. A substituted (e.g., hexyl, FIGS. 1a-1b and octyl, FIGS. 2a-2b) acyl chloride at 2 molar equivalent is added dropwise via syringe to the β-hydroxyester solution while stirring. The reaction mixture is allowed to warm to room temperature and stirred overnight. The reaction was then loaded into a separatory funnel and diluted with 1.5 volumes of ethyl acetate (based on reaction volume) and was then washed 5 times with 0.5 volumes of hydrochloric acid solution (HCl 10%) then 4 times with 0.5 volumes of a saturated aqueous sodium bicarbonate solution and once with brine. The ethyl acetate layer was then dried with magnesium sulfate, filtered and the solvent removed by rotary evaporation. The crude product was analyzed by $^1$H NMR (FIGS. 1a and 2a) and gas chromatograph mass spectrometry (FIGS. 1b and 2b). Pure (>95%) product was seen, with the main contaminant being pyridine, which was removed by further vacuum pumping.

Example 2—Synthesis of acyl substituted hexyl β-hydroxybutyrate

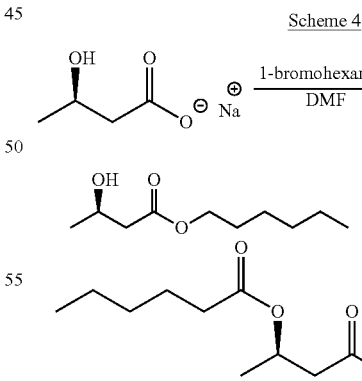

As depicted in Scheme 4, Sodium β-hydroxybutyrate (1 molar equivalent) was suspended in dry dimethylformamide to a concentration of 0.2 molar. 1-bromohexane (0.7 molar equivalents) was added, the reaction vessel was sealed and heated to 60 degrees C. with stirring for 18 hours, during which time the reaction mixture became clear. It was then cooled and loaded into a separatory funnel and diluted with 1.5 volumes of ethyl acetate (based on the reaction volume). It was then washed five times with 0.5 volumes of a saturated aqueous sodium bicarbonate solution and once with brine. The ethyl acetate layer was then dried with magnesium sulfate, filtered, and the solvent removed by rotary evaporation. The crude product was analyzed by 1H NMR and GC-MS. Pure (>95%) product was seen, with the main contaminant being 1-bromohexane, which was removed by further vacuum pumping.

Figure 3A:
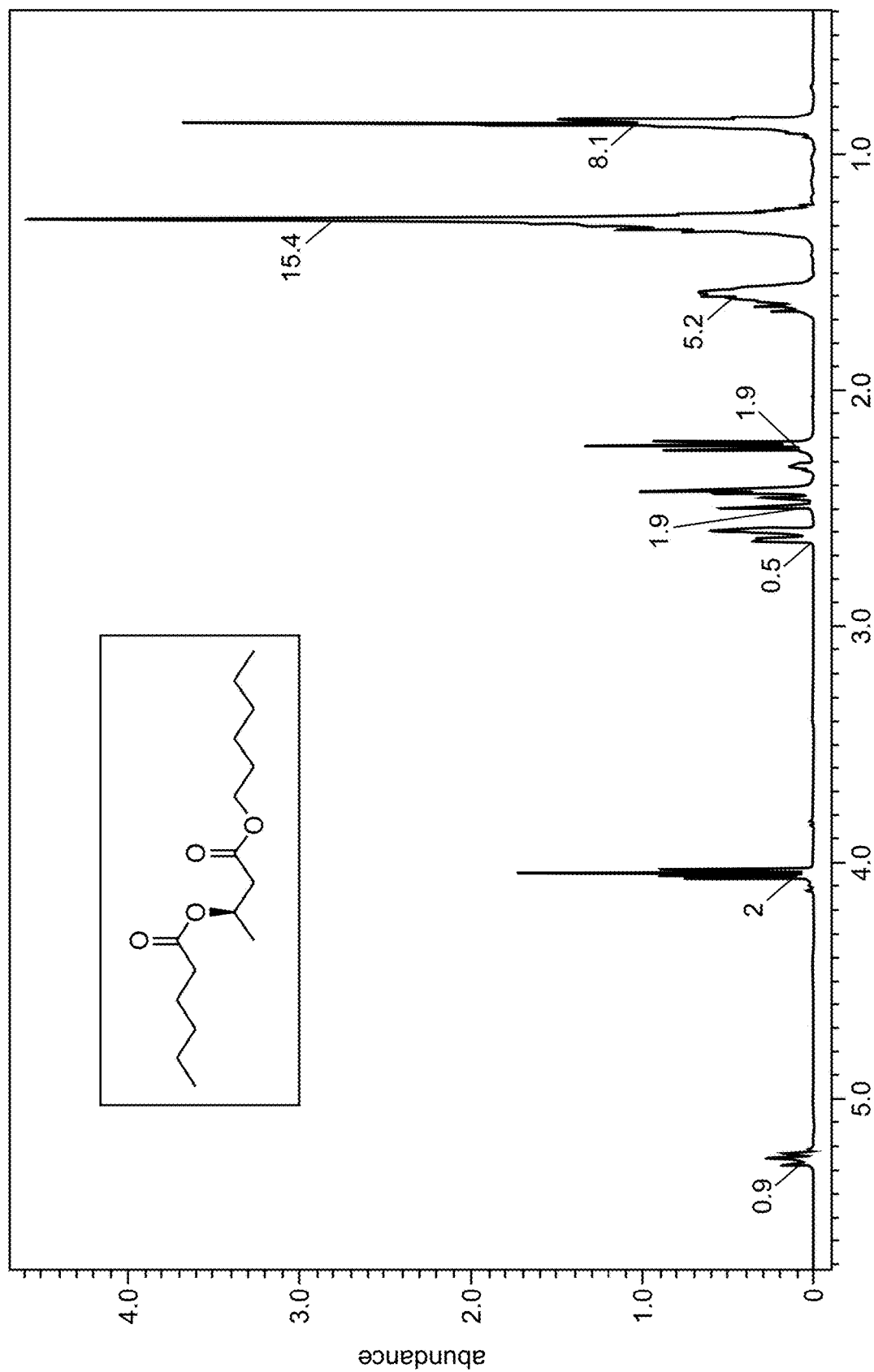
FIGS. 3a and 3b depict the $^1$H-NMR and GC-MS, respectively, of a C6-substituted fatty acid β-hydroxyester compound according to certain embodiments.
Figure 3B:
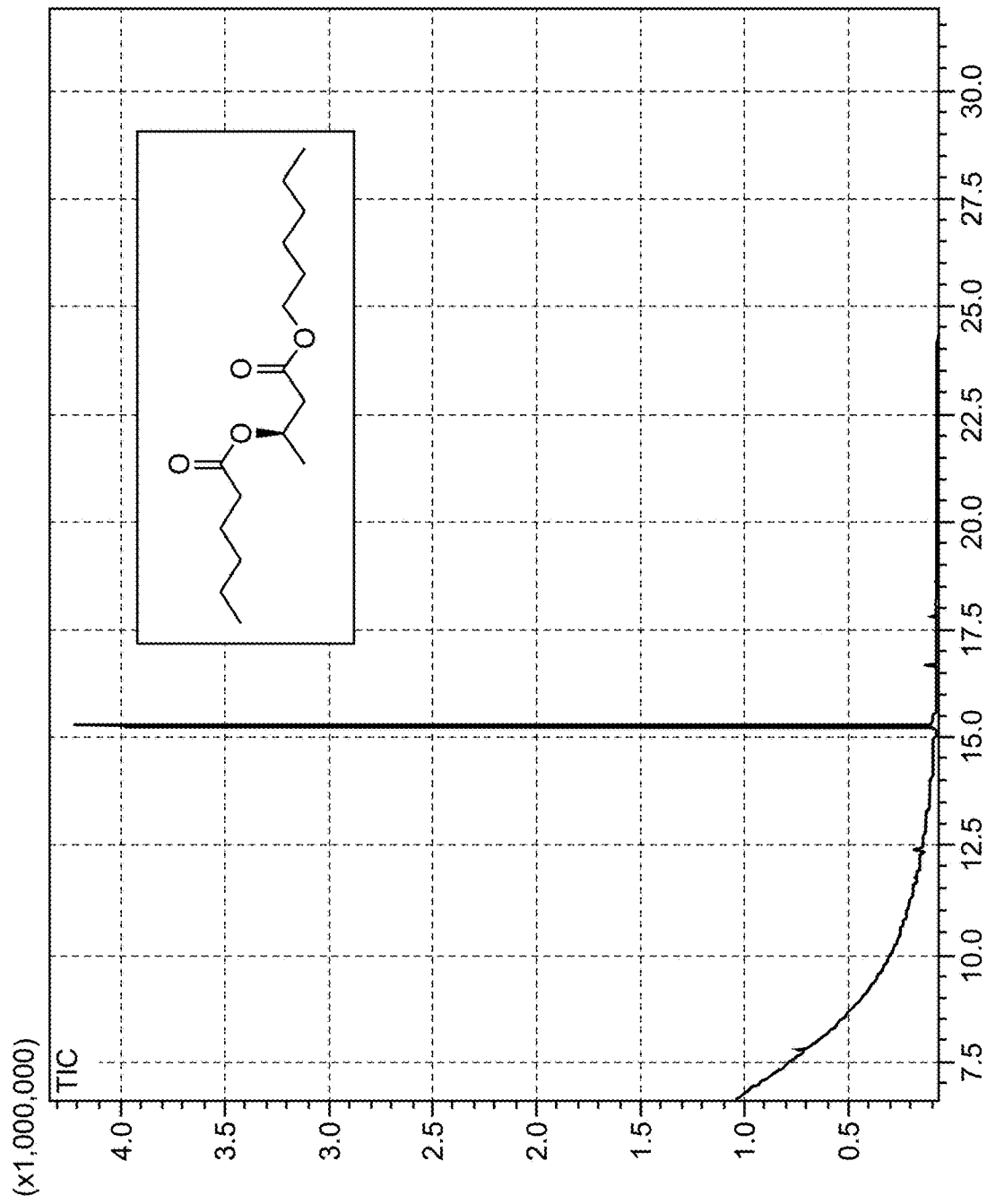

The hexyl β-hydroxybutyrate product was then dissolved in pyridine to a concentration of 0.2 molar. The solution was placed under a nitrogen atmosphere and cooled at 0 deg C. The appropriate acyl chloride (2 molar equivalents) was added dropwise via syringe to the solution with stirring. The reaction mixture was allowed to warm to room temperature and stirred overnight. The reaction mixture was then loaded into a separatory funnel and diluted with 1.5 volumes of ethyl acetate (based on the reaction volume). It was then washed five times with 0.5 volumes of a hydrochloric acid solution (10%), then four times with 0.5 volumes of a saturated aqueous sodium bicarbonate solution and once with brine. The ethyl acetate layer was then dried with magnesium sulfate, filtered, and the solvent removed by rotary evaporation. The crude product was analyzed by $^1$H NMR (FIG. 3a) and GC-MS (FIG. 3b). Pure (>95%) product was seen, with the main contaminant being pyridine, which was removed by further vacuum pumping.

1,3-Butanediol Esters 1,3-butanediol esters described herein may be obtained via synthetic routes as generically illustrated below:

Scheme 5

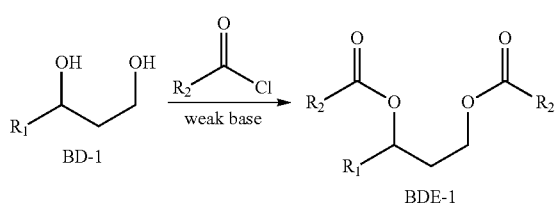

BD-1 → BDE-1

In Scheme 5, the hydroxyl groups of 1,3-butandiol BD-1 is deprotonated with a weak base (e.g., pyridine) and reacted with at least 2 equivalents of a substituted acyl chloride to give homo-acyl-substituted 1,3-butanediol ester BDE-1. $R_1$ may be H or a substituted or unsubstituted C(1-6) alkyl; $R_2$ is substituted or unsubstituted C(4-30) alkyl.

Scheme 6

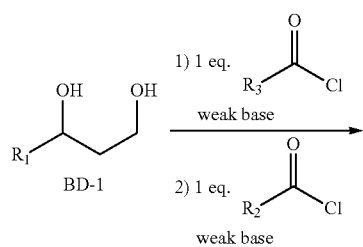

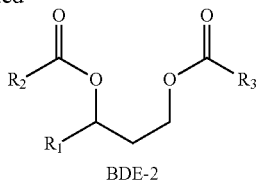

BDE-2

In Scheme 6, each hydroxyl group of 1,3-butandiol BD-1 is stepwise deprotonated with a weak base (e.g., pyridine) and reacted with 1 equivalent of a first substituted acyl chloride and 1 equivalent of a second substituted acyl chloride to give hetero-acyl-substituted 1,3-butanediol ester BDE-2. $R_1$ may be H or a substituted or unsubstituted C(1-6) alkyl; $R_2$ and $R_3$ are independently substituted or unsubstituted C(4-30) alkyl.

Example 3—Synthesis of acyl substituted R-1,3-butanediol

Scheme 7

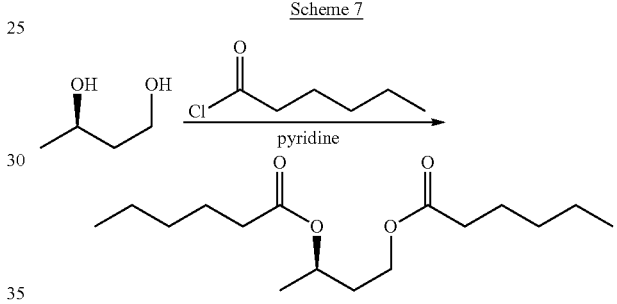

Figure 4A:
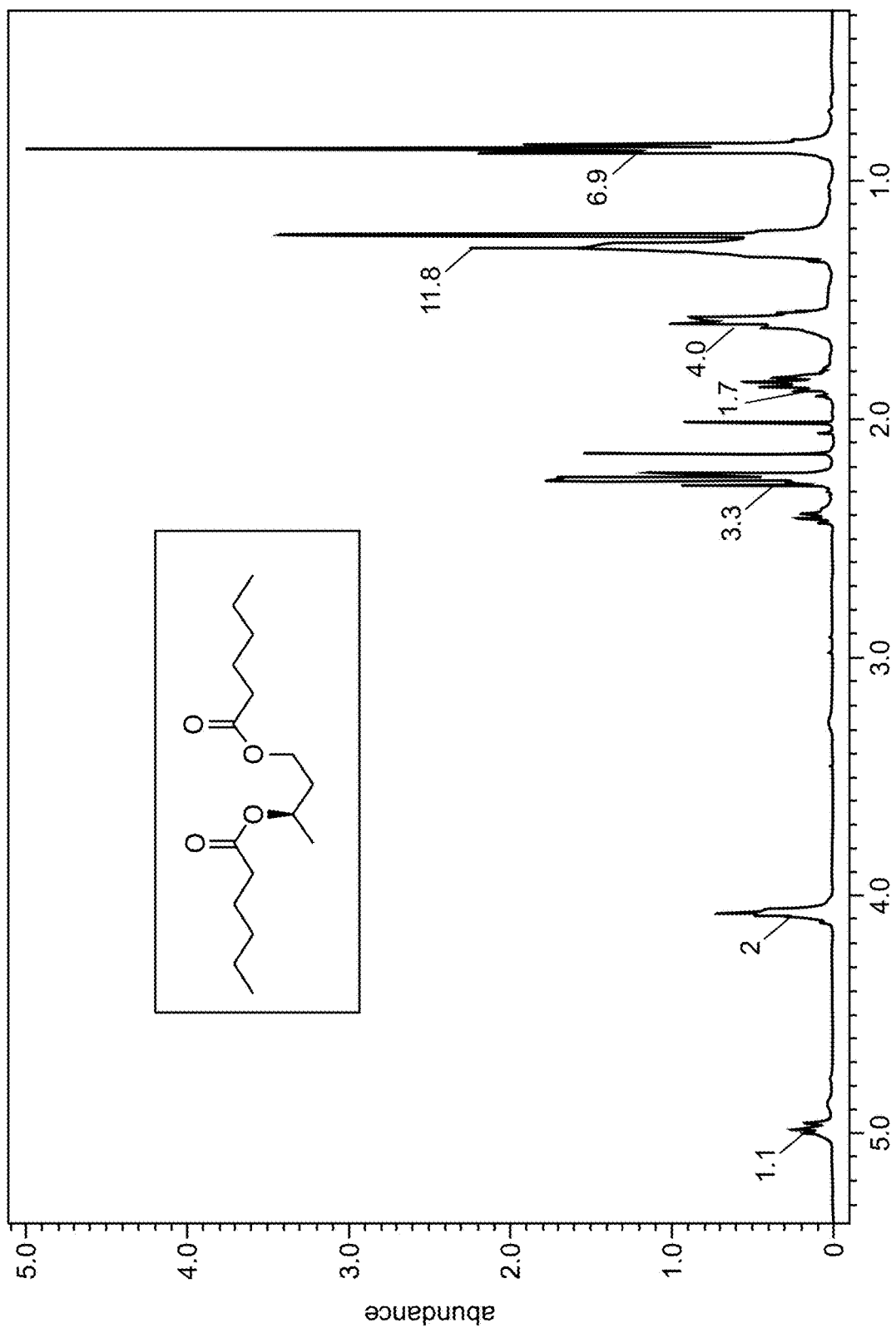
FIGS. 4a and 4b depict the $^1$H-NMR and GC-MS, respectively, of a C6-acyl substituted ester of butanediol according to certain embodiments.
Figure 4B:
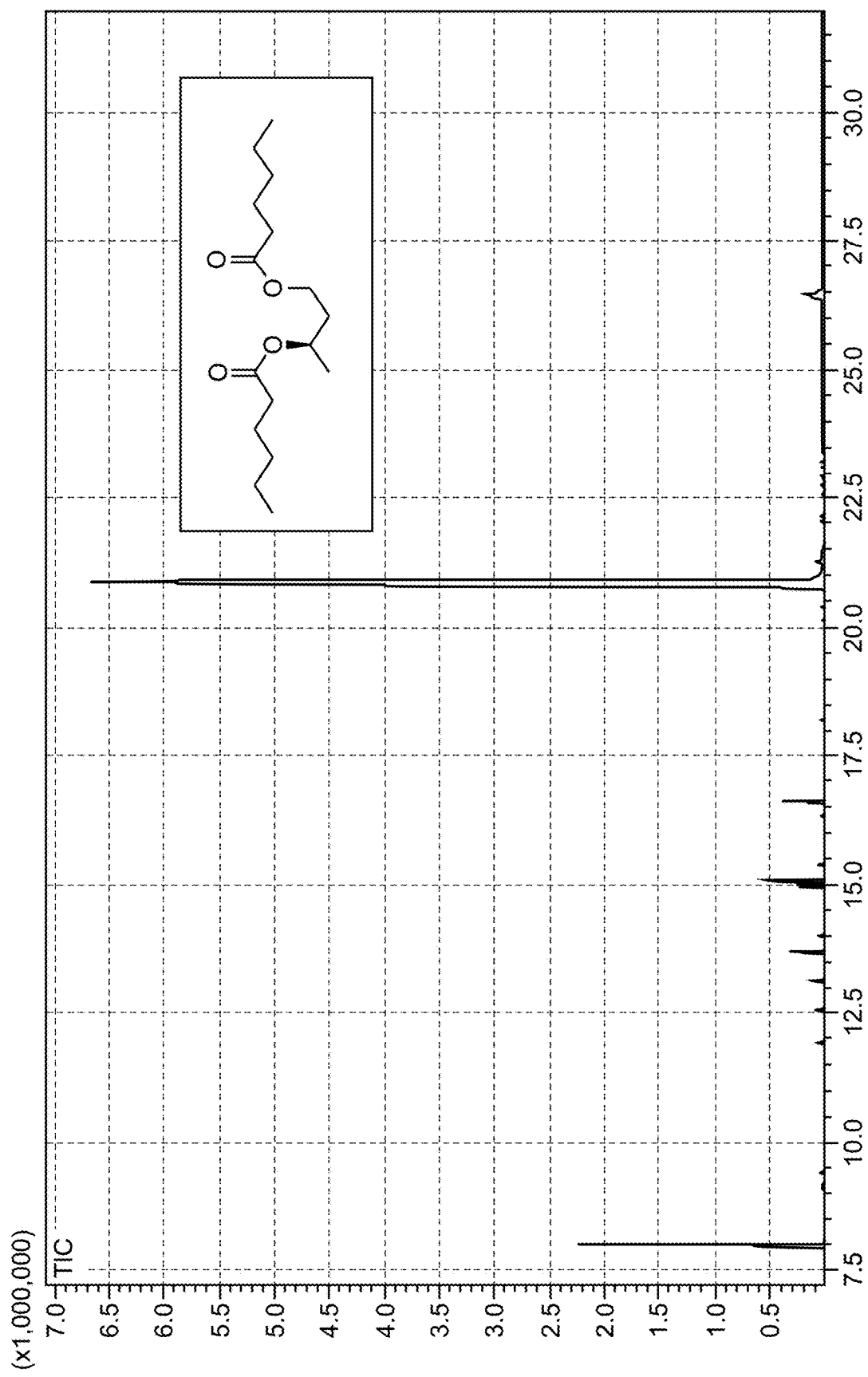
Figure 5A:
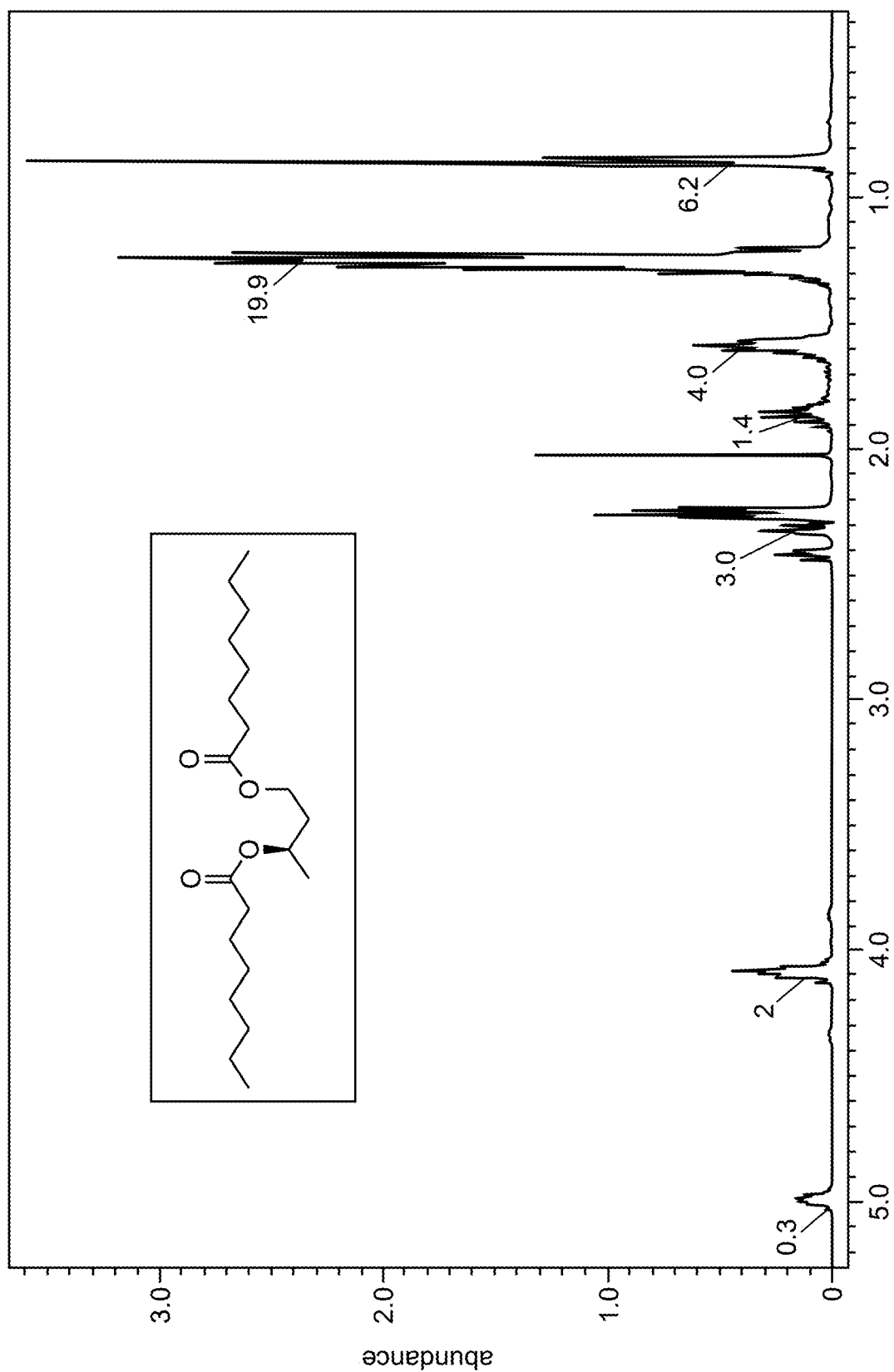
FIGS. 5a and 5b depict the $^1$H-NMR and GC-MS, respectively, of a C8-acyl substituted ester of butanediol according to certain embodiments.
Figure 5B:
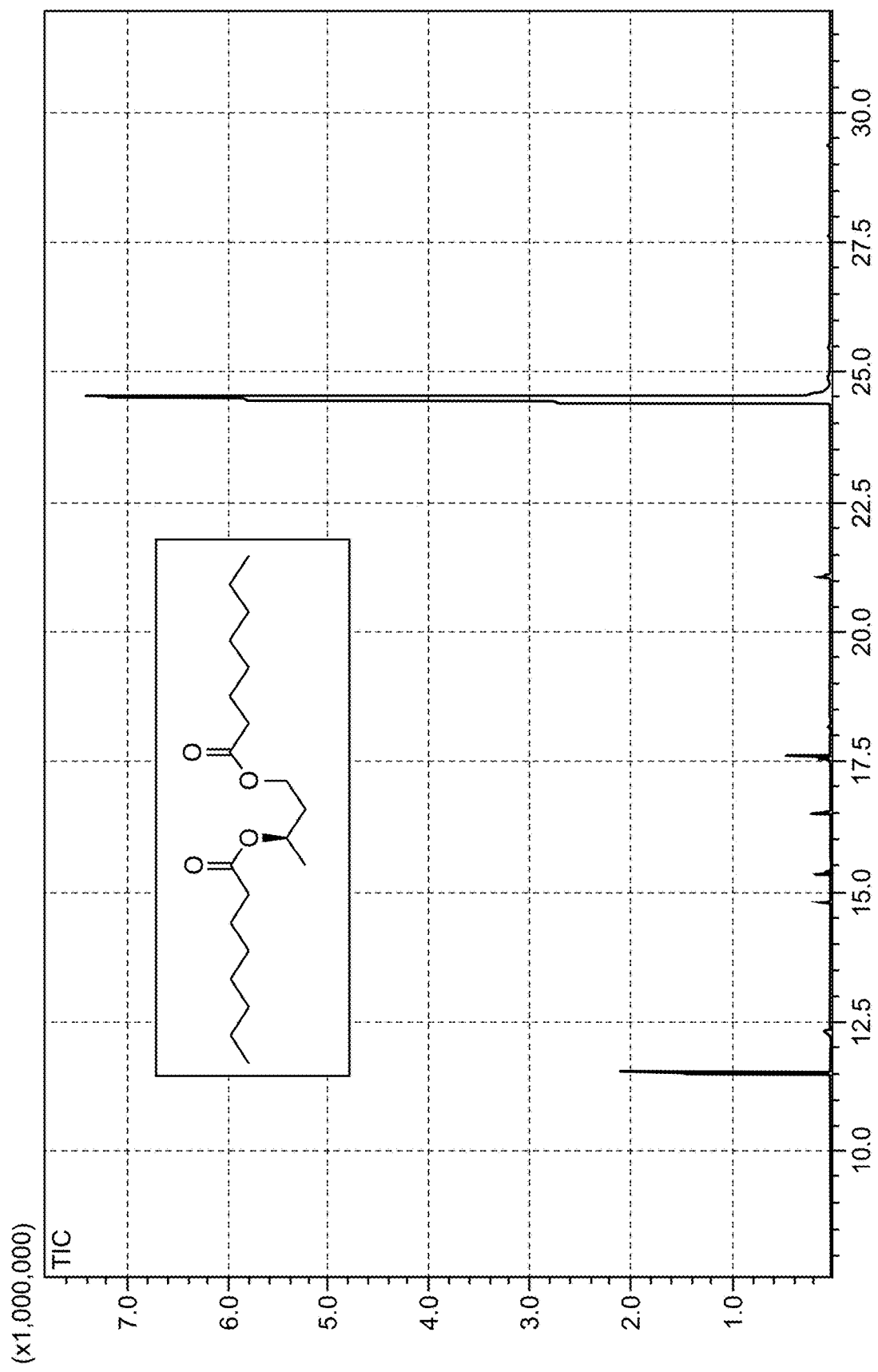

As depicted in Scheme 7, R-1,3-butanediol (1 molar equivalent) was dissolved in pyridine to a concentration of 0.2 molar. The solution was placed under a nitrogen atmosphere and cooled at 0 deg C. 3-3.5 molar equivalents of the appropriate acyl chloride (hexyl, FIGS. 4a-4b; octyl, FIGS. 5a-5b) was added dropwise via syringe to the solution with stirring. The reaction mixture was allowed to warm to room temperature and stirred overnight. The reaction mixture was then loaded into a separatory funnel and diluted with 1.5 volumes of ethyl acetate (based on the reaction volume). It was then washed five times with 0.5 volumes of a hydrochloric acid solution (10%), then four times with 0.5 volumes of a saturated aqueous sodium bicarbonate solution and once with brine. The ethyl acetate layer was then dried with magnesium sulfate, filtered, and the solvent removed by rotary evaporation. The crude product was analyzed by $^1$H NMR (FIGS. 4a and 5a) and GC-MS (FIGS. 4b and 5b). Pure (>95%) product was seen, with the main contaminant being pyridine, which was removed by further vacuum pumping.

Example 4—Biological Function in Increasing BHB Levels in Blood of Wild-Type C57BL/6 Male Mice Materials and Methods C6 and C8 esters of butanediol and C6 and C8 esters of β-hydroxybutyrate were synthesized as described above and purified for testing in wild-type C57BL/6Ncrl male mice obtained from Charles River Laboratories. Mice were 8 months old at the time of the experiment. The biological function of C6 and C8 esters of butanediol and β-hydroxybutyrate was tested by intraperitoneal injection at two doses each, 50 uL and 100 uL. Injection was performed approximately 9 am (mice are maintained on 7 a-7 p light-dark cycle) and mice had access to food and water at all times. The molar quantity injected varied from 0.13-0.41 millimoles depending on the compound and dose. The subject mice weighed approximately 30 grams, so the quantity of compound injected ranged approximately from 1 g/kg to 3 g/kg. For comparison, these amounts could theoretically supply about ½0 of a mouse's daily caloric needs—equivalent in humans to around 100 calories. Blood was drawn by distal tail nick just prior to injection (baseline) and at 30 min, 1 hour, 2 hours, 4 hours, and 6 hours after injection. Approximately 40 uL of blood was collected into lithium-heparin microvettes (Sarstedt CB-300LH) and subsequently centrifuged 15 min at 1500×G at 4° C. to separate plasma. Plasma BHB levels were determined by a colorimetric enzymatic assay (Stanbio Laboratory 2440-058).

Results

Figure 6A:
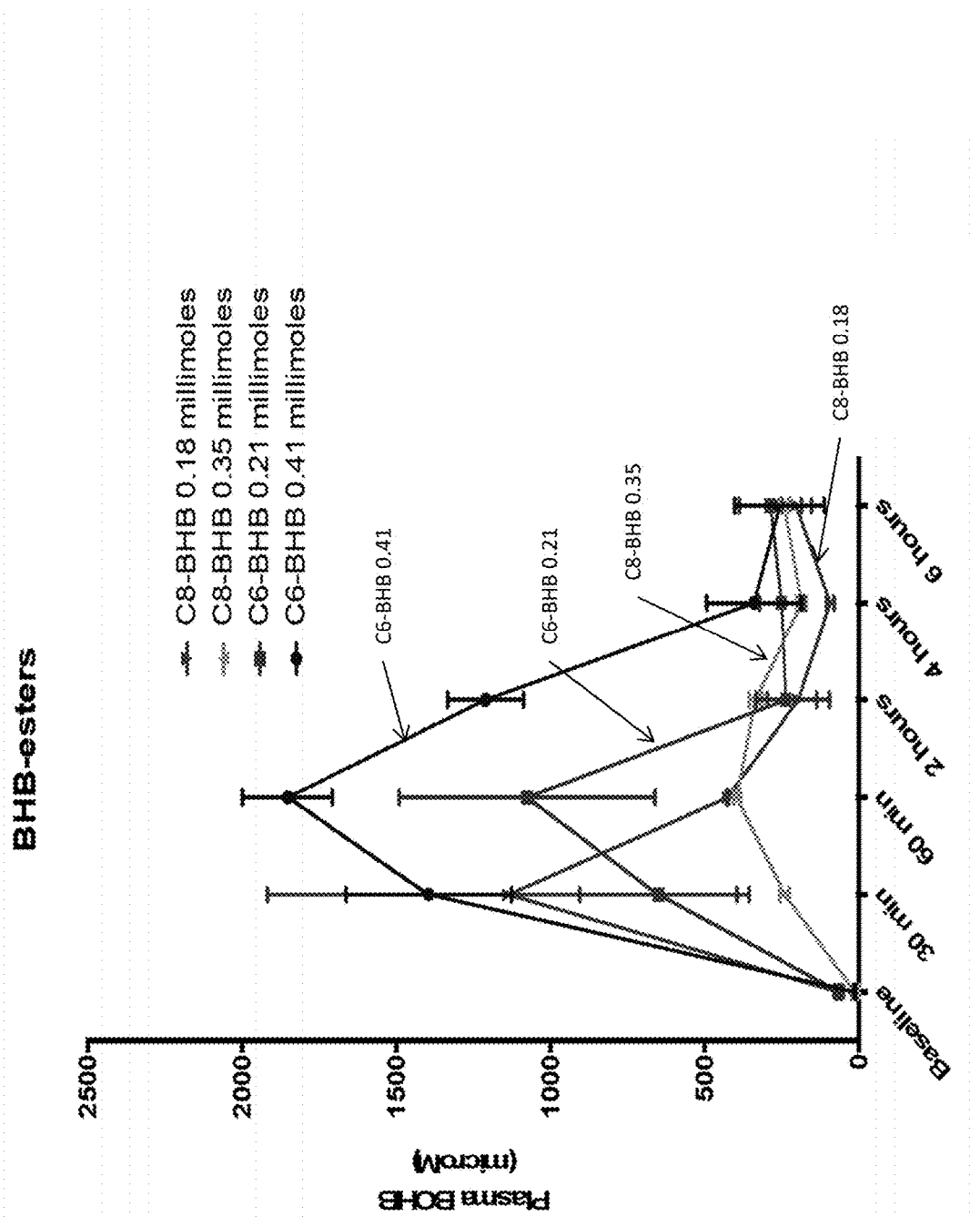
FIGS. 6a-6c depict the biological function of C6 and C8 esters of butanediol and β-hydroxybutyrate as tested by intraperitoneal injection into wild-type C57BL/6 male mice at two doses each.
Figure 6B:
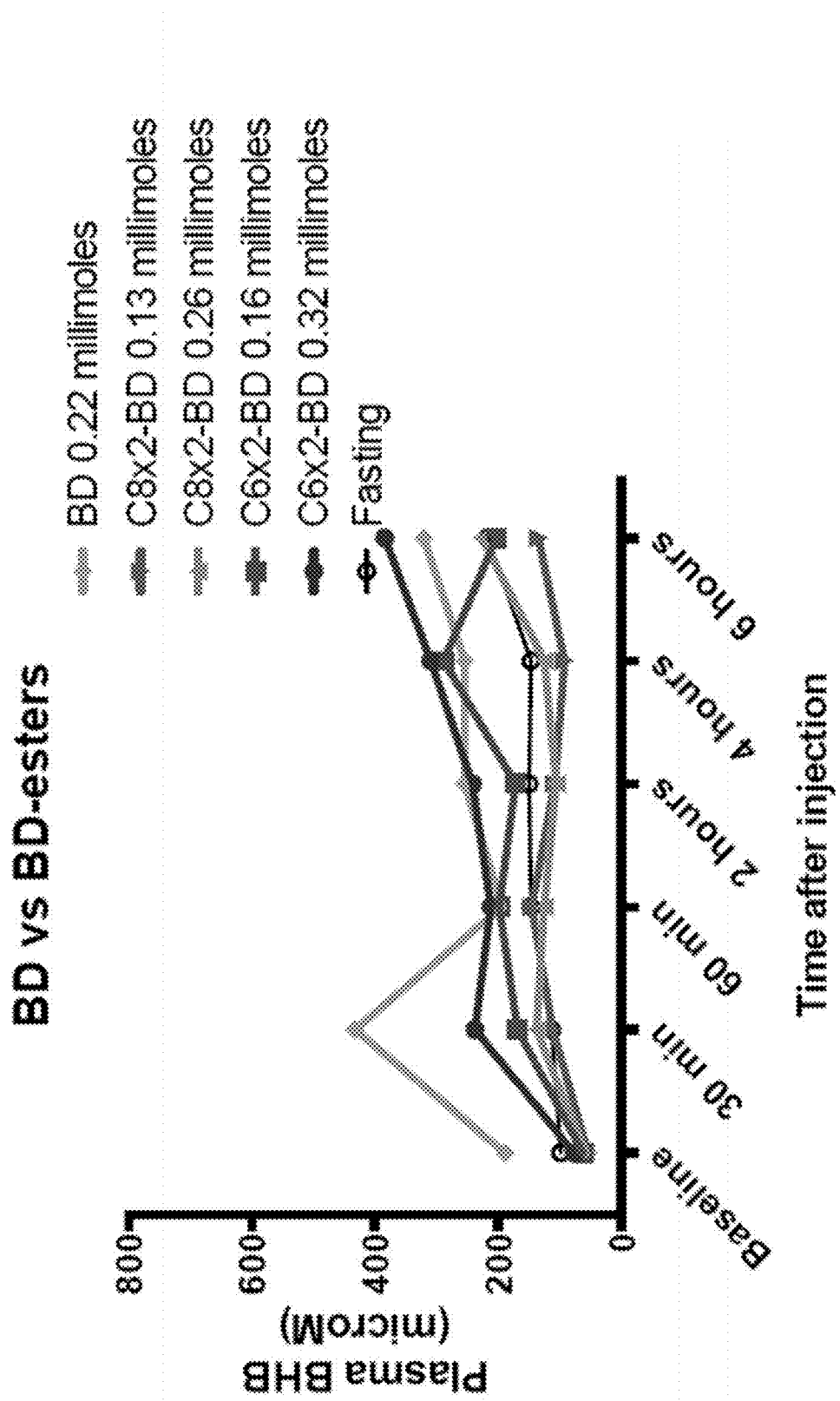
Figure 6C:
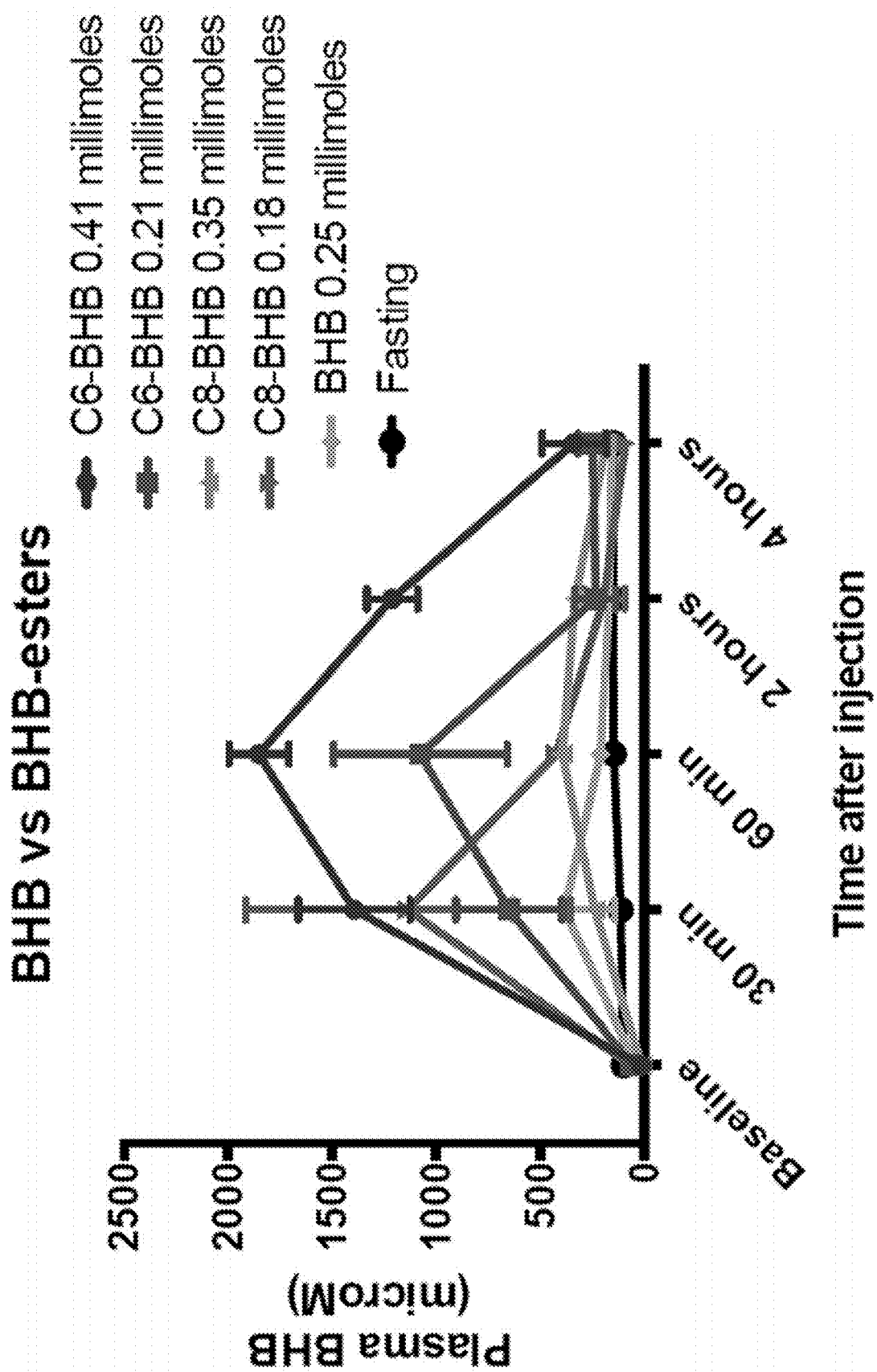

All of the compounds increased blood BHB levels (FIGS. 6a-6c). The C6-BHB and C8-BHB compounds, at both doses tested, increased BHB levels to that seen on a ketogenic diet (0.5-2 mM), or after an overnight fast (1-3 mM) in similar mice (FIG. 6a). The only side effect observed was a mild sedation at the higher dose of C6-BHB. Food intake was not measured, but a 6-hour fast does not significantly increase blood BHB levels (FIG. 6c), so the increase seen with the compounds was not due to inadvertent fasting. Importantly, the increase of blood BHB was higher than that seen by injection of a similar molar dose of BHB (FIG. 6c) or BD alone (FIG. 6b), demonstrating that the fatty acid and BHB/BD components of the compound have the expected separate and additive activities in increasing blood BHB levels. Altogether, these data show that the novel BHB/BD-fatty acid ester compounds have the expected biological function of increasing blood BHB levels, in some cases to the similar extent as an overnight fast and lasting for several hours.

Example 5—Ketogenic Diet Acutely Suppresses Epileptiform Spikes in APPJ20 Mice

Materials and Methods

Ketogenic diet and overnight fasting were tested to determine suppression of epileptiform spikes in one-year-old APPJ20 mice. APPJ20 mice carry a human APP gene with several mutations that cause Alzheimer's disease in humans. Heterozygous mice carrying the APP transgene were studied, with comparison to non-transgenic (NTG), wild-type littermates. These mice show early and severe cognitive deficits, as well as characteristic epileptiform spikes in electroencephalographs (EEG) that contribute to their cognitive deficits. Reductions in the epileptiform spikes by genetic manipulation or by the antiepileptic drug levetiracetam are associated with cognitive improvement. The studies described here all used both male and female mice, and the data is presented as the summary of all mice except where mice are specifically stratified by sex. There were no differences when results were stratified by sex except where specifically noted. The mice and this epileptiform activity are described further in Palop et al., Neuron 2007, 55:697-711.

A longitudinal cohort of mice undergoing serial 23-hour EEG recordings under three conditions was used in this study: first, baseline on a normal control diet; second, two days after starting a ketogenic diet (KD); and third, during an overnight fast. Mice were maintained on the control diet for eight weeks prior to the baseline EEG, and for three weeks in between KD and fasting EEGs. The control diet is based on AIN-93M, including 10% of calories from protein and 78% of calories from carbohydrates. The ketogenic diet contains 90% of calories from fat, and zero carbohydrates, but is otherwise matched to the control diet on a per-calorie basis. Diets were custom-synthesized to specifications by Harlan-Teklad (now Envigo). Caloric intake and blood BHB levels were stable within two days of switching to KD, and that KD and fasting produced similar 1-2 mM blood levels of BHB.

During the EEG recordings, mice were freely moving in one of four transparent plastic cylinders approximately the size of a home cage. Harmonie Stellate software was used for EEG recording and for automatically detecting sharp-wave spikes. Mice were also video-recorded during the EEG sessions, and Noldus Ethovision software was used to quantify movement. Raw movement data was cleansed to eliminate reflection or other artifacts prior to data analysis. Gamma activity, defined as power recorded by the EEG in the 20-80 Hz range, was quantified using LabChart software. Data analysis was performed using GraphPad Prism and custom-written Perl programs. The EEG, data recording, and data analysis methodology is described further in Verret et al., Cell 2012, 149:708-721.

Results

Figure 7A:
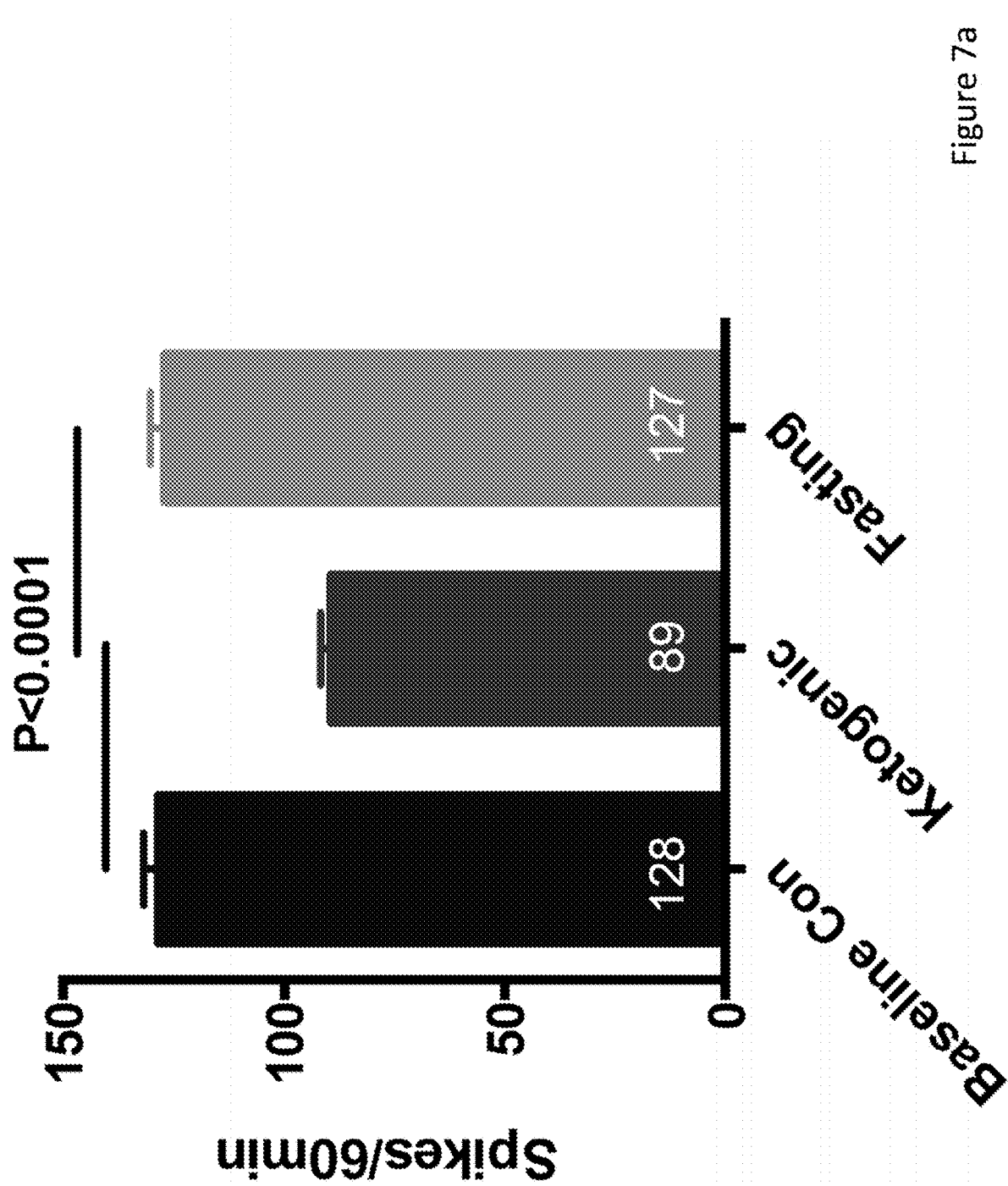
FIGS. 7a-7h demonstrate that ketogenic diet, but not fasting, consistently reduced epileptiform spikes in APPJ20 mice.
Figure 7B:
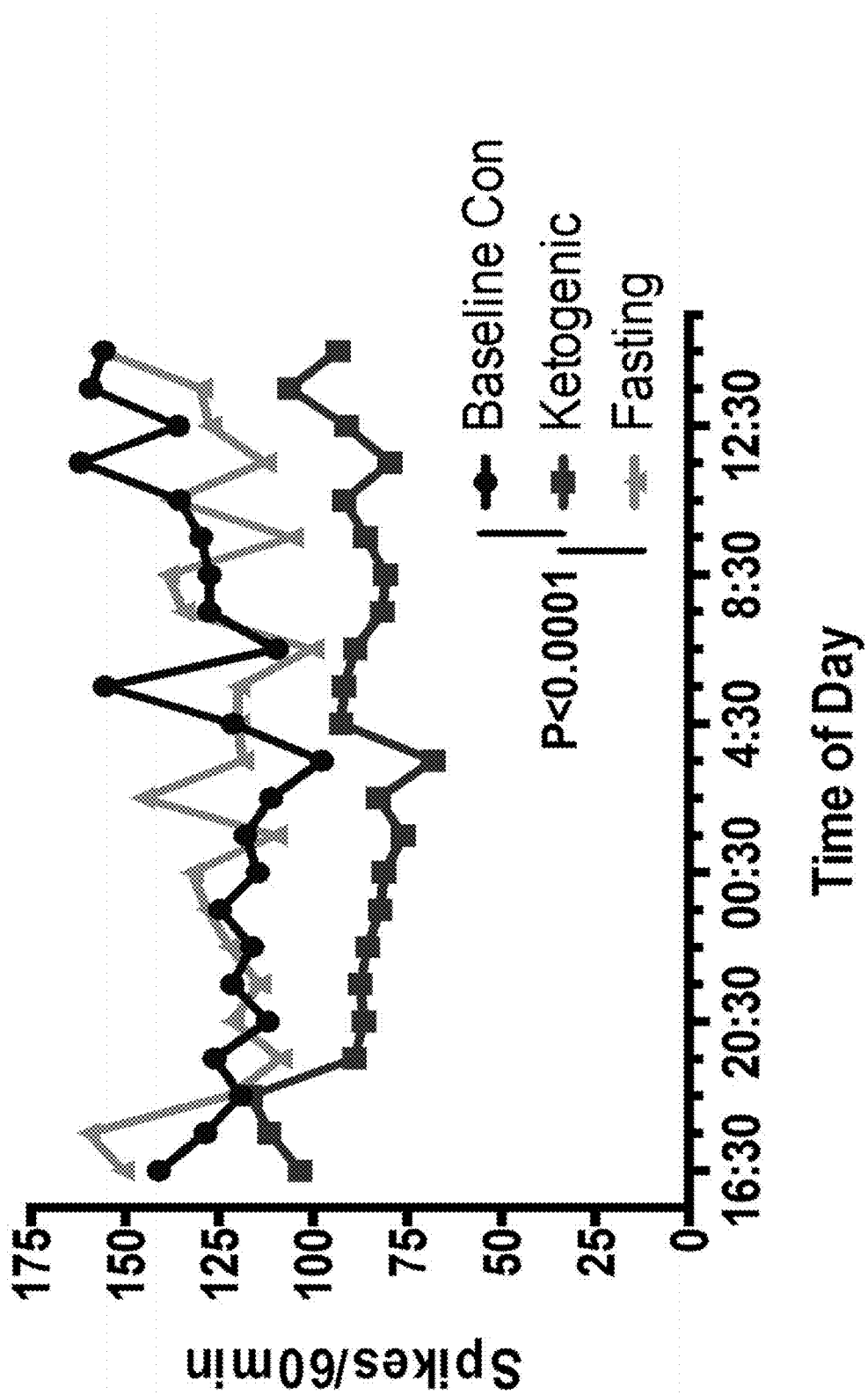
Figure 7C:
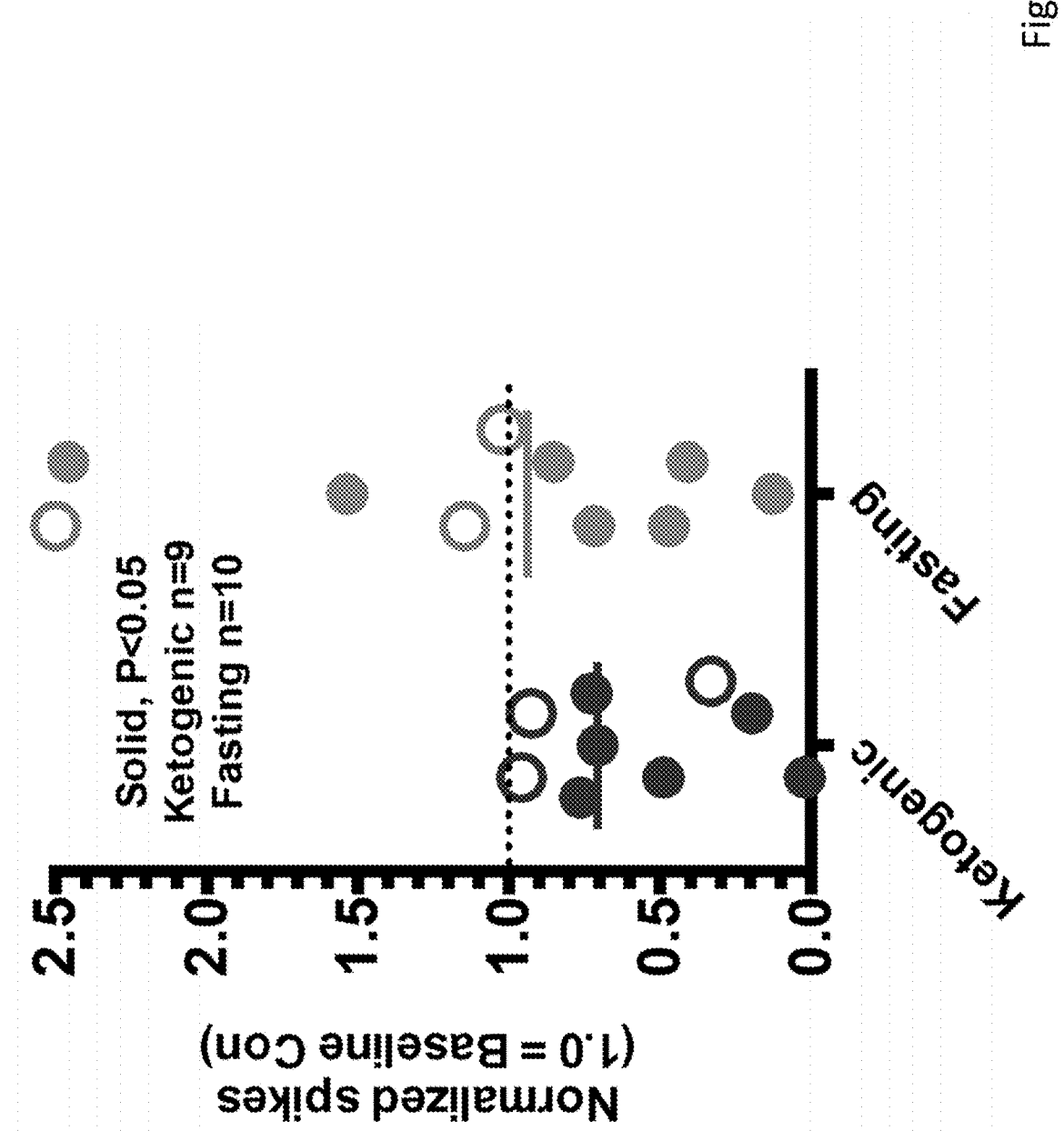
Figure 7D:
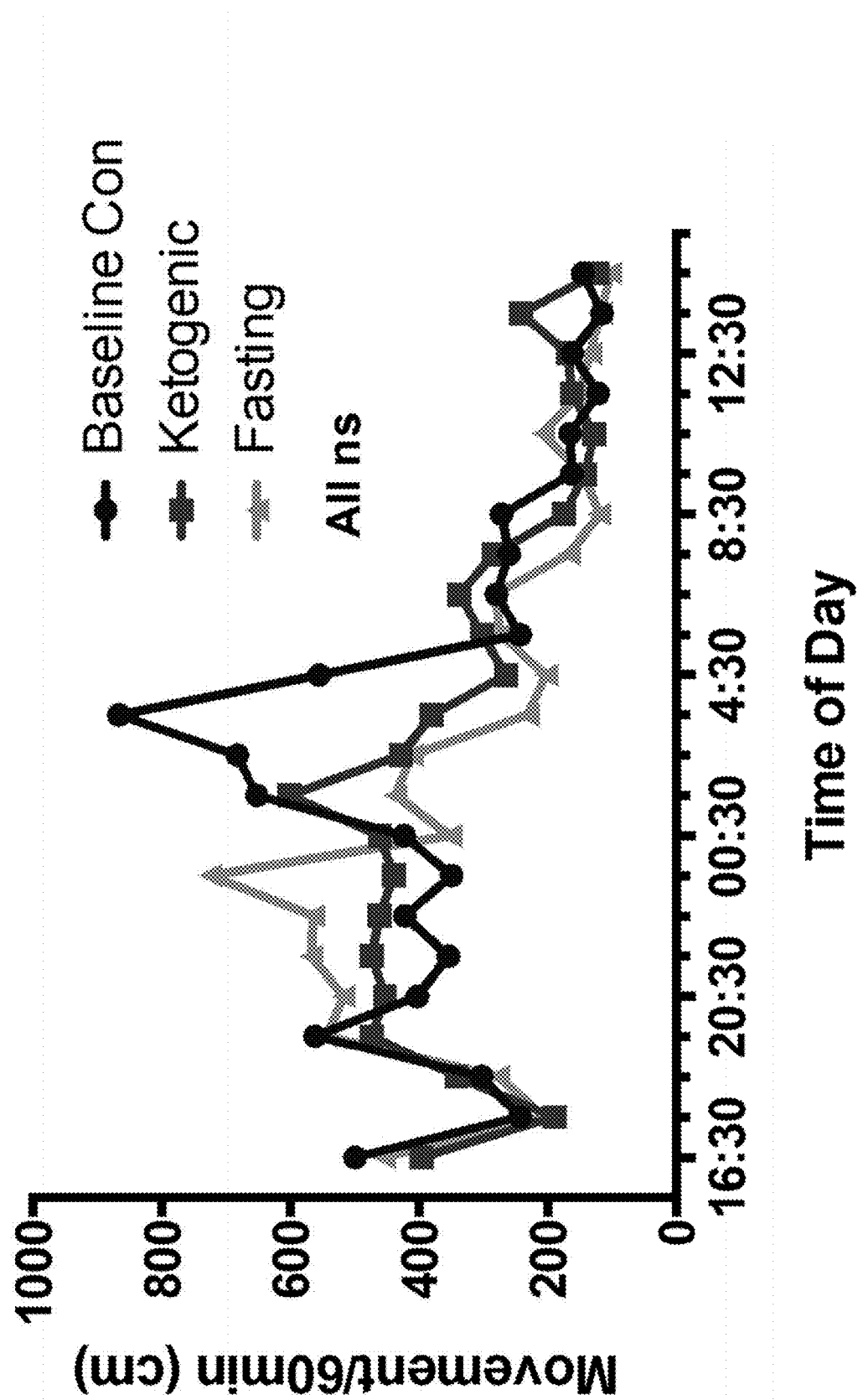

FIGS. 7a-7h demonstrate that a ketogenic diet, but not fasting, consistently reduced epileptiform spikes in APPJ20 mice. As shown in 7a, 23-hour EEG recorded 2 days after starting KD showed ~30% average spike reduction compared to prior baseline on a control diet, from 2.13 spikes/min to 1.48 spikes/min. Overnight fasted mice showed no change on average. FIG. 7b shows hourly spike totals during 23-hour EEG recordings, demonstrating that spike suppression was consistent throughout the 23-hour recordings. FIG. 7c shows spike reductions in individual mice, normalized to each mouse's baseline recording (filled circles, $P<0.05$; bar=median). 6 of 9 mice had an overall reduction in spikes on KD, with none increased over baseline. In contrast, although fasting reduced spikes in some mice it exacerbated them in others, resulting in no change on average.

Example 6—Spike Suppression by Ketogenic Diet is Independent of Interneuron Function Materials and Methods Ketogenic diet and overnight fasting were used to test the mechanism of epileptiform spike suppression by ketogenic diet in one-year-old APPJ20 mice. The longitudinal cohort of mice undergoing serial 23-hour EEG recordings was described in Example 5 above. The methodology for data acquisition and analysis was also described in Example 5 above. Movement data, gamma power data, and spike data were collated at one-minute intervals to explore the instantaneous relationships between exploratory movement, inhibitory interneuron gamma activity, and spikes.

Results

Figure 7E:
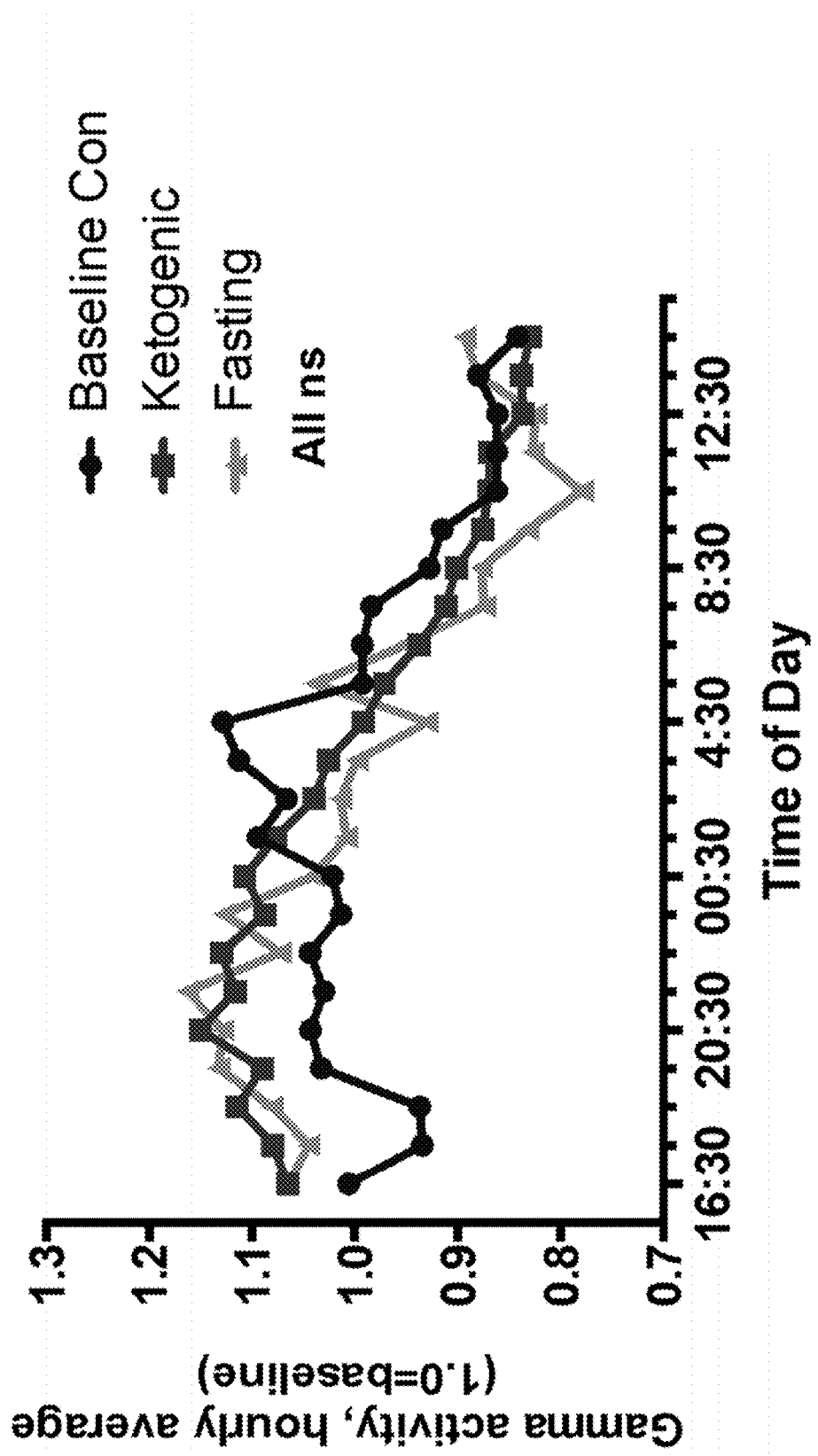
Figure 7F:
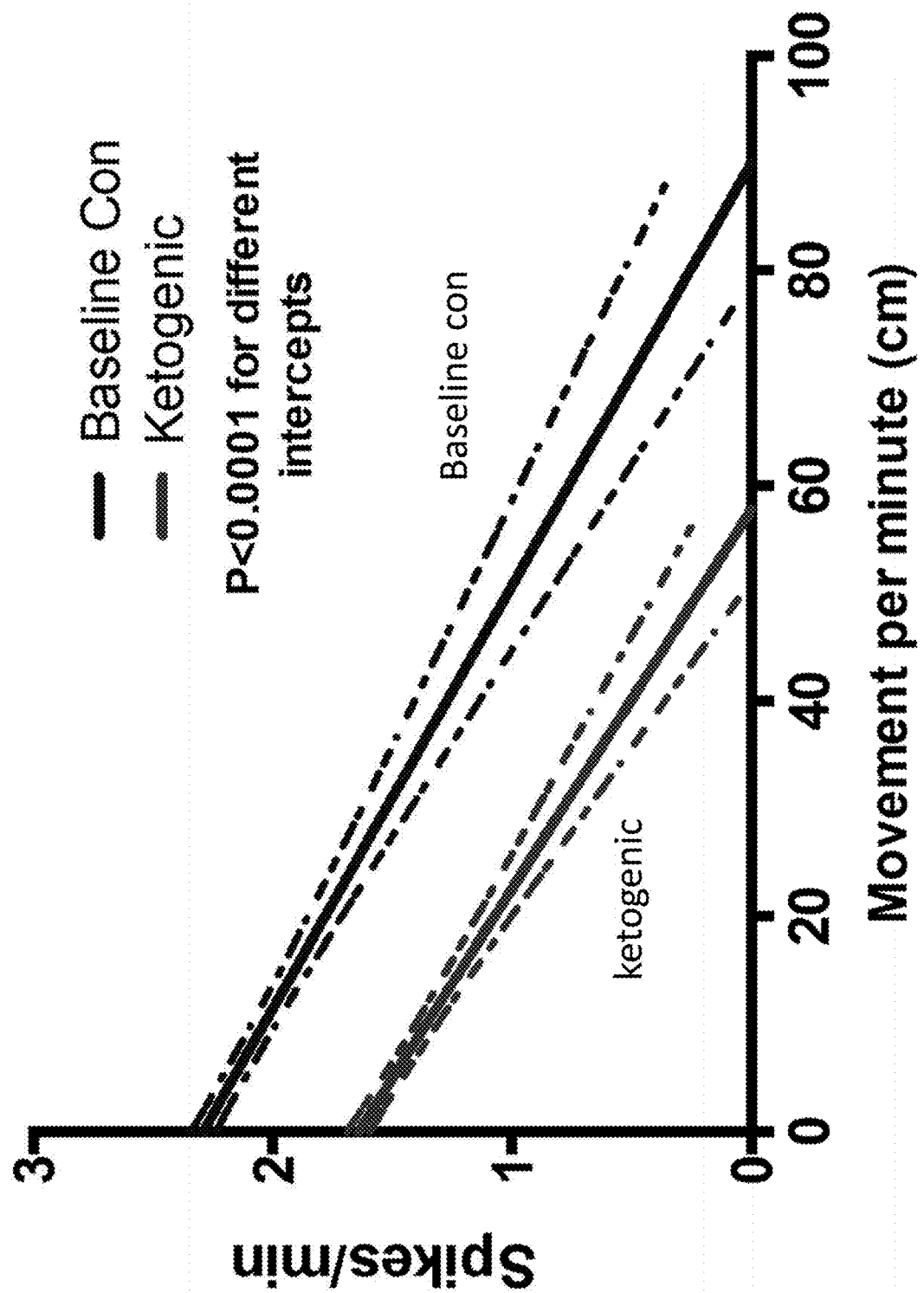
Figure 7G:
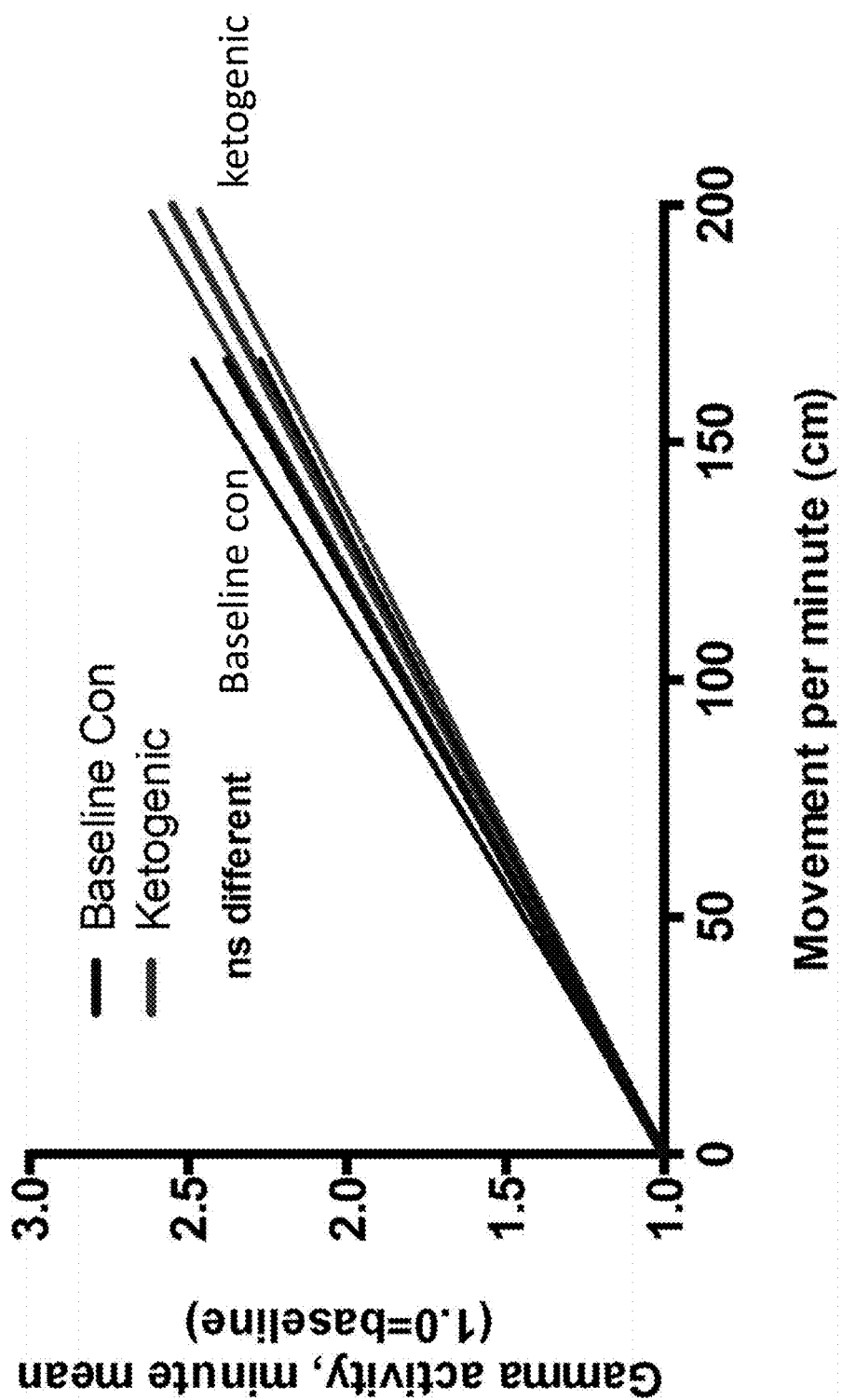
Figure 7H:
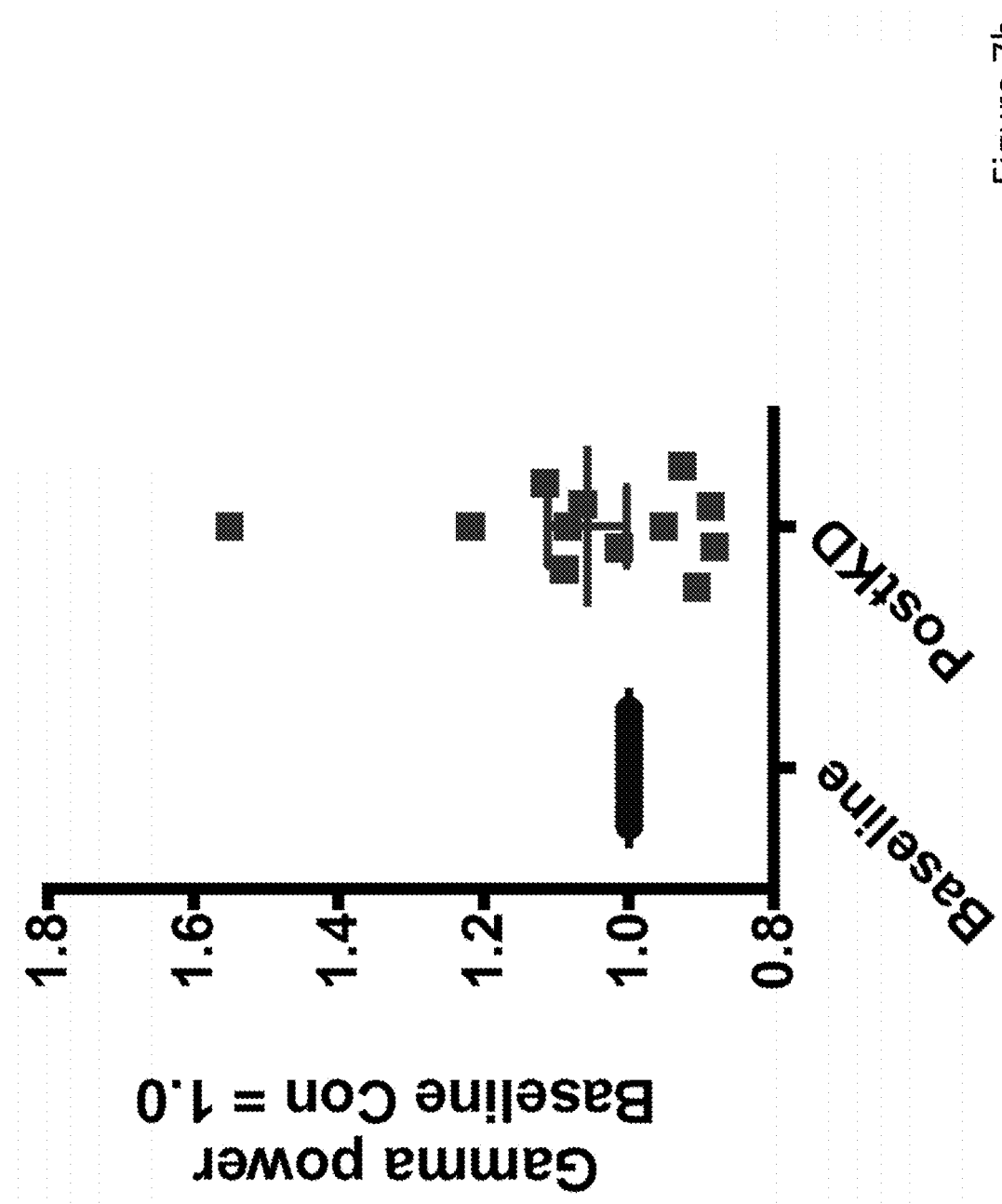

Exploratory movement is associated with suppression of epileptiform spikes via increased inhibitory gamma activity from parvalbumin-positive interneurons (Verret et al., Cell 2012, 149:708-721). Three possible mechanisms by which KD might suppress spikes could be via increased exploratory movement, exaggeration of the induction in gamma activity from a given level of exploratory movement, or increase in baseline gamma activity. Overall movement was similar in all three conditions (FIG. 7d), and so increased exploratory activity did not explain spike suppression from KD. Relative gamma activity was also similar between the three conditions (FIG. 7e). FIG. 7f provides best-fit linear regression lines with 95% CI for scatterplots of per-minute spikes and movement. APPJ20 mice normally have lower spikes with higher exploratory movement; KD was associated with spike suppression at all levels of movement (FIG. 7f). FIG. 7g provides best-fit linear regression lines with 95% CI for scatterplots of per-minute normalized gamma activity and movement showing no change in the rate of induction of gamma activity by movement on KD. In other words, the rate of increase of gamma activity with movement was similar between control diet and KD (FIG. 7g). Finally, the overall mean level of gamma activity was unchanged for most mice on KD, and was not associated with change in spikes (FIG. 7h). Altogether, KD appears to be acting either independently of parvalbumin-positive interneurons, or downstream of the presynaptic potentials that generate gamma activity in this neuronal population.

Example 7—Long Term Ketogenic Diet Reduces Spikes and Improves Cognition

Materials and Methods

Long-term sustainability of suppression of epileptiform spikes on KD and whether spike suppression was associated with cognitive improvement was determined as follows. Groups of one-year-old APPJ20 mice (these mice are described in Example 5) were placed on either control diet or KD (diets are described in Example 5) and followed for three months. They underwent seven 50-min EEG recording sessions in the later half of this period (EEG recording methodology is described in Example 5). In addition, they underwent habituation to the open field in the first month, while two of the EEG sessions two weeks and five weeks after habituation served as probes to test if familiarity with the open field from the prior habituation would reduce exploratory activity (FIG. 8a).

Habituation to the open field is a common test of visuospatial memory and cognitive function (Verret et al., Cell 2012, 149:708-721). Mice are placed in one of four identical transparent plastic chambers (40×40×30 cm) which contains two arrays of photobeams for measuring movement in the X and Y axis across the chamber floor; as well an additional pair of arrays elevated in the Z axis for detecting rearing behavior. The apparatus is controlled by Photobeam Activity System software from San Diego Instruments. A customized program performs processing of the raw beam break data. Movement data from the open field is integrated with spike and gamma power data from EEGs using customized programs. Normal mice show rapid habituation, in that their exploratory activity drops rapidly upon repeated exposure to the open field over days to weeks. APPJ20 mice show impaired habituation, in that exploratory activity remains elevated despite repeated exposure to the open field over days to weeks (Verret et al., Cell 2012, 149:708-721).

Results

Figure 8A:
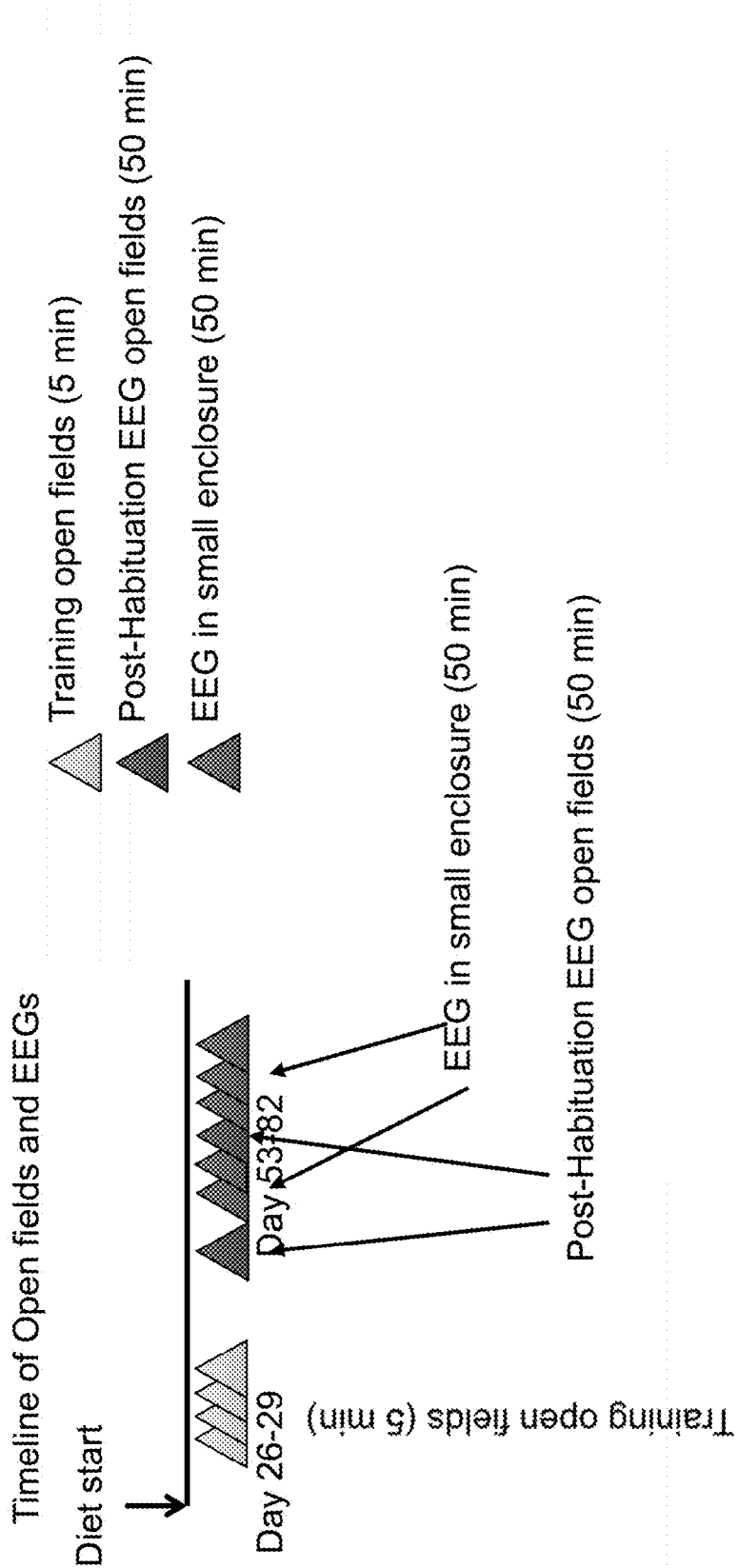
FIGS. 8a-8h depict the reduction in epileptiform spikes by KD continues for months, and is associated with cognitive improvement in habituation to the open field.
Figure 8B:
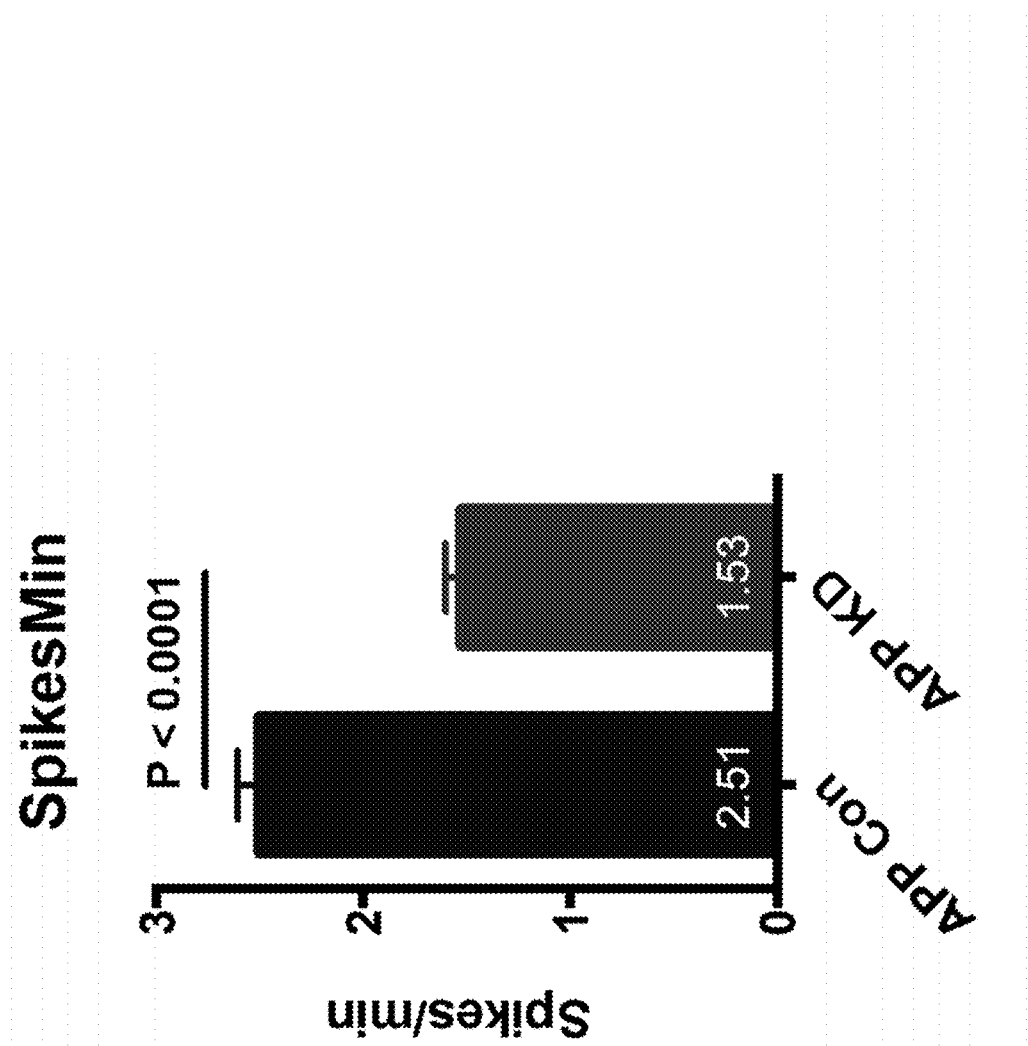
Figure 8C:
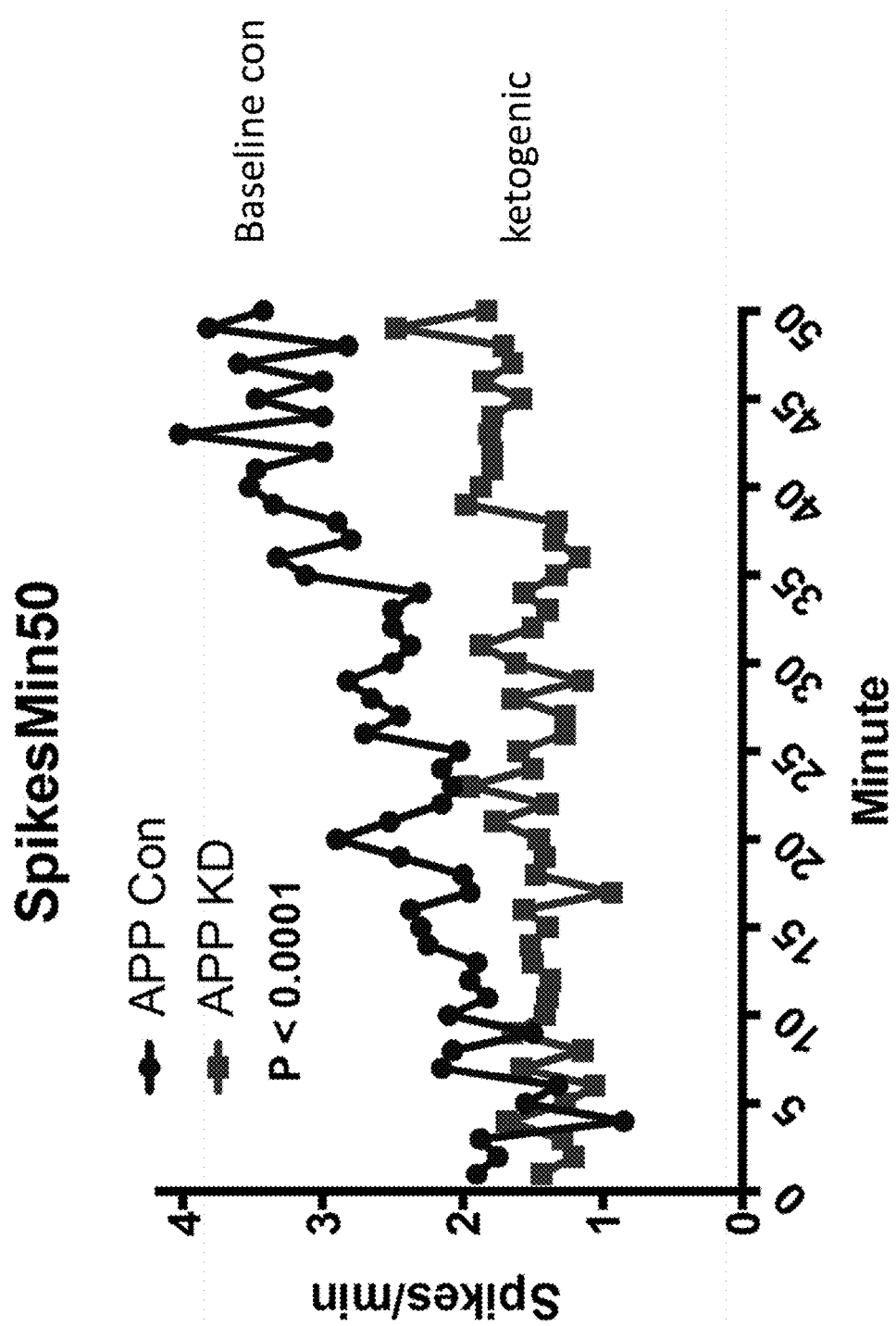
Figure 8D:
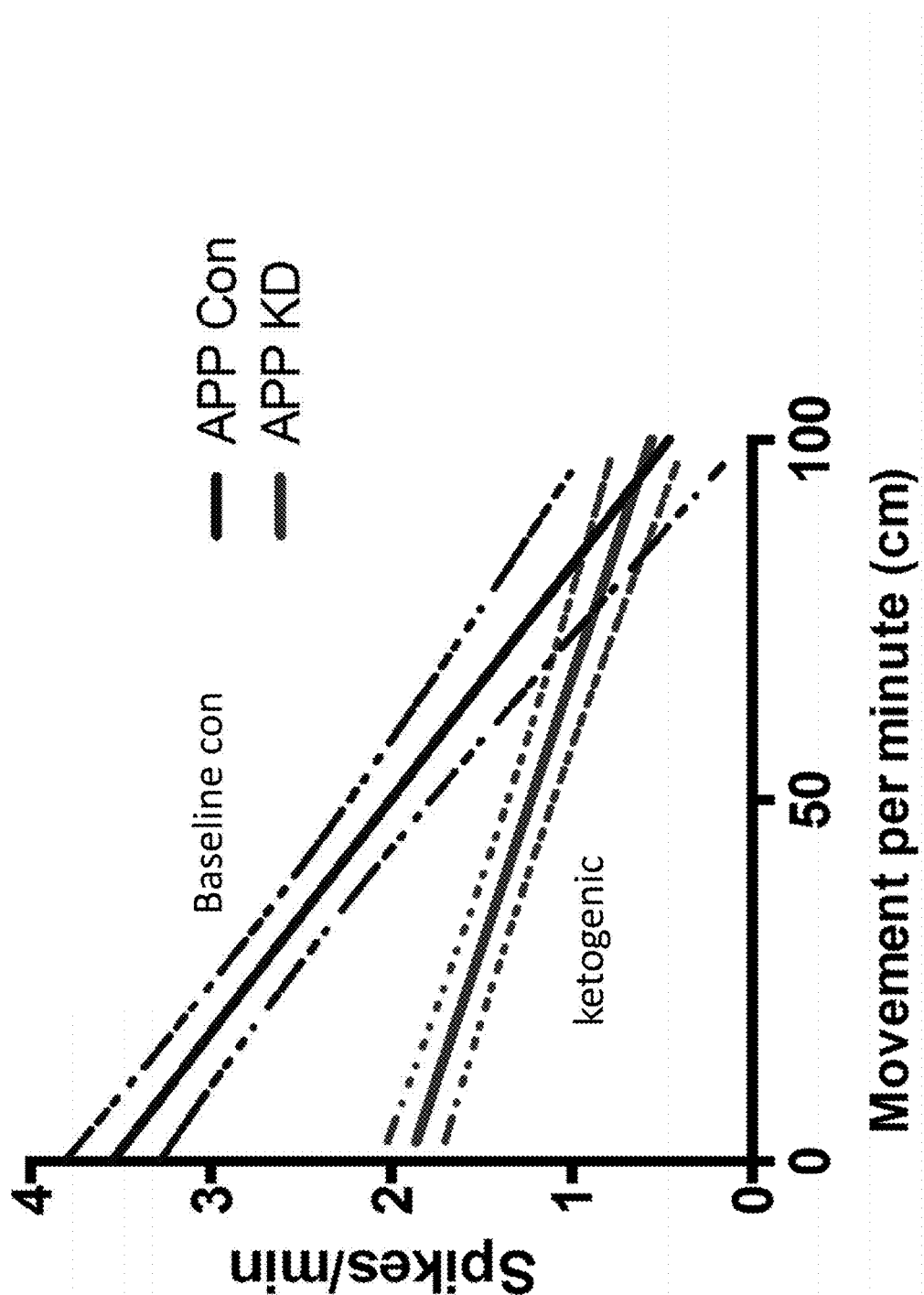
Figure 8E:
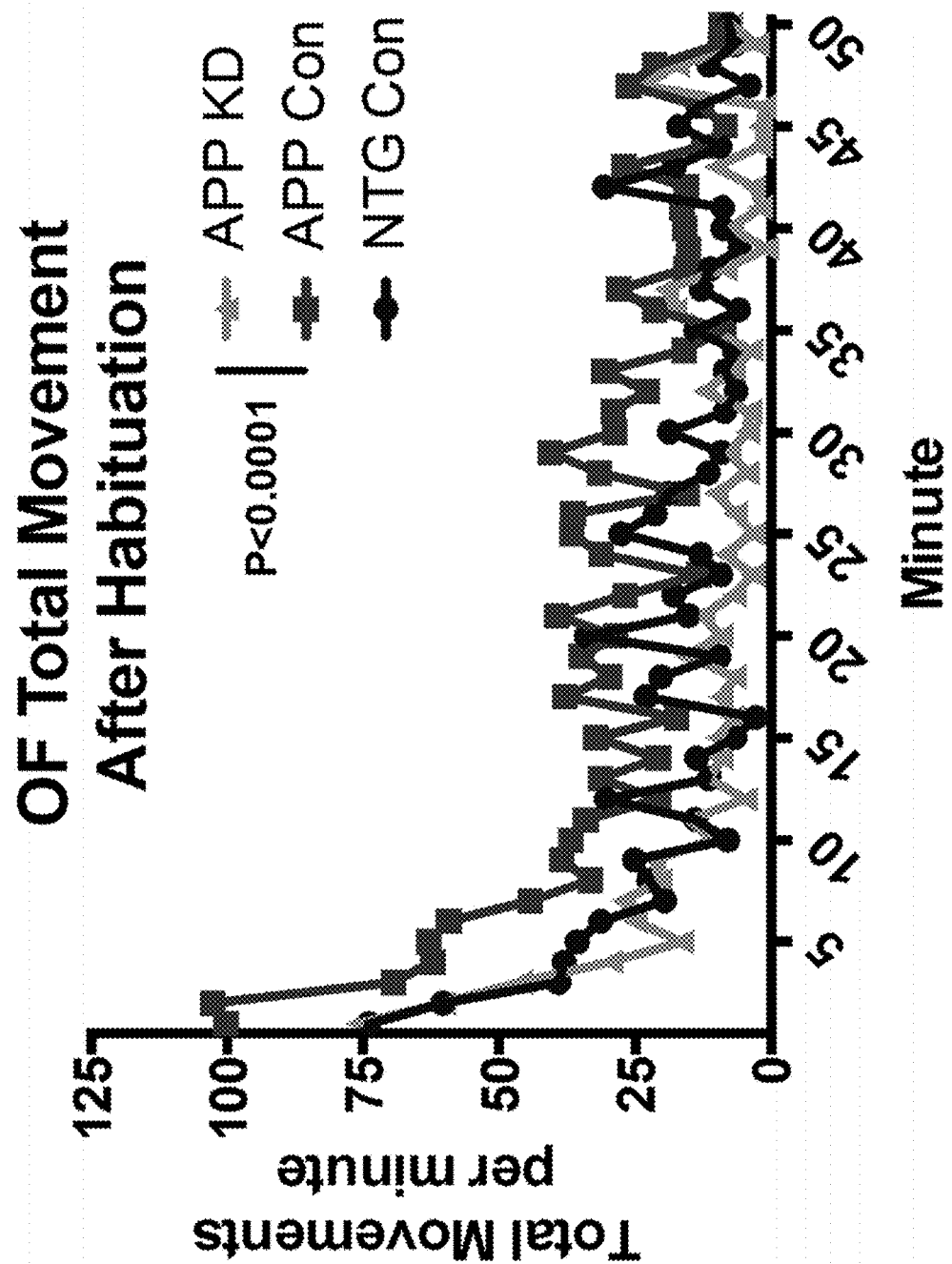
Figure 8F:
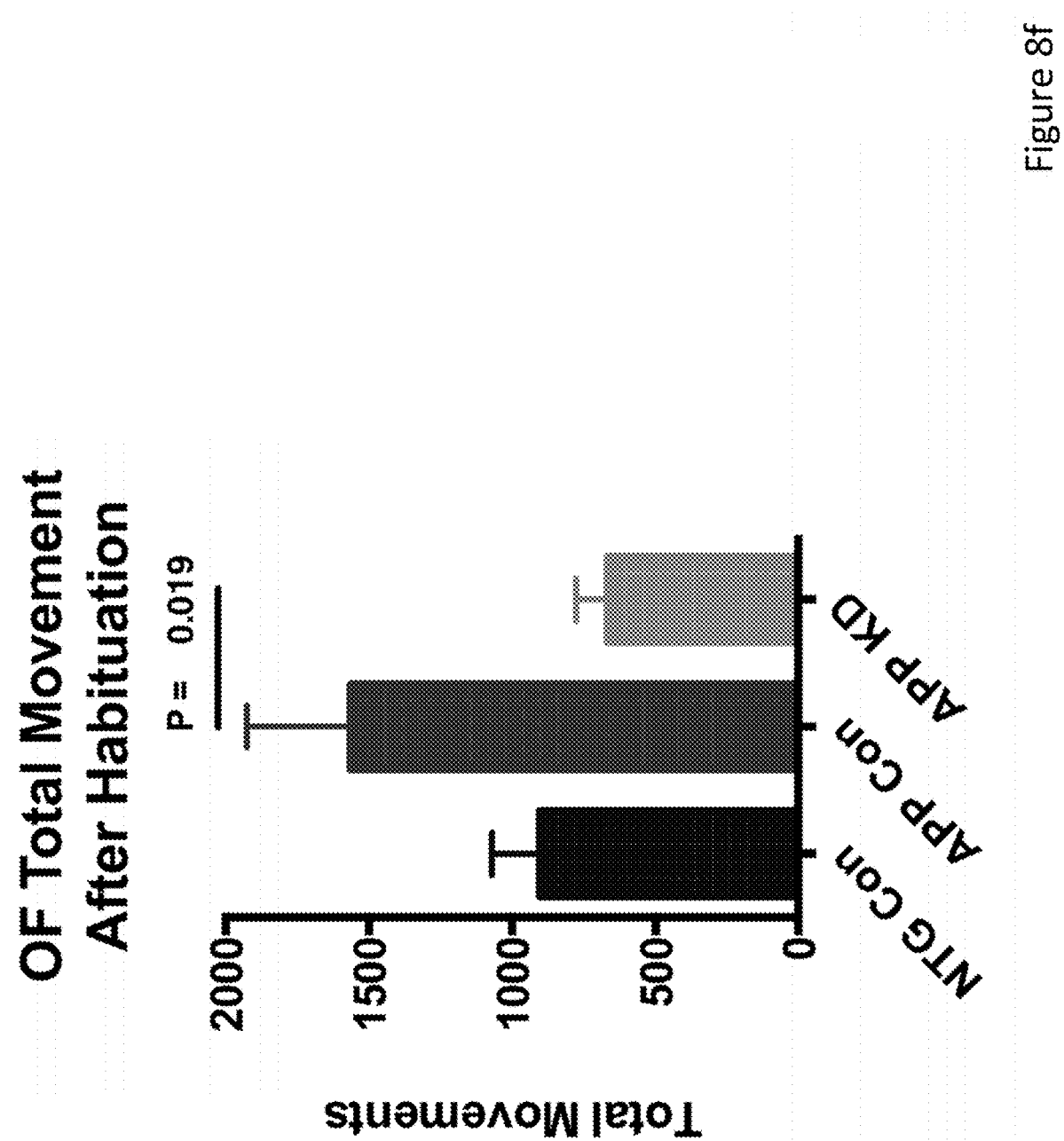
Figure 8G:
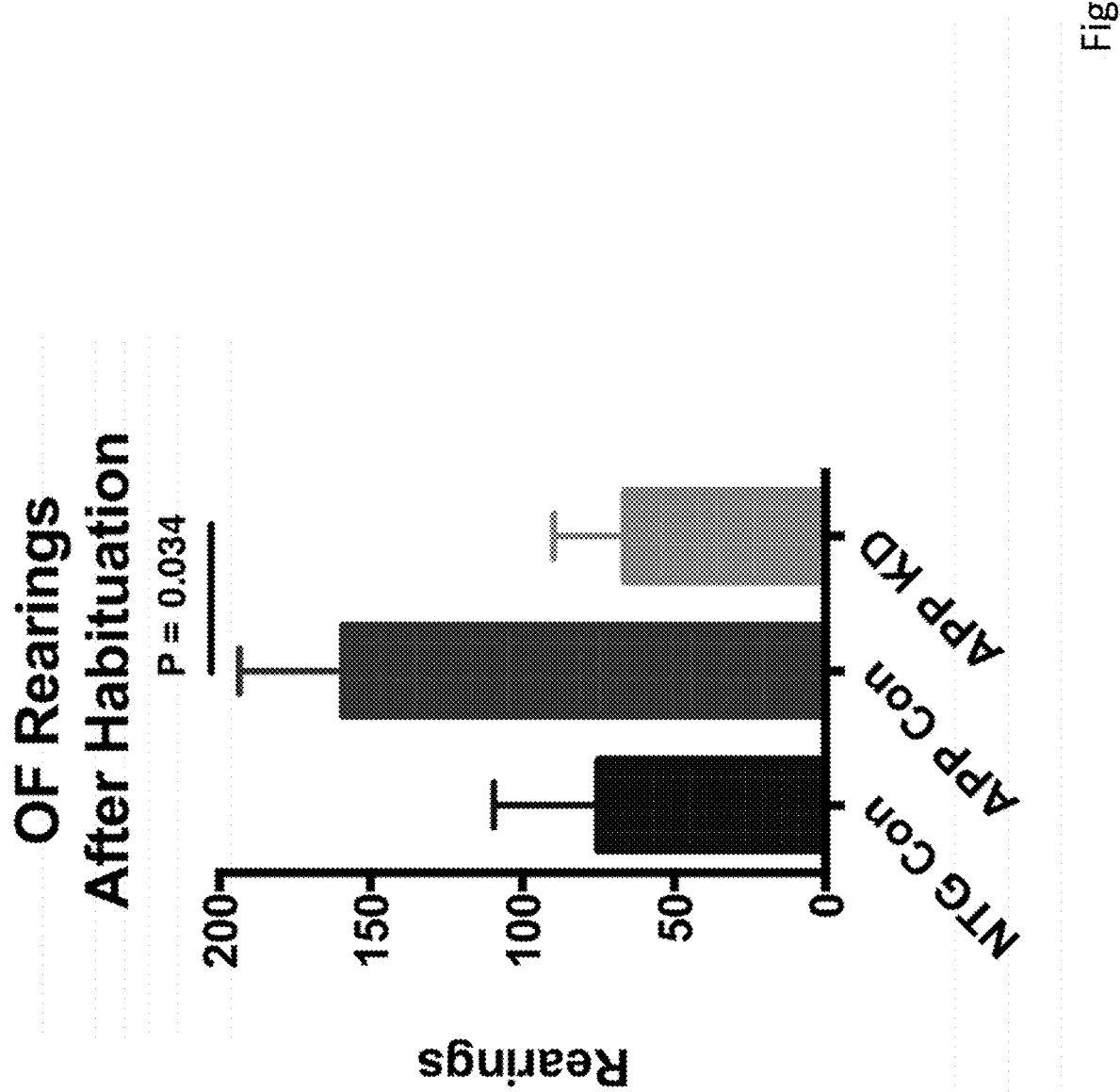
Figure 8H:
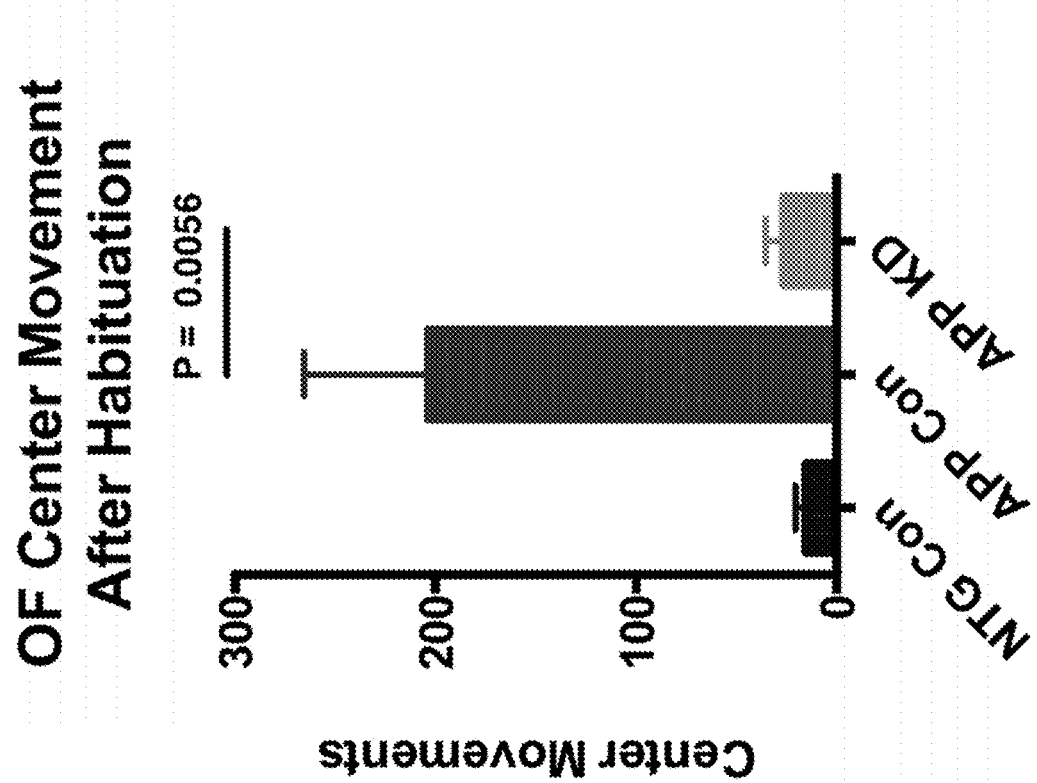

FIGS. 8a-8h show that the reduction in epileptiform spikes as a result of KD continues for months and is associated with cognitive improvement in habituation to the open field. FIG. 8a provides the experimental timeline. Having demonstrated that KD suppresses epileptiform spikes in the days following initiation of KD, this effect was evaluated to determine sustainability over weeks to months on the diet, and whether spikes suppression was associated with cognitive improvement. FIG. 8b shows that long-term KD consistently reduced epileptiform spikes over a three-month period by around 40%, from a mean of 2.51 spikes/min to 1.53 (FIG. 8b). FIGS. 8c and 8d show that spikes were consistently suppressed at all levels of movement (FIG. 8d) and throughout the 50-minute recordings (FIG. 8c), while mice on the control diet showed higher levels of spikes at periods of low movement later in the recording sessions. As predicted, APPJ20 mice on KD demonstrated reduced exploratory activity upon re-exposure to the open field after early habituation. Overall movement levels were similar to non-transgenic (wild-type) controls (FIGS. 8e and 8f), as were more specific exploratory movements such as movements through the center (as opposed to the periphery) of the open field (FIG. 8g) and rearings (FIG. 8h). APPJ20 transgenc mice on the control diet, by contrast, continued to exhibit hyperactivity and high levels of exploratory movements (FIGS. 8e-h).

The prior 23-hour EEG study was longitudinal (Example 5), with the same mice recorded on both control diet and KD, but this longer-term study by necessity maintained mice in separate diet groups. In order to confirm that individual variation in spike levels between APPJ20 mice did not explain the difference in epileptiform spikes between diet groups over days to weeks, a second longitudinal study was conducted. A group of mice was alternated from control diet to KD, obtaining four 50-minute EEG recordings on each diet. Again, mice showed significant suppression of epileptiform spikes while on KD, by over 50%, with the same abrogation of the relationship between exploratory activity and spikes seen previously.

Example 8—Chronic Ketogenic Diet is Associated with Obesity, Male Survival, and Improved Learning Materials and Methods Cognitive improvements, male survival and obesity from chronic ketogenic diet were tested in one-year-old APPJ20 mice.

This six-month study was conducted beginning with 2-month-old APPJ20 mice (mice are further described in Example 5) and littermate, non-transgenic (wild-type) control mice. The study answered three questions: 1) does KD fed long-term to mice have adverse metabolic effects such as obesity; 2) would KD reduce the early mortality commonly seen in APPJ20 mice, which is ameliorated by other treatments that suppress epileptiform spikes; and 3) would APPJ20 mice on KD show improvement in other visuospatial cognitive tests? Diet interventions are described in Example 5.

The Morris Water Maze is a common visuospatial memory test. The Maze consists of a shallow tub (122 cm diameter) filled with water made opaque with powered white paint. Large, high-contrast visual cues are placed on the walls of the room. Mice were habituated to the room and to the water pool the day before the experiment began. The experimental protocol consisted of six days of training (learning) trials followed by a probe (memory) trial 24 hours after the final training trial. During the training trials, a 14×14 cm platform was submerged just below the water surface. Repeated 60-second trials trained the mice to locate the hidden platform using visual cues from the room. The platform location was kept constant during training while the entry point of the mouse was changed semirandomly between trials. On the final day, the platform was removed for the probe trial. Mouse movement was monitored with Ethovision video tracking software (Nolus). Performance in the training trials is evaluated by how quickly mice locate the platform during each trial. Performance in the probe trial is evaluated by the proportion of time mice spend swimming in the correct quadrant of the pool, where the platform had previously been located. Following completion of this 7-day experimental protocol, the location of the platform was changed. Mice then underwent 3 days of "reverse training" to this new location, followed again by a probe trial with the platform removed 24 hours after the final training trial.

Results

Figure 9A:
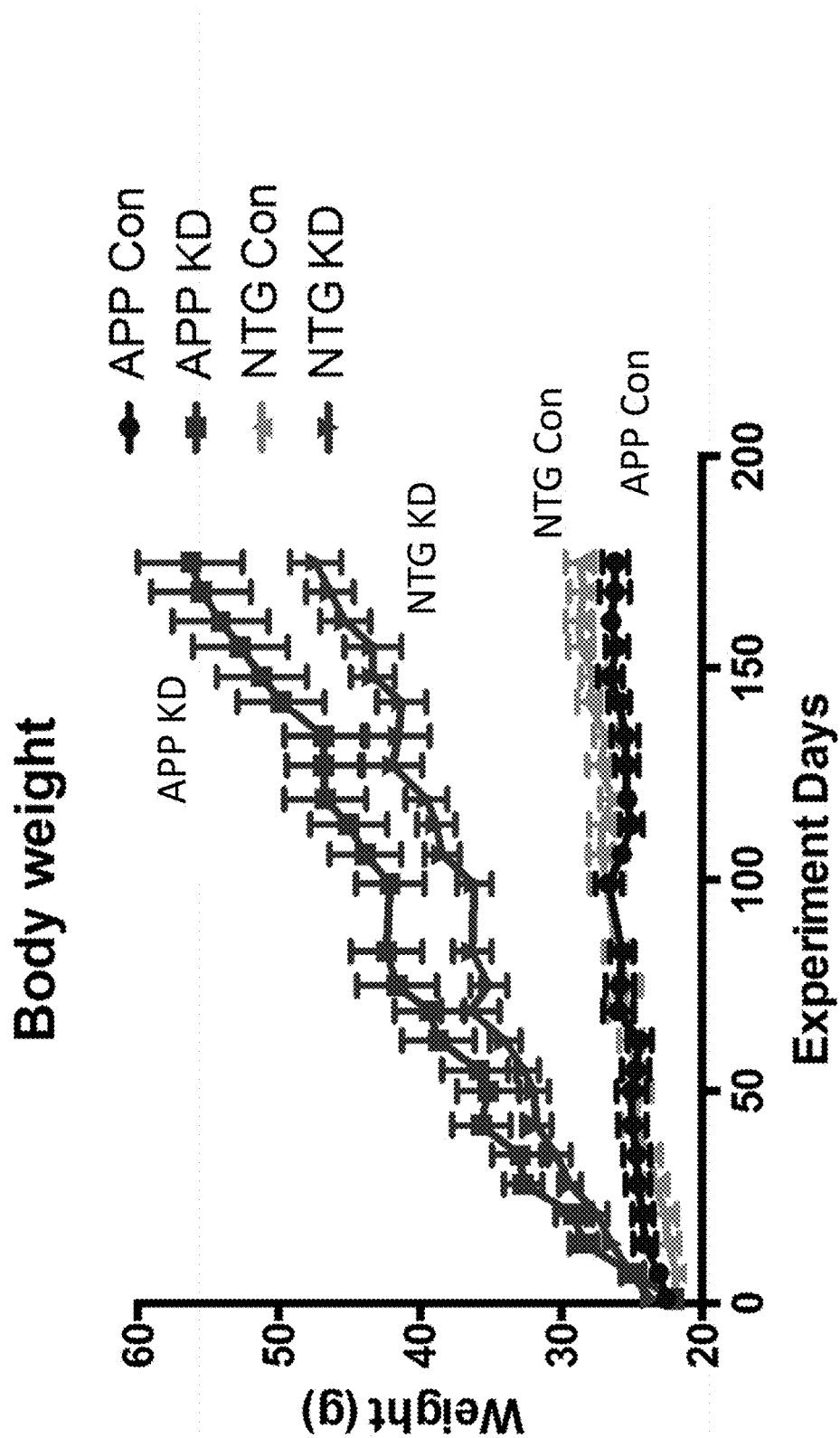
FIGS. 9a-9h demonstrate that long-term ketogenic diet improves cognition as well as, in males, survival.
Figure 9B:
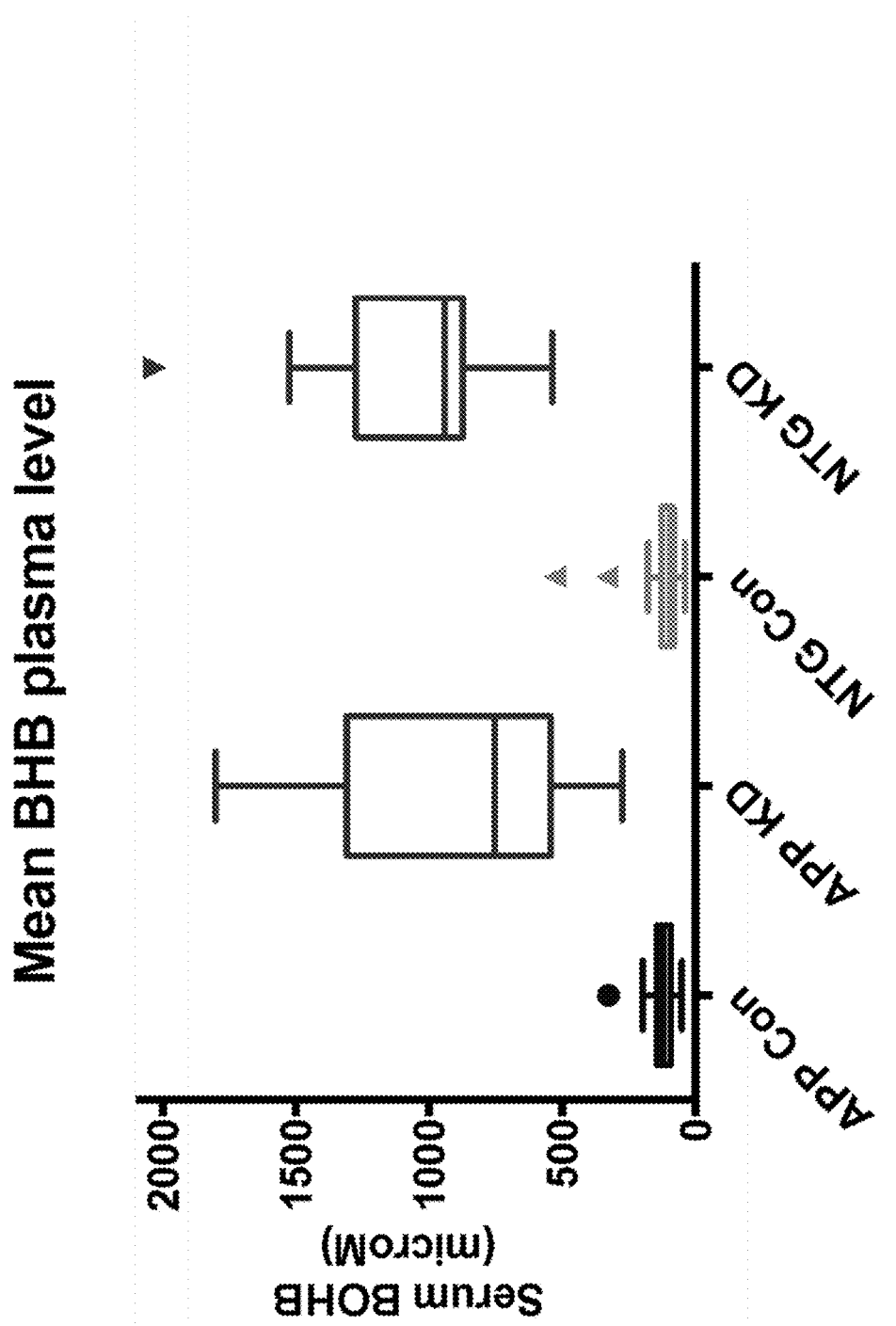

FIGS. 9a-9h demonstrate that long-term ketogenic diet improves cognition as well as, in males, survival. FIG. 9a shows the change in body weights for APPJ20 and NTG mice on either KD or control diet, started at 2 months of age. KD was substantially obesogenic for both APPJ20 and NTG mice, causing substantial weight gain. FIG. 9b shows the mean plasma BHB levels of six morning measurements taken about every two weeks from the start of the study. Both groups generated plasma BHB levels that averaged ~1 mM over the six-month period, generally higher early on. These levels were ~10-fold higher than mice on the control diet. Plasma glucose levels were similar in all groups. Males in all groups were heavier than females, and females had somewhat higher BHB levels on KD.

Figure 9C:
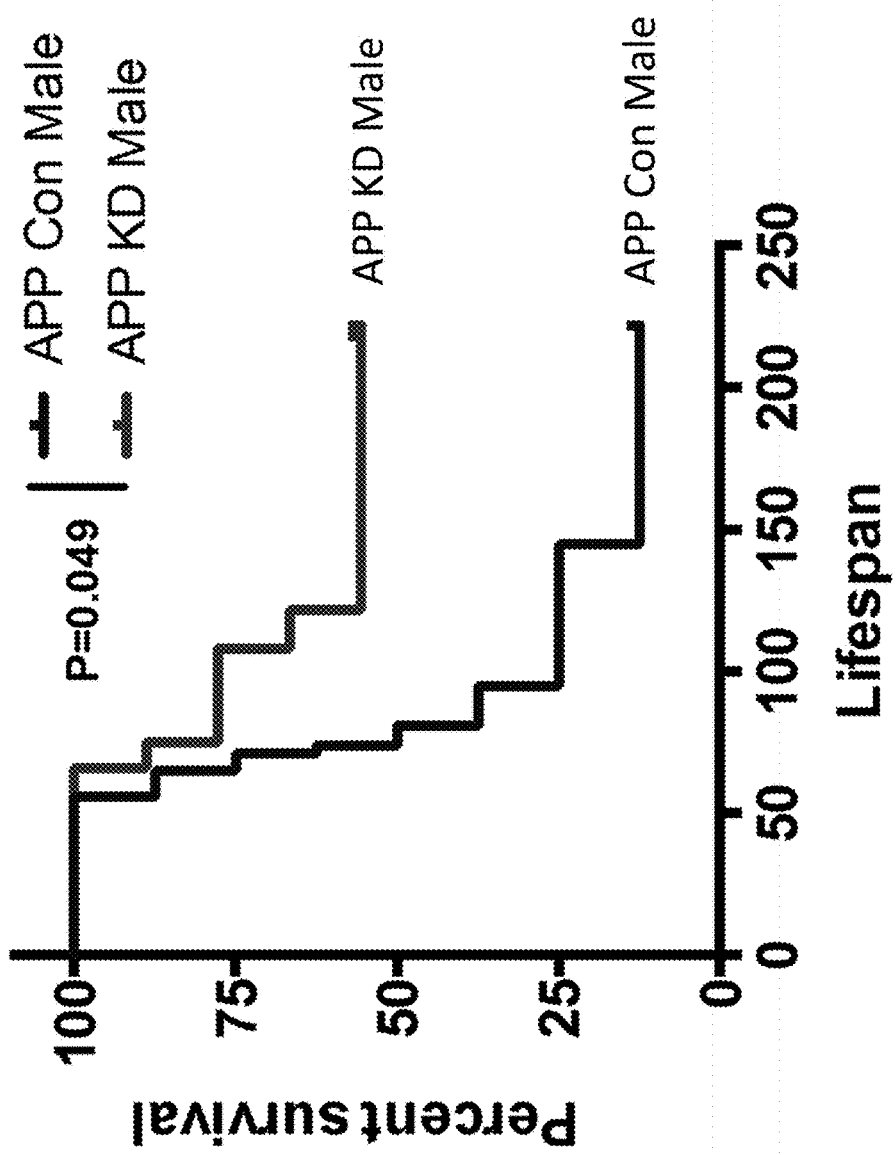
Figure 9D:
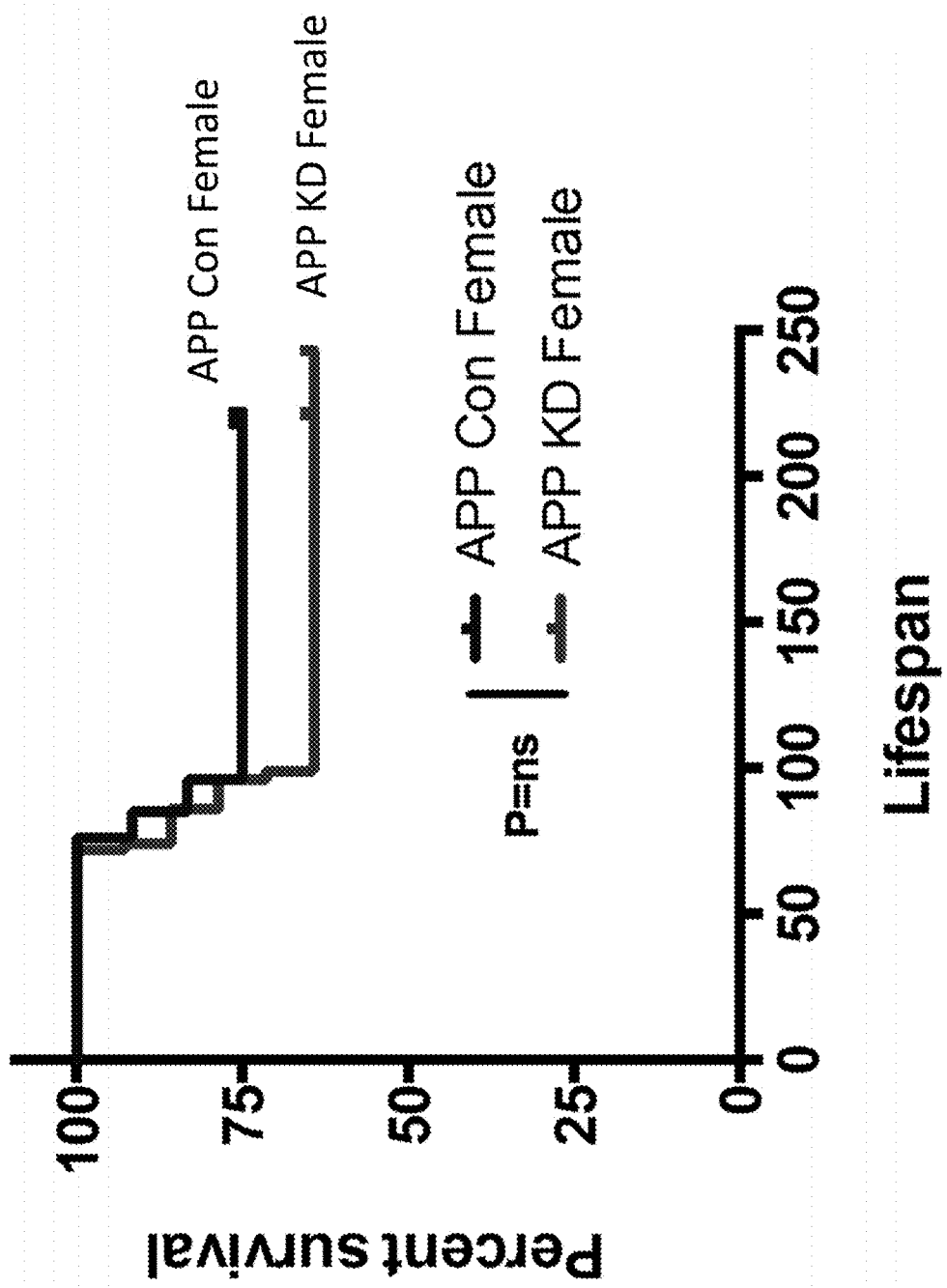

FIGS. 9c and 9d provide survival curves for APPJ20 male and female mice on KD vs. control diet. There were no deaths among NTG mice. APPJ20 mice have an early mortality as high as 40% that is thought to be due to fatal seizures. A trend towards reduced mortality was determined, and stratification by sex revealed it to be due to a significant reduction in the more severe mortality of male mice; female survival, already high, was not affected (FIGS. 9c and 9d).

Figure 9E:
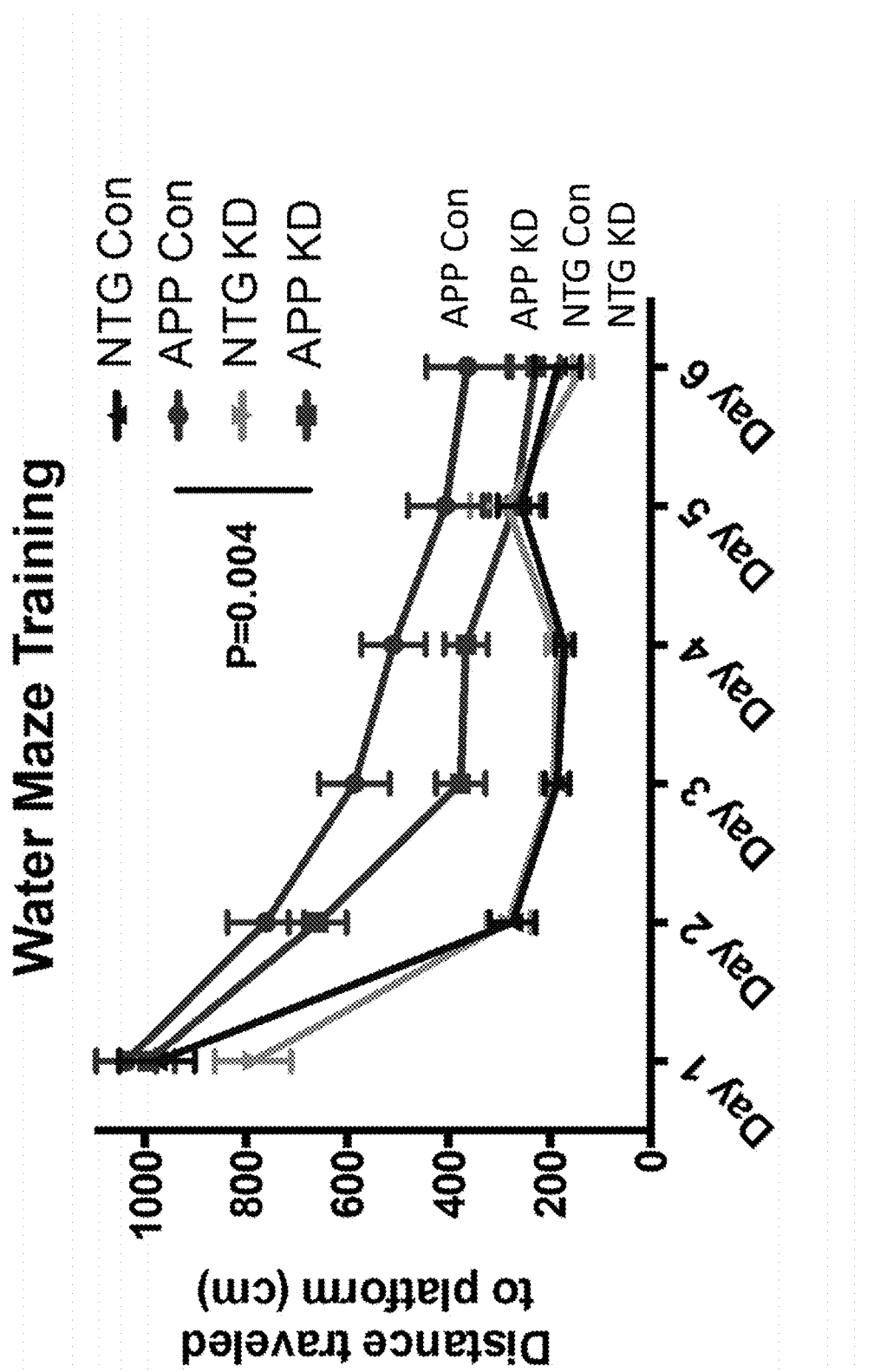
Figure 9F:
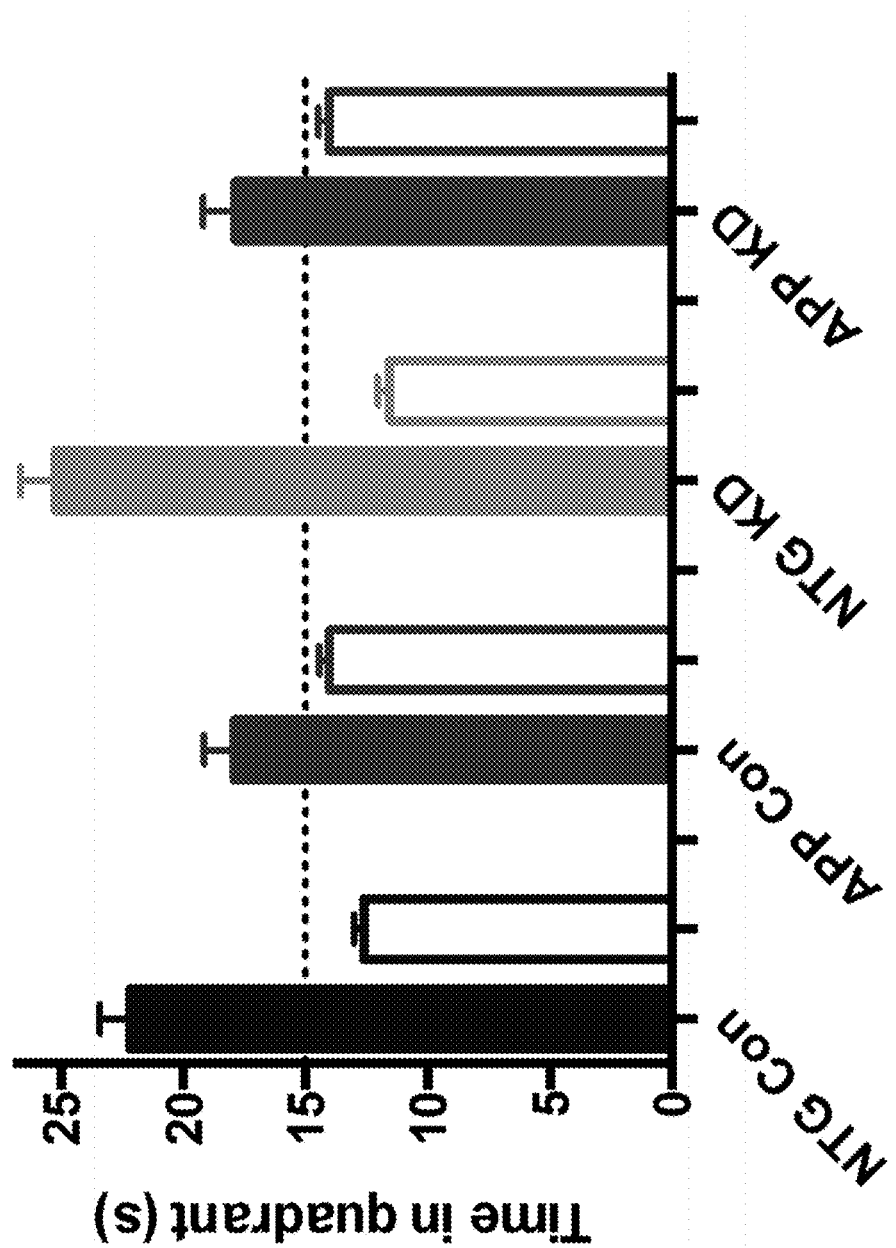
Figure 9G:
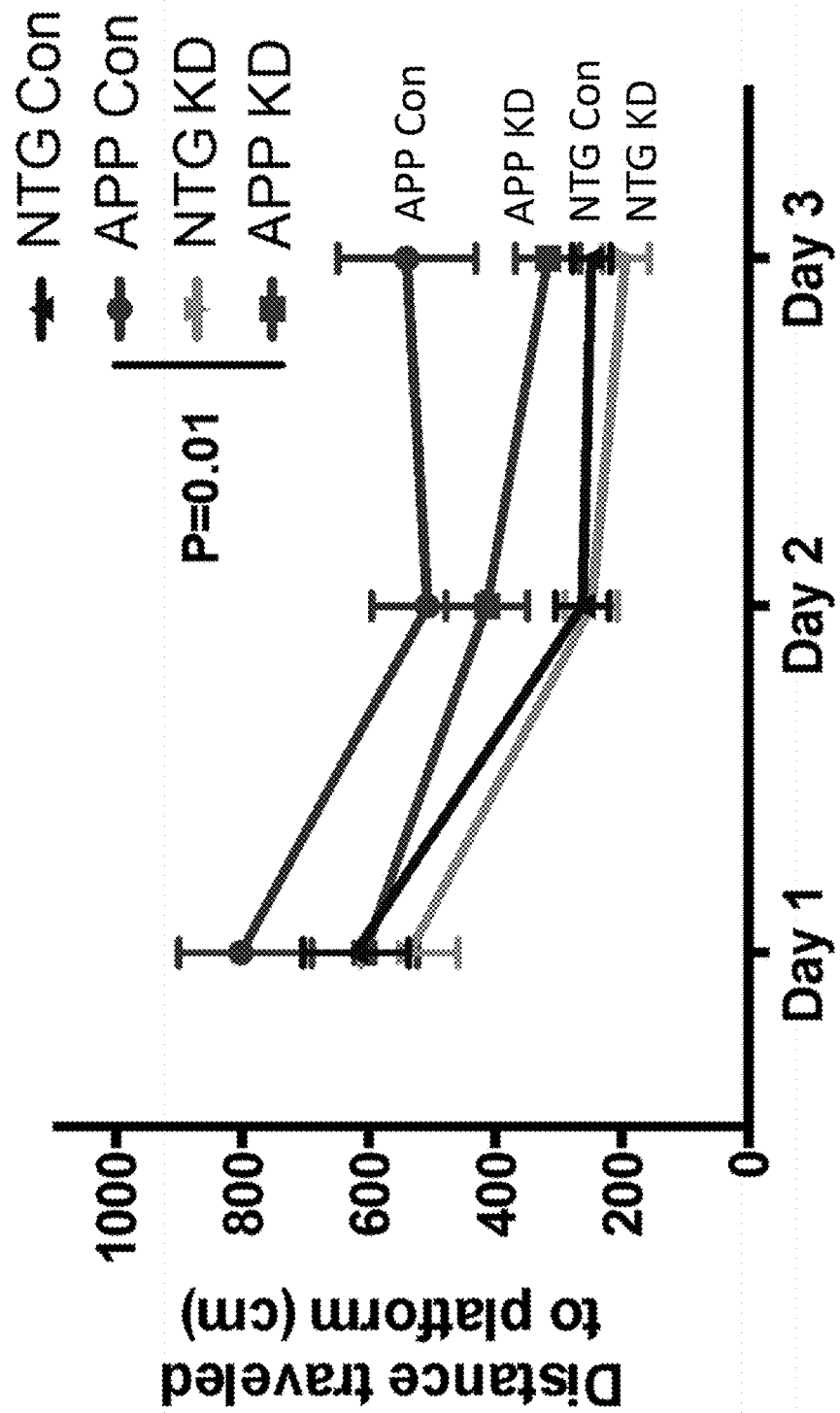
Figure 9H:
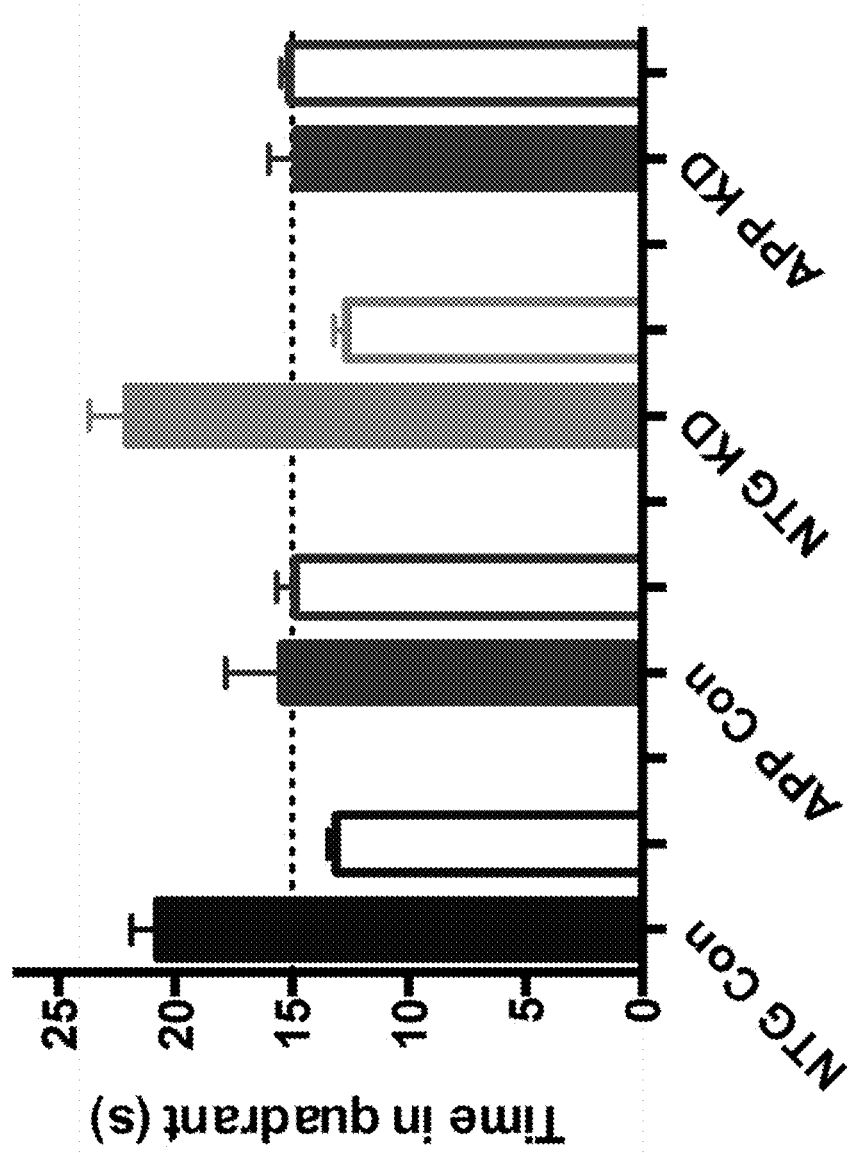

FIGS. 9e-9h show the results of Morris water maze testing performed three months after the start of the diets, when the survivors were 5 months old. APP mice on KD showed significantly improved performance in the hidden-platform training (learning) phase of the water maze (FIG. 9e). This improvement remained consistent when the location of the platform was moved (reverse training, FIG. 9g). However, there was no difference in performance during the probe/memory phase of the water maze, either following initial hidden platform training or after reverse training (FIGS. 9f and 9h).

Example 9—Ketogenic Compounds Suppress Spikes on Normal Diet

Materials and Methods

C6 and C8 esters of butanediol and C6 and C8 esters of β-hydroxybutyrate were synthesized as described above. The C6 ester of β-hydroxybutyrate was tested for efficacy in suppressing spikes in APPJ20 mice by intraperitoneal injection into 1-2 year-old APPJ20 mice including both male and female mice. The APPJ20 mice were described in Example 5.

EEGs were recorded from APPJ20 mice before and after intraperitoneal injection of C6-BHB, or an equivalent volume of saline. Following completion of the first 50 min recording, the injection was performed. Mice were then allowed to recover for 20 minutes in their home cage, followed by the second 50 min EEG recording. Blood was drawn immediately following completion of the second EEG session in order to measure plasma BHB levels (as described in Example 4). The lower of the two previously tested doses from Example 4 was injected, 50 µL per 30 g body weight, which is approximately 1.5 g/kg and approximately 0.2 millimoles.

During the EEG recordings, mice were freely moving in a transparent cylinder approximately the size of a home cage. Methodology for recording and analysis of EEGs and video tracking for movement was described in Example 5. Methodology for blood draws and plasma BHB measurement was described in Example 4.

The study used a cross-over design where all mice were injected with both C6-BHB and normal saline on different days, with at least 48 hours between injections. Data analysis was limited to mice that completed all injections and EEG recordings.

Results

Figure 10A:
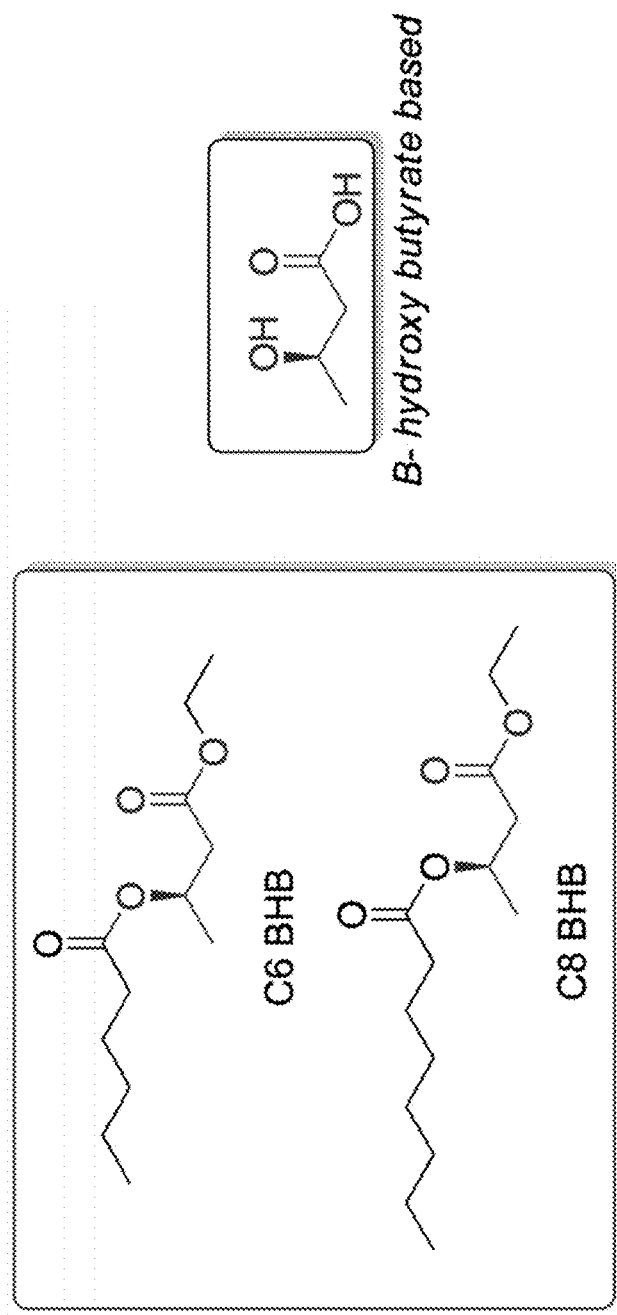
Figure 10C:
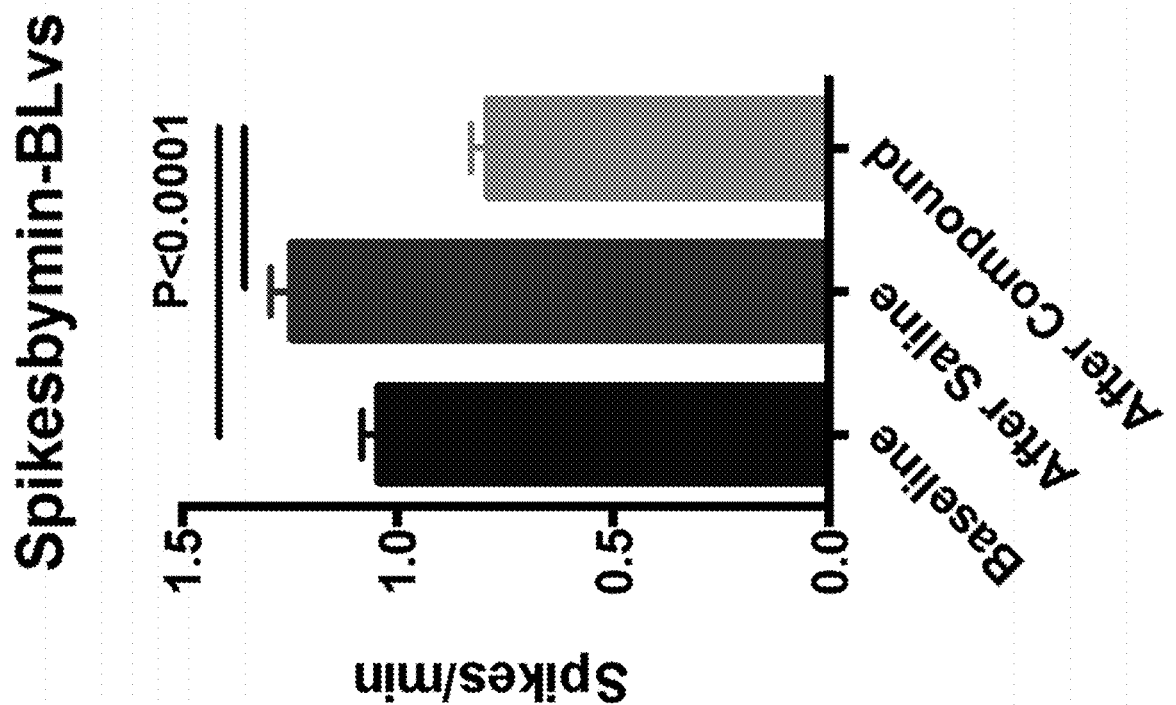
Figure 10D:
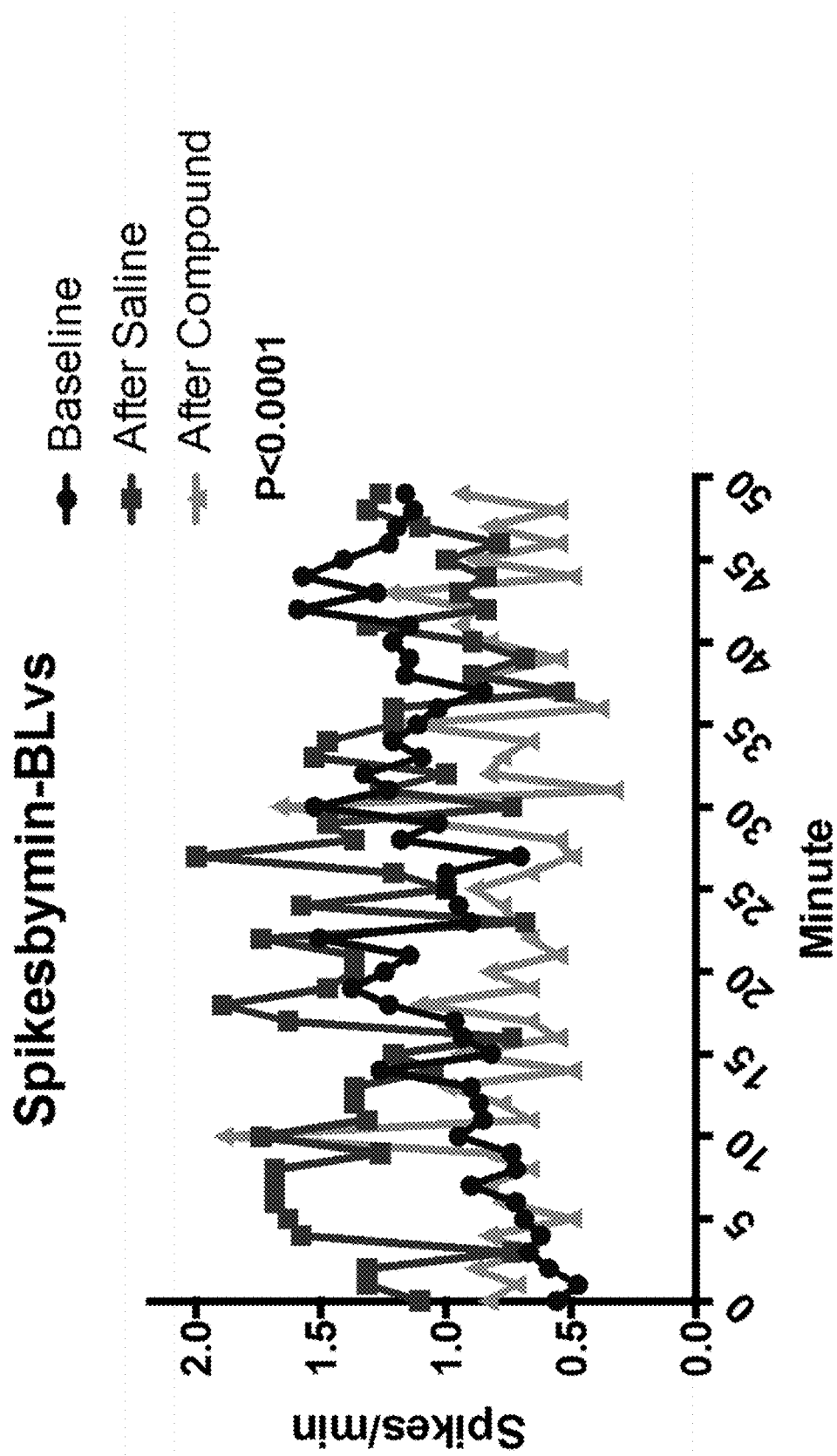
Figure 10E:
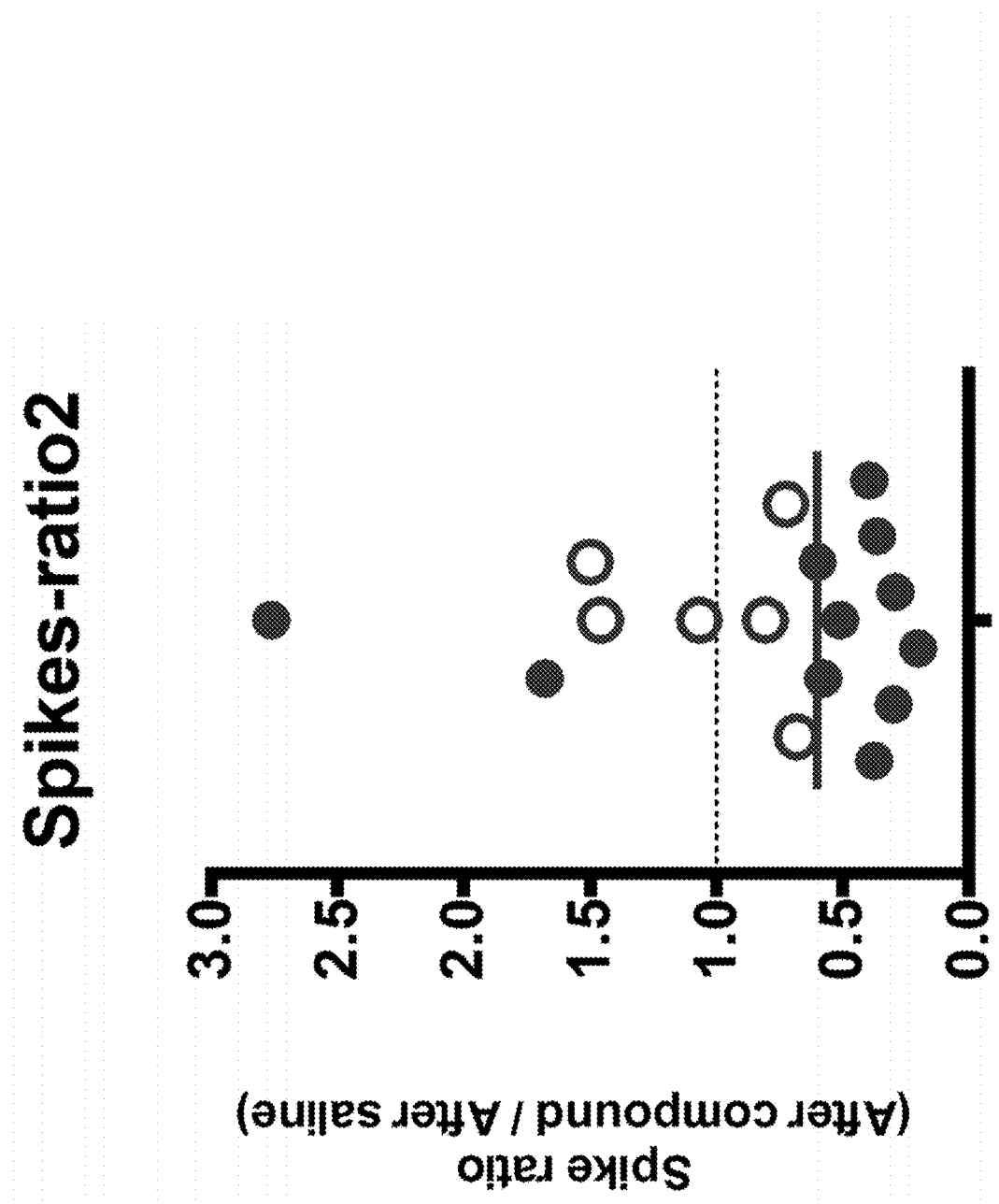
Figure 10F:
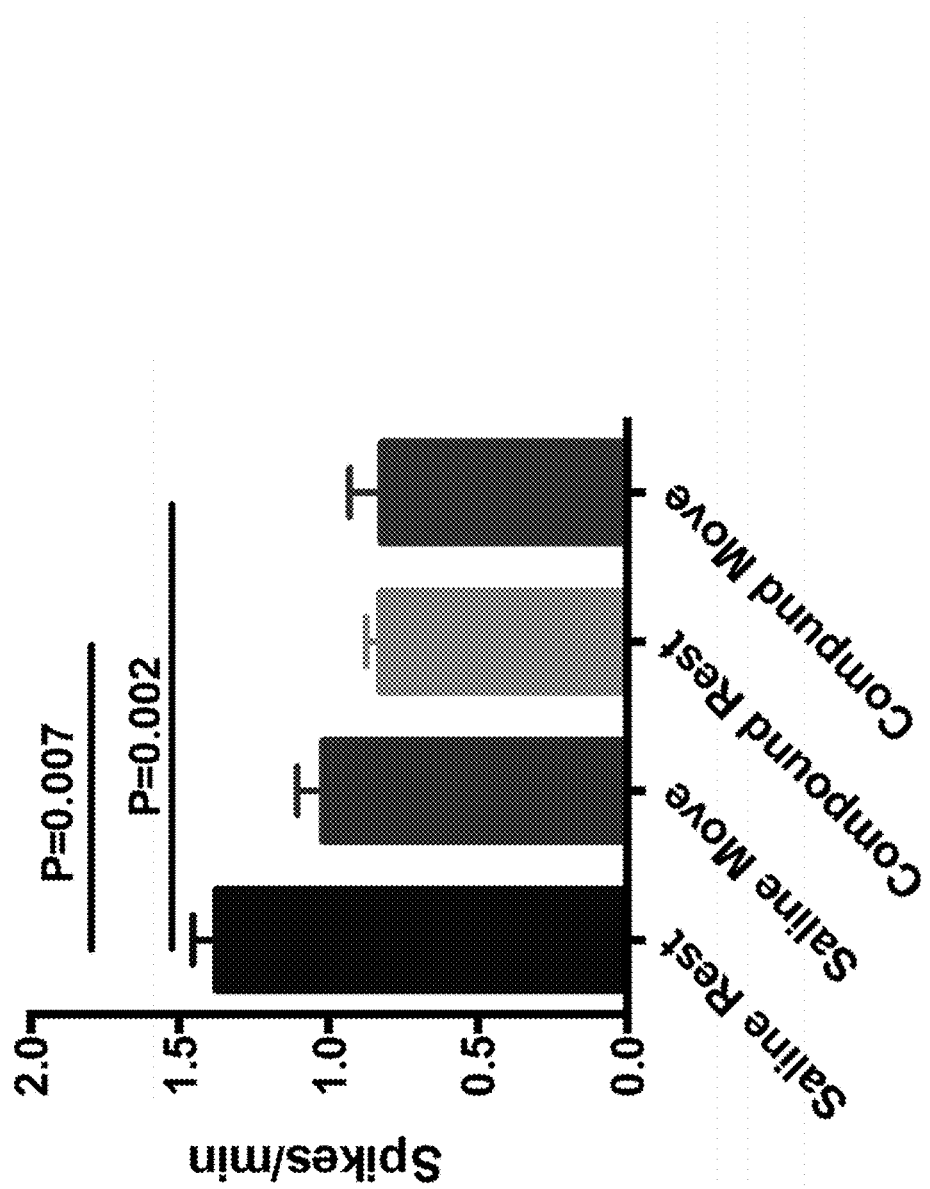

FIGS. 10a-10f demonstrate that compounds described herein that are metabolized to BHB immediately reduce epileptiform spikes. FIG. 10a provides a schematic of example ketogenic compounds having a medium-chain fatty acid ester-linked to BHB. FIG. 10b shows that injection of C6-BHB increased blood BHB levels, measured approximately 70-80 minutes after injection (following EEG). Injection of C6-BHB increased plasma BHB levels from a median of approximately 200 µM to a median of approximately 600 µM. FIG. 10c shows that injection of C6-BHB reduces spikes compared to both pre-injection baselines and injection of saline. A plot of average spikes over the 50-minute EEG recording (FIG. 10d) shows consistent reduction after C6-BHB injection, similar to KD. C6-BHB reduced epileptiform spikes by approximately 35% compared to saline injection, from 1.25 spikes/min to 0.82 spikes/min Analysis of spike reduction after C6-BHB, compared to after saline, at the individual mouse level shows significant reductions for most mice (filled circles, $P<0.05$; bar=median) (FIG. 10e). The difference in spikes between C6-BHB and saline injection was most pronounced when mice were at rest (and gamma activity is lowest), similar to KD (FIG. 10f).

Summary of Results of Examples 6-9

Disruption of normal network activity and associated epileptiform spikes from dysfunctional inhibitory interneurons are important for the pathogenesis of cognitive decline in Alzheimer's disease mouse models. Treatments that reduce epileptiform spikes improve cognition in these models. Ketogenic diet and fasting has been used to treat certain forms of epilepsy, including those mechanistically related to disrupted network activity in Alzheimer's models. For example, reduced expression of the sodium channel subunit SCN1A was found to be a key mechanism leading to early mortality, epileptiform spikes, and cognitive impairment in APPJ20 mice, and restoration of normal expression improved these deficits (Verret et al., 2012). There is a group of human genetic seizure disorders due to mutations in SCN1A, including Dravet syndrome, which are often refractory to conventional antiepileptic medications but can respond to a ketogenic diet (KD) (Korff et al., J Child Neurol 2007, 22:185). SCN1A mutant mice also respond to KD (Dutton et al., Epilepsia 2011, 52:2050). Studies were undertaken to determine whether KD could reduce epileptiform spikes and thereby improve cognition in a mouse model of Alzheimer's disease.

Ketogenic diet, but not fasting, consistently reduced epileptiform spikes in the APPJ20 Alzheimer's mouse model. This reduction in spikes was independent or downstream of inhibitory interneuron function. The effect on spike reduction was sustained through several months of treatment. Long-term treatment resulted in cognitive improvement in the water maze and in habituation to the open field, and in the more severely affected male APPJ20 mice also improved survival. Finally, treatment with compounds described herein that are metabolized to the ketone body β-hydroxybutyrate immediately reduced epileptiform spikes to a similar degree as ketogenic diet. Agents that increase blood levels of β-hydroxybutyrate or act on downstream targets of β-hydroxybutyrate are provided herein in the treatment of Alzheimer's disease through improving network function and ameliorating epileptiform activity.

Example 10—Pilot Feeding Study Using Food Supplemented with C6 Ester of β-hydroxybutyrate Materials and Methods C6 monoester of β-hydroxybutyrate was synthesized as described above and purified for testing in mice. The C6 monoester of β-hydroxybutyrate was mixed into ground control food (10% calories from protein), the same control diet used in the above examples involving ketogenic and control diet. The food was placed in a glass jar inside the animal cage at the start of the nighttime feeding cycle, 19:00 h. Different concentrations of the C6 monoester of β-hydroxybutyrate (w/w) were mixed into the control diet to determine which concentration was sufficient to raise BHB levels in the mice. n=4 mice/condition (2 mice per cage). All mice were 12 month-old C57BL/6 males.

Results

Figure 11:
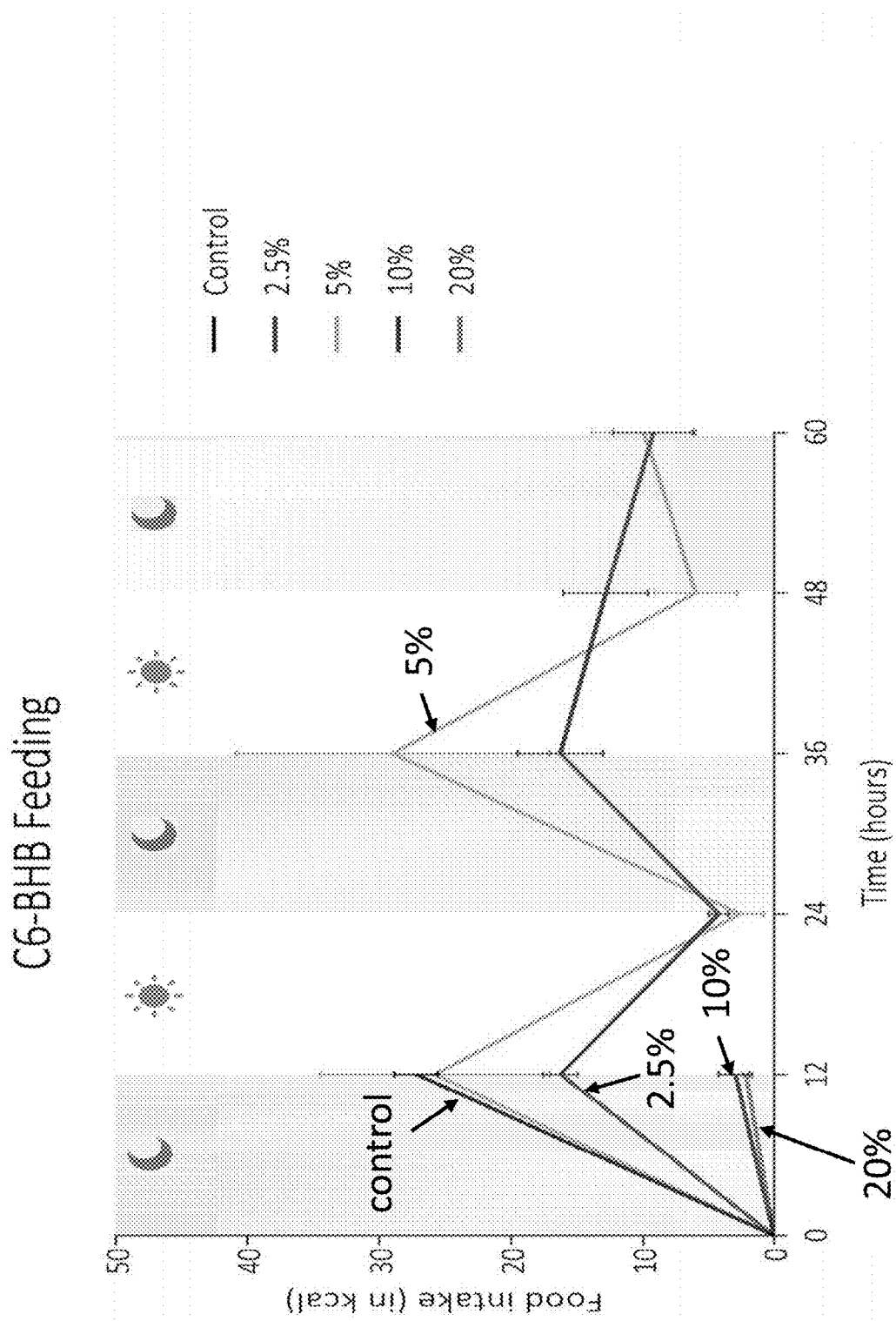
FIG. 11 depicts intake over time of food containing different concentrations of C6 esters of β-hydroxybutyrate.

FIG. 11 depicts intake over time of food containing different concentrations of C6 esters of β-hydroxybutyrate. Food containing 10% and 20% by weight C6 monoester of β-hydroxybutyrate was observed to be less palatable to the mice and was ingested at a lower rate. Incorporating 5% by weight of the C6 monoester of β-hydroxybutyrate did not change the amount of food consumed by mice over the first 12 hours relative to control.

Figure 12:
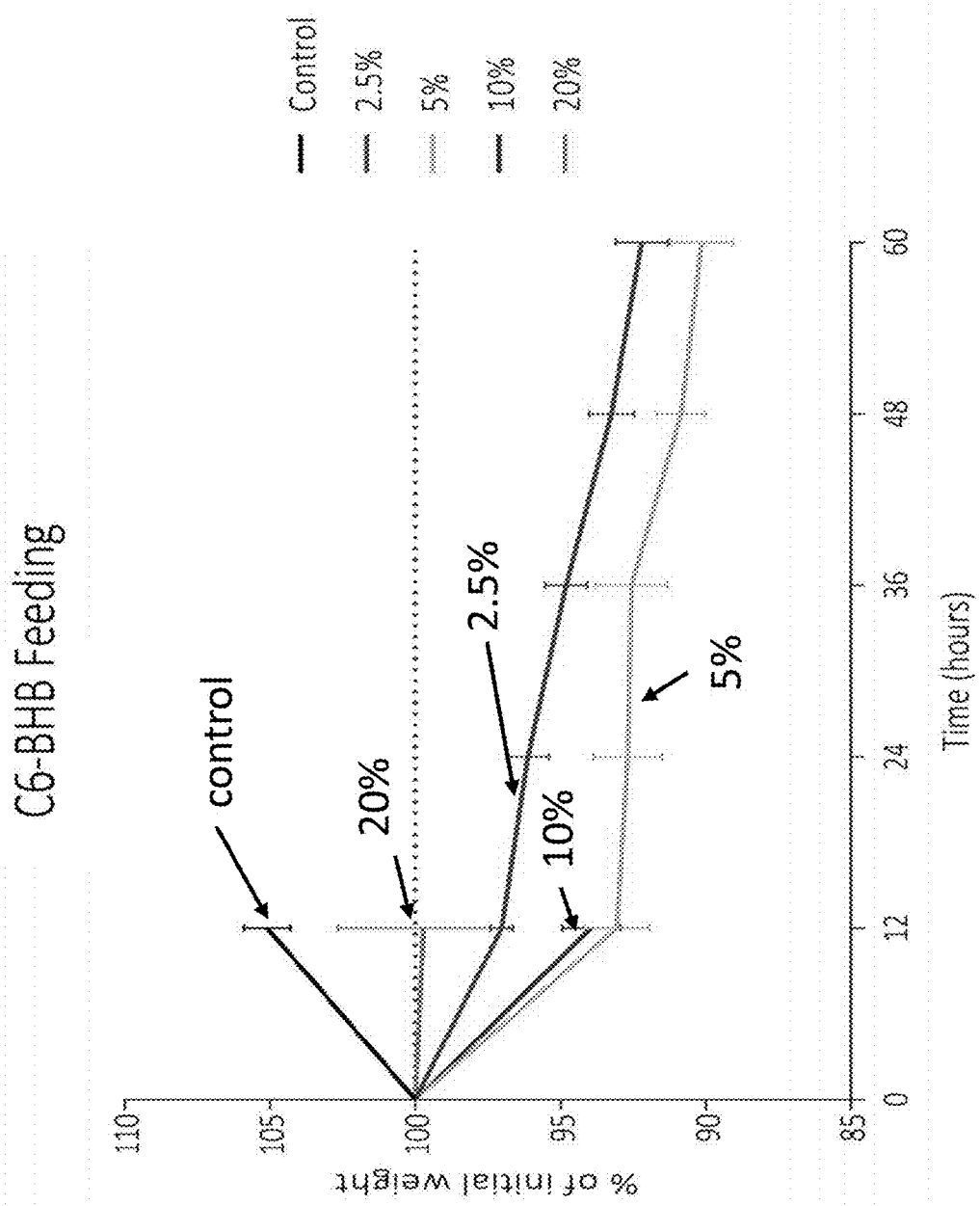
FIG. 12 depicts weight loss by mice over time after ingesting food containing different amounts of C6 esters of β-hydroxybutyrate.

FIG. 12 depicts weight loss by the mice over time while fed a diet containing different amounts of the C6 monoester of β-hydroxybutyrate. The weight loss exhibited by mice fed a diet containing 2.5% and 5% by weight of the C6 esters of β-hydroxybutyrate was not attributed to fasting as a normal amount of food was ingested by the mice over the course of the study.

Figure 13:
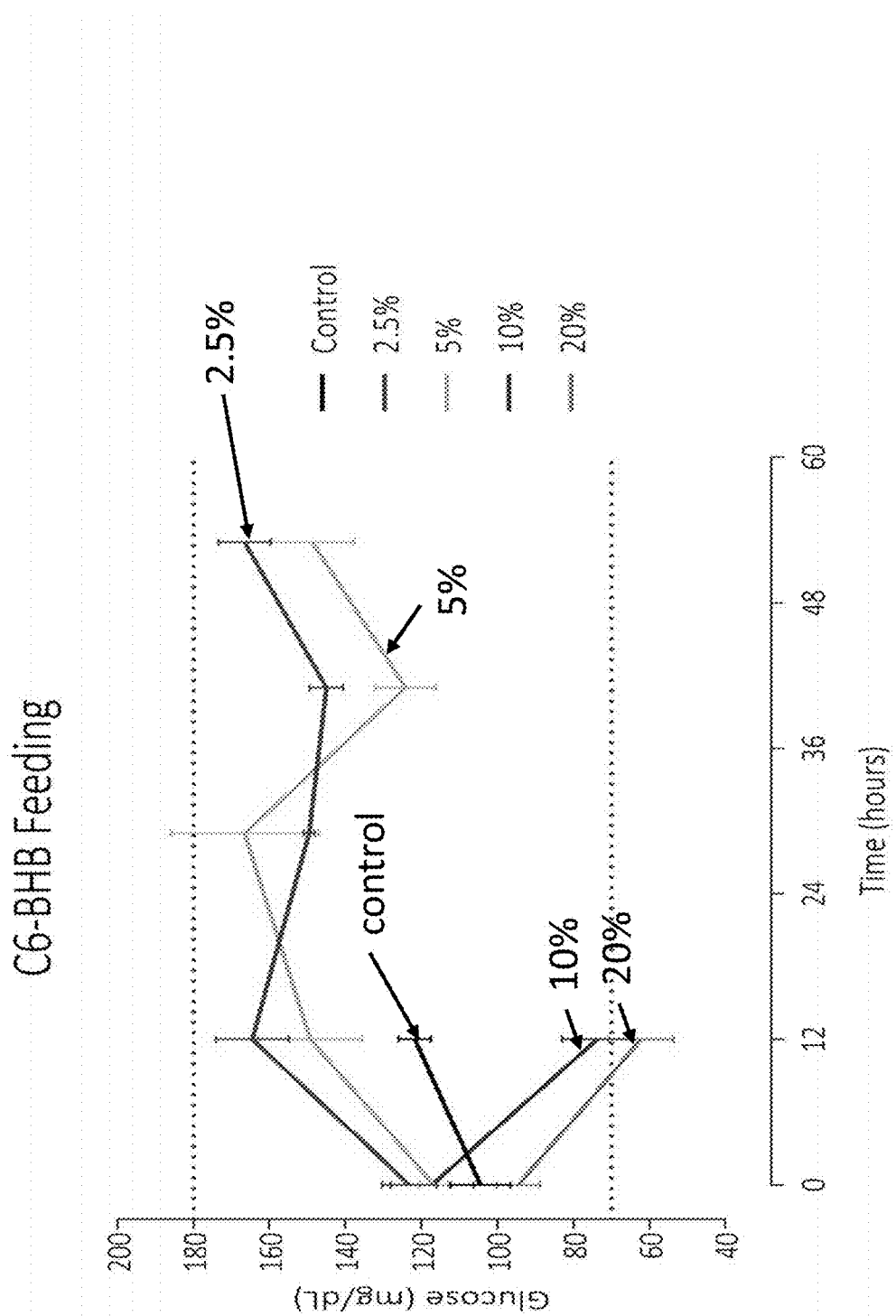
FIG. 13 depicts the blood glucose levels of mice over time while feeding with food containing different amounts of C6 esters of β-hydroxybutyrate.

FIG. 13 depicts the blood glucose levels of the mice during the course of the feeding study. Mice ingesting the control food composition and those ingesting food with different amounts of the C6 monoester of β-hydroxybutyrate exhibited blood glucose levels within the normal range of glycaemia (min.=70 mg/dL; max=180 mg/dL). Mice ingesting food having 10% and 20% by weight of the C6 monoester of β-hydroxybutyrate exhibited decreasing blood glucose over the first 12 hours. Observations indicated that these mice consumed little food having 10% and 20% by weight of the C6 monoester of β-hydroxybutyrate during the first 12 hours. Without intending to be bound by any particular theory, it is believed that this fasting resulted in the decrease in blood glucose for these conditions.

Figure 14:
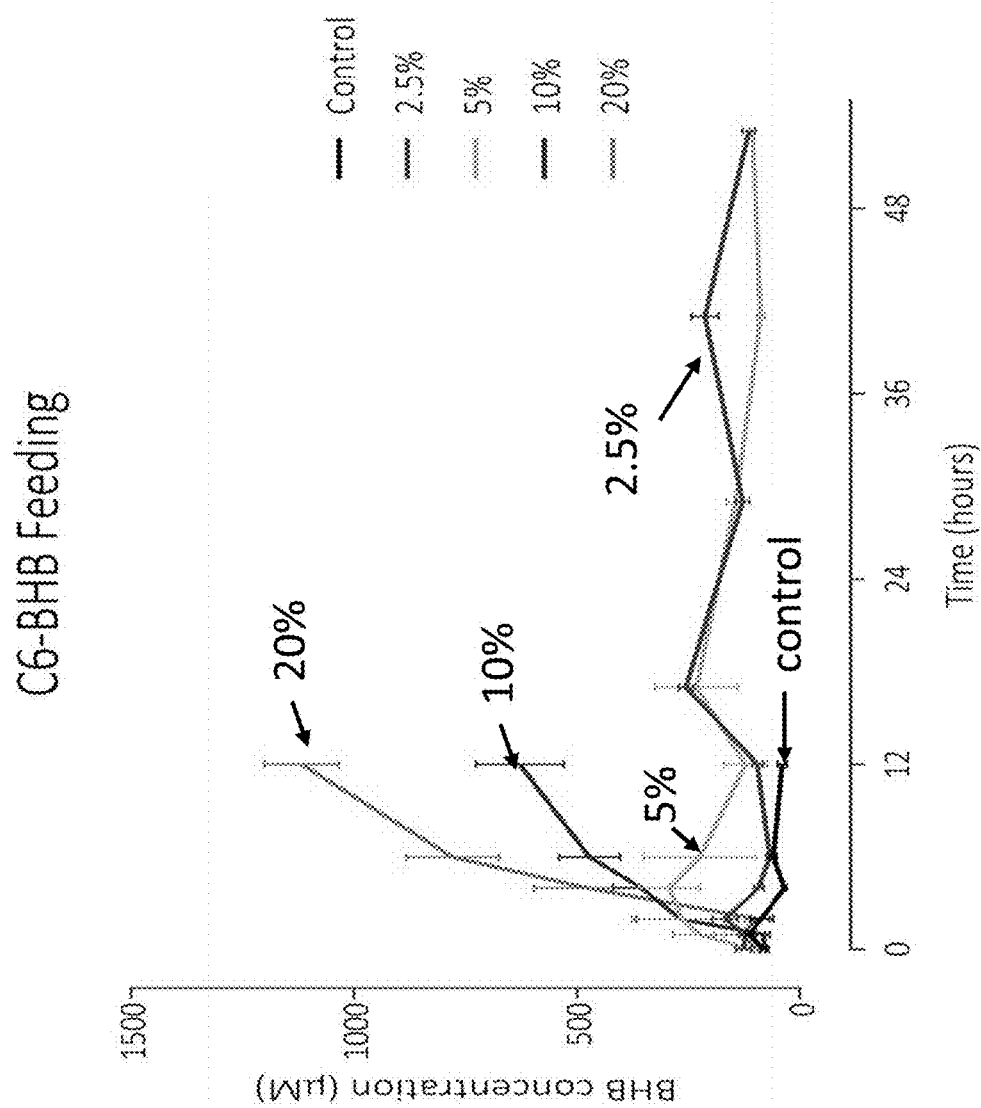
FIG. 14 depicts blood concentration of β-hydroxybutyrate over time after feeding mice with food having different amount of C6 esters of β-hydroxybutyrate.

FIG. 14 depicts the blood concentration of β-hydroxybutyrate over time after feeding the mice with food having different amounts of the C6 monoester of β-hydroxybutyrate. A diet containing 2.5% by weight or 5% by weight of the C6 monoester of β-hydroxybutyrate resulted in a slight increase in BHB level in the blood, but was insufficient to provide a level greater than the targeted 500 μM threshold. Mice fed a diet including 10% or 20% by weight of the C6 monoester of β-hydroxybutyrate exhibited a greater increase in β-hydroxybutyrate concentration. However, without intending to be bound by any particular theory, it is believed that this increase in BHB level was likely not a result of the higher concentration of the C6 monoester of β-hydroxybutyrate in the diet, since the mice ate very little of the food. Rather, this increase is probably explained by the mice fasting.

Example 11—Pilot Feeding Study Using Food Supplemented with Esters of β-hydroxybutyrate and Butanediol Materials and Methods Different esters of β-hydroxybutyrate and butanediol were synthesized as described above and purified for testing in mice. The esters of β-hydroxybutyrate and butanediol that were supplemented into the diet of the mice in this study were as follows: 1) C8 diesters of butanediol (C8x2-BD); 2) C8 monoesters of β-hydroxybutyrate (C8-BHB); 3) C6 diesters of β-hydroxybutyrate (C6x2-BHB); 4) C6 monoesters of β-hydroxybutyrate (C6-BHB); and 5) C6 diesters of butanediol (C6x2-BD). Food compositions supplemented with 1,3-butanediol were also tested. Compounds were mixed at 10% w/w in ground normal chow (20% calories from protein) to match standard vivarium feed. The food was provided in a glass jar inside the animal cage. n=2 mice/condition, 18 mice total. All mice were 12 month-old C57BL/6 males. Mice were placed in individual cages to record food intake more precisely. Food was switched back to normal chow at 72 hrs (ground and in a glass jar).

Results

Figure 15:
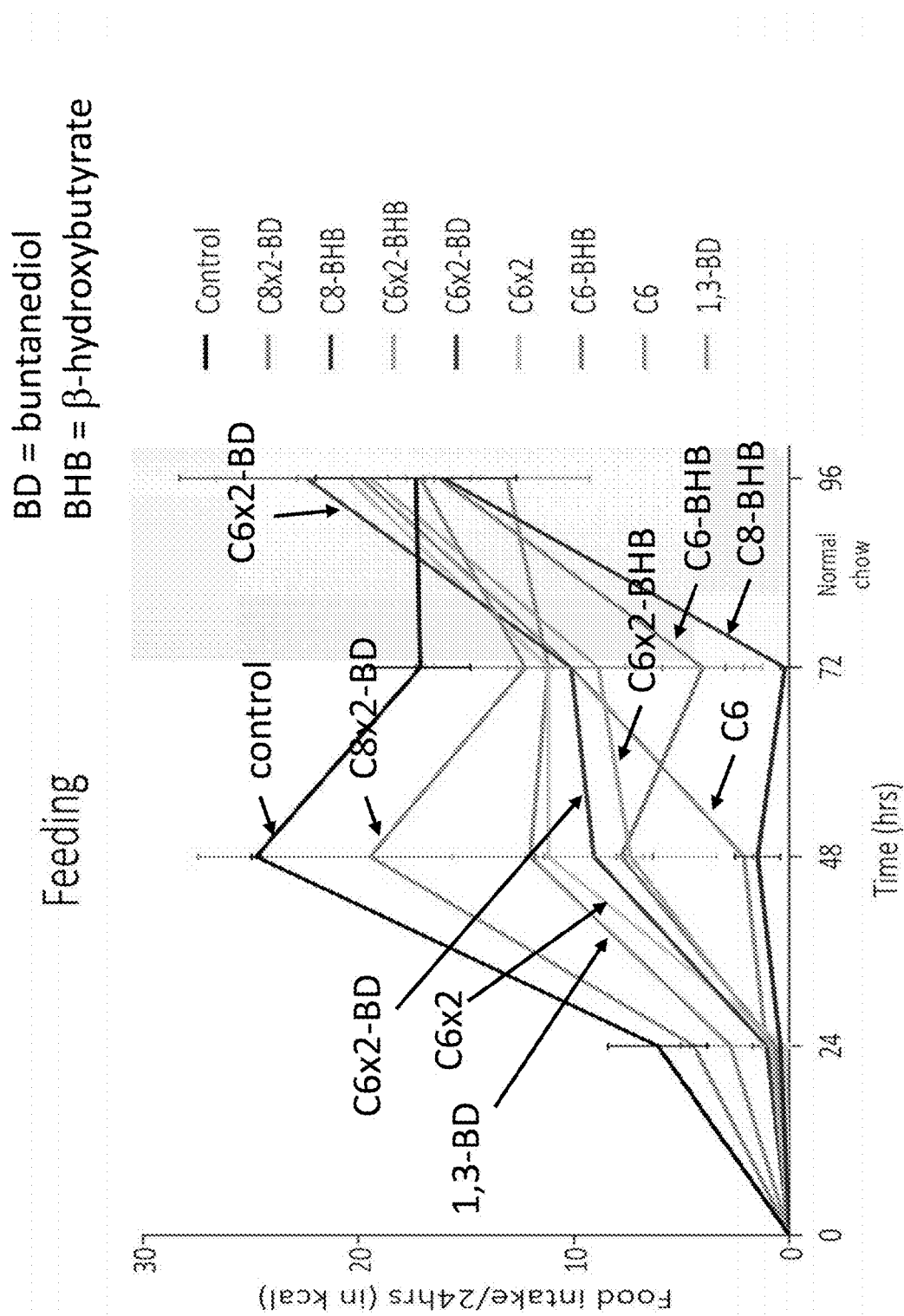
FIG. 15 depicts intake over time of food containing the different esters of butanediol and β-hydroxybutyrate.

FIG. 15 depicts intake over time of food containing the above-listed esters of butanediol and esters of β-hydroxybutyrate. The control was a normal chow diet without supplement. Food supplemented with 1,3-butanediol, a 6-carbon fatty acid ester-linked to a 2-carbon alkyl group (C6) which served as a control to the C6 monoester of β-hydroxybutyrate and a 6-carbon fatty acid ester-linked to a 6-carbon alkyl group (C6x2) which served as a control to the C6 diester of β-hydroxybutyrate was also tested.

Depending on the compound, the mice needed 2 to 4 days to adapt to the taste/smell of the supplemented chow and start eating normal amounts.

Figure 16:
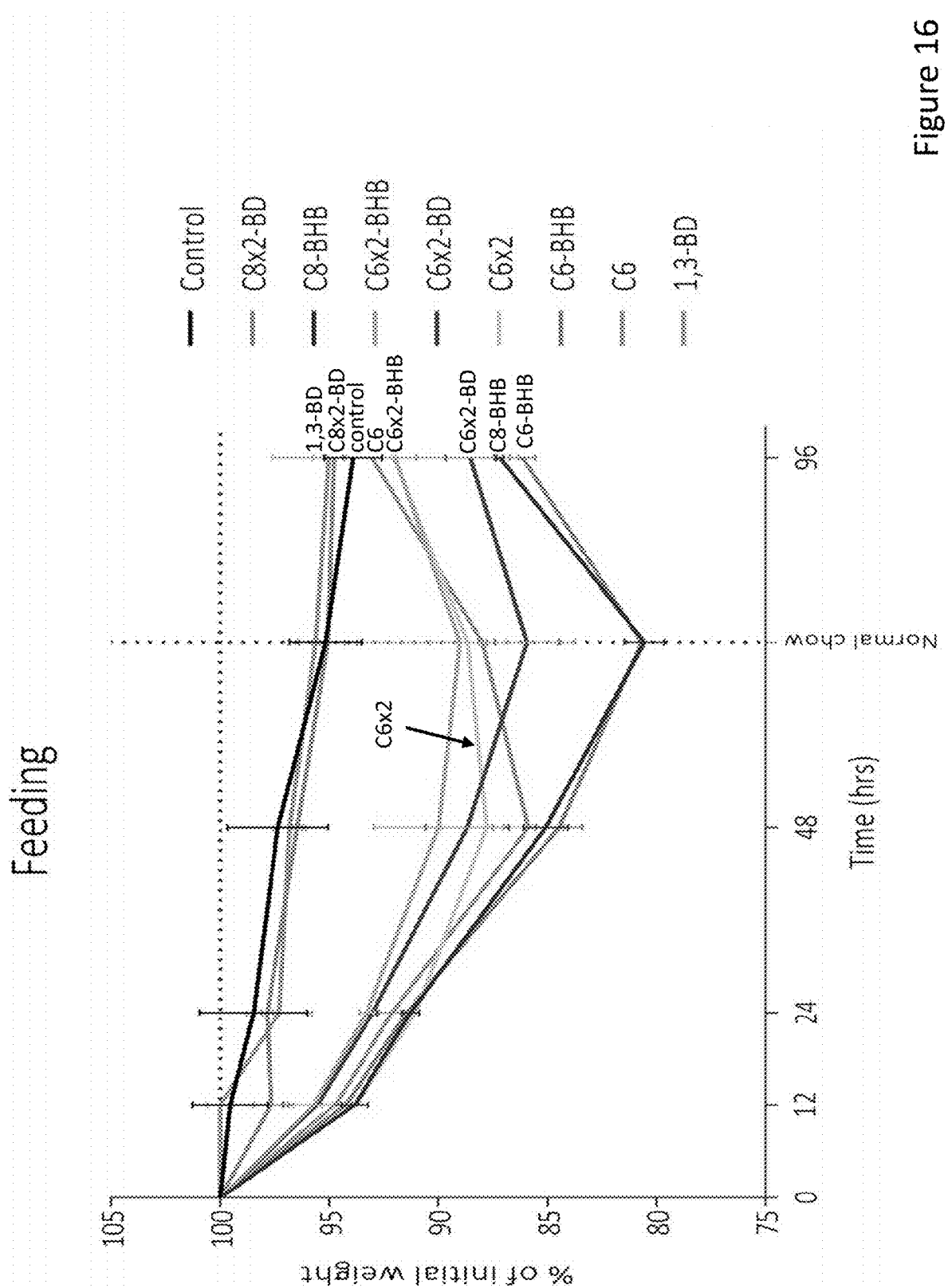
FIG. 16 depicts the change in weight by mice over time when fed food compositions supplemented with the different esters of butanediol and β-hydroxybutyrate.

FIG. 16 depicts weight loss in the mice over time when fed food compositions supplemented with the different esters of butanediol and β-hydroxybutyrate. The results show a clear distinction between compounds causing significant weight loss and those causing weight loss similar to control. Mice fed a diet supplemented with C8 diesters of butanediol lost approximately the same amount of weight as those consuming the control food composition, whereas mice consuming C6 diesters of β-hydroxybutyrate, C6 diesters of butanediol, C8 monoesters of β-hydroxybutyrate, and C6 monoesters of β-hydroxybutyrate exhibited significant weight loss. Without intending to be bound by any particular theory, it is believed that these results are not solely explained by differences in food intake (e.g., food intake of C6x2-BD was normal, but weight loss still resulted). Without intending to be bound by any particular theory, it is believed that the weight loss of the control mice can be explained by lower food intake at the beginning of the experiment while adapting to the texture and placement of ground food, and higher heat loss resulting from the use of individual cages.

Figure 17:
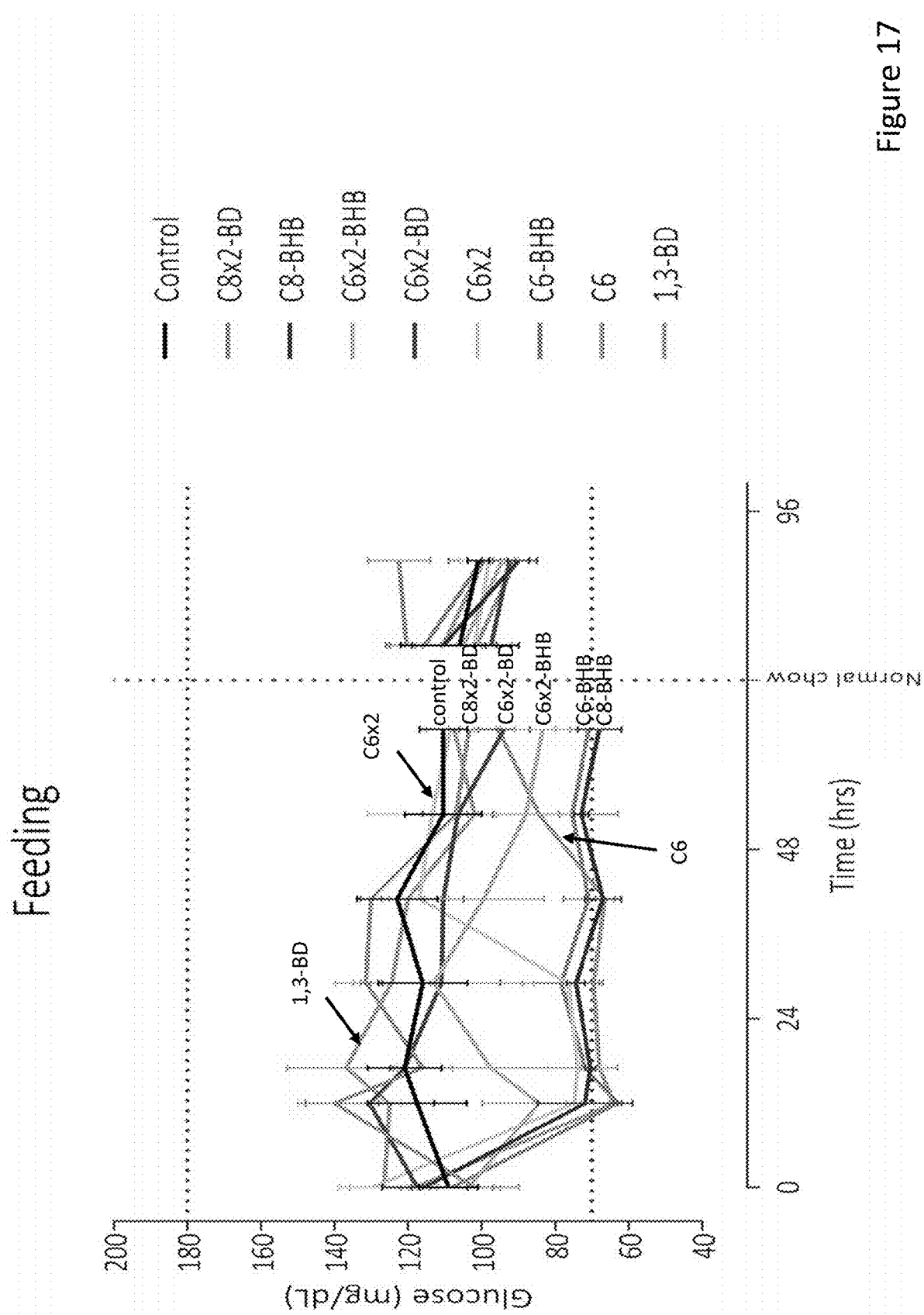
FIG. 17 depicts the blood glucose levels of mice over time while feeding with food supplemented with different esters of butanediol and β-hydroxybutyrate.

FIG. 17 depicts the blood glucose levels of the mice during the course of the feeding study. Mice ingesting the control food composition and those ingesting food containing the different types of esters of butanediol and β-hydroxybutyrate exhibited blood glucose levels with the normal range of glycaemia (min.=70 mg/dL; max=180 mg/dL).

Some of the exhibited hypoglycaemias can be explained by fasting (C8-BHB) and C6), but others (C6-BHB) are likely a result of the compound. No sedation was observed.

Figure 18:
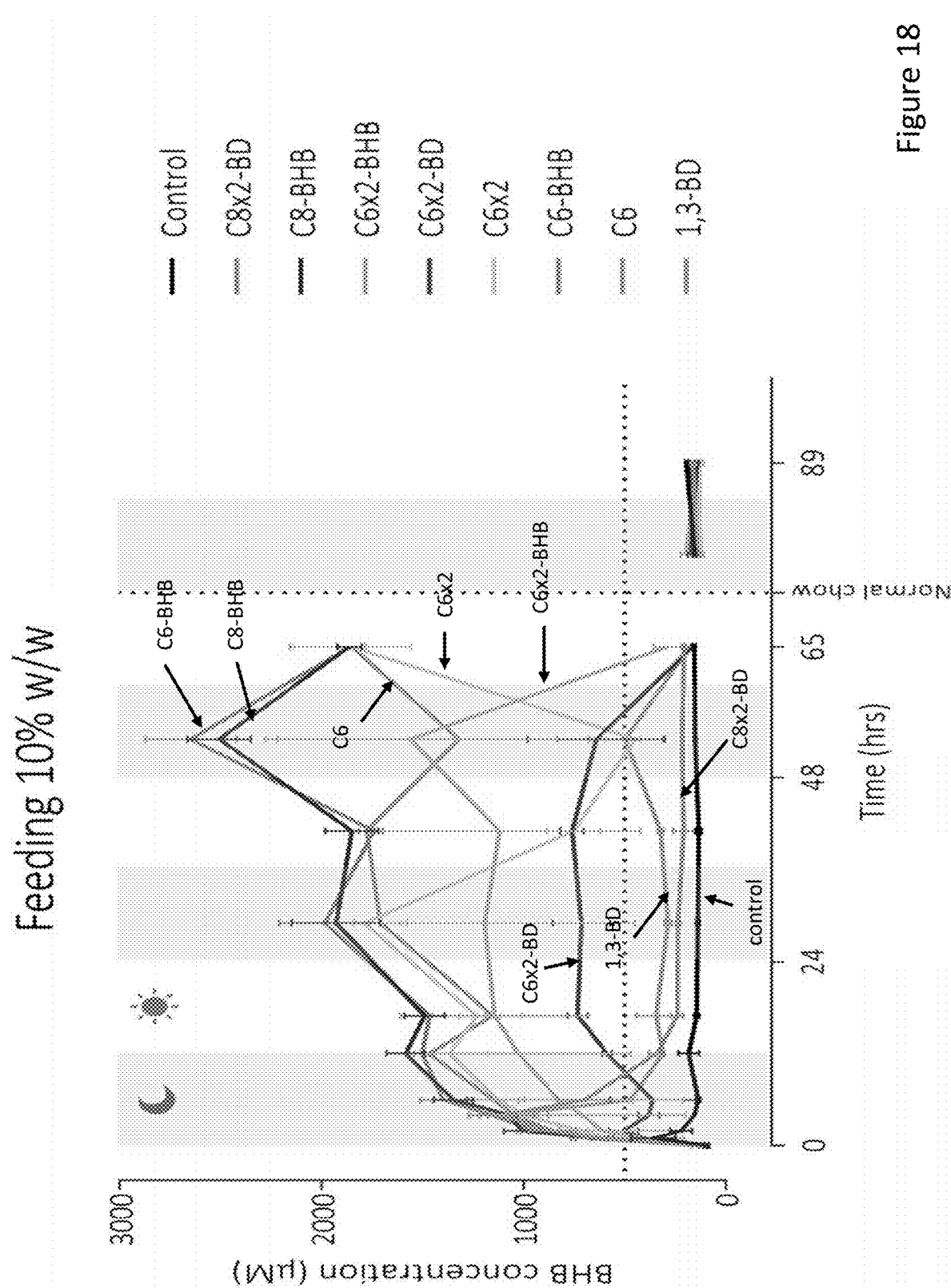
FIG. 18 depicts the blood concentration of β-hydroxybutyrate over time after feeding mice with food containing different esters of butanediol and β-hydroxybutyrate.

FIG. 18 depicts the blood concentration of β-hydroxybutyrate over time after feeding the mice with food containing the different esters of butanediol and β-hydroxybutyrate. The horizontal dotted line shows the targeted 500 μM threshold. In interpreting the results, the fasting effect should be taken into account. For example, the high BHB value for C8-BHB is likely a result of fasting rather than a result of the compound itself. A day/night pattern also becomes apparent after 48 hours, with high BHB during the nighttime feeding period, and lower BHB during the day. Without intending to be bound by any particular theory, it is believed this diurnal pattern is consistent with the ingested compounds being converted in the body to BHB during the feeding period.

Example 12—Mice Feeding Study of Food Supplemented with C6 Diesters of β-hydroxybutyrate Materials and Methods Based on the results of the above Pilot studies, the C6 diesters of β-hydroxybutyrate were selected for a longer study with a greater number of mice to see if it would remain ketogenic even after food intake normalized. C6 diesters of β-hydroxybutyrate were synthesized as described above and purified for testing in mice. The C6 diesters of β-hydroxybutyrate were mixed at 10% w/w into ground standard chow diet (20% calories from protein), which was re-formed into pellets. Re-pelleted food was used to minimize any variable effects from a change in diet texture to ground.

The pelleted food was consumed by the mice after being placed in a glass jar in the animal cage. Four mice per diet were tested, with the mice individually caged. All mice were 12 month-old C57BL/6 males. Daily weight and caloric intake was monitored and blood was drawn for glucose and β-hydroxybutyrate levels on the eighth night. Mice fed with food supplemented with C6 esters of β-hydroxybutyrate initially ate less food and lost weight. By the 7$^{th}$ night, the weights of the mice stabilized and 24 hour caloric intake was similar between the control diet and the mice that consumed food supplemented with C6 esters of β-hydroxybutyrate. On the eighth night, both groups of mice consumed similar calories in the four hours between the start of the natural feeding time at 19:00 h and the time that blood was drawn starting at 23:00 h.

Results

Figure 19:
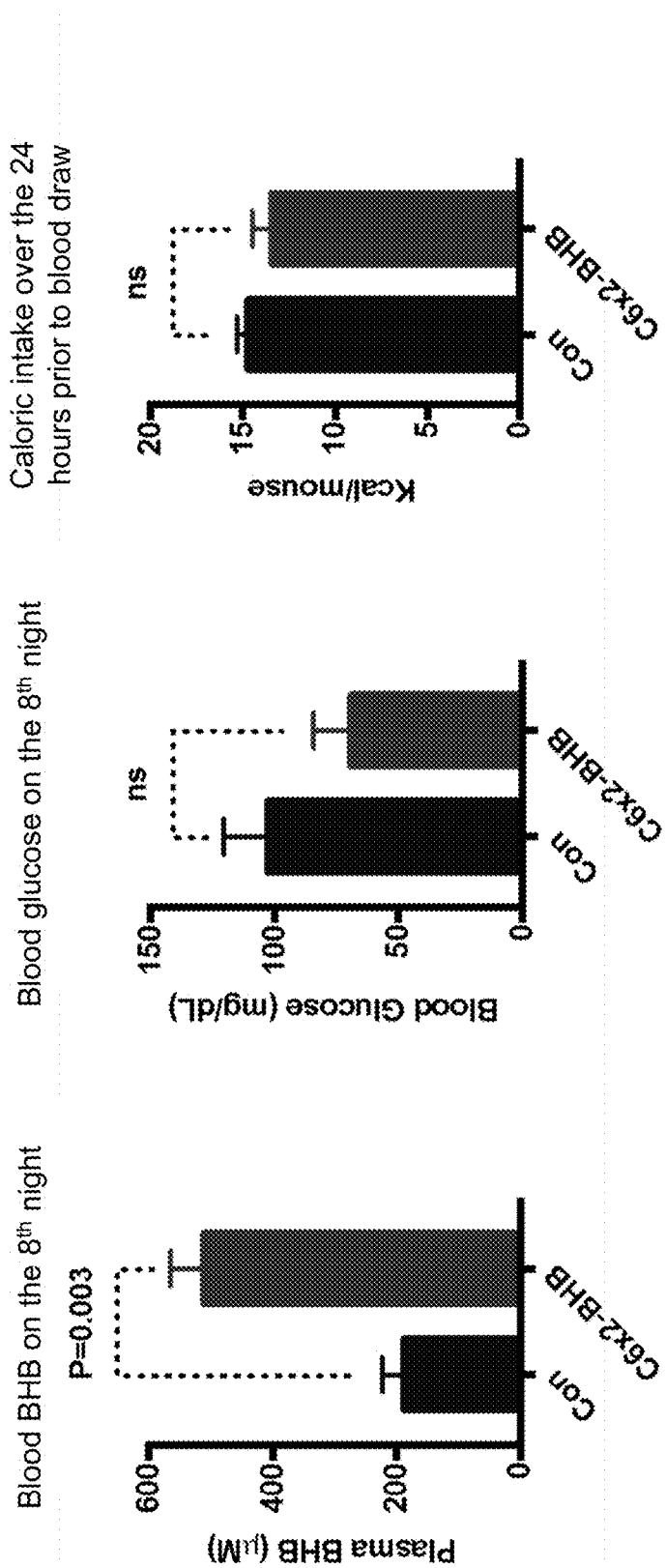
FIG. 19 depicts a comparison of the plasma β-hydroxybutyrate, blood glucose and caloric intake of mice that consumed the control food and mice that consumed food supplemented with C6 esters of β-hydroxybutyrate.

FIG. 19 depicts a comparison of the plasma β-hydroxybutyrate, blood glucose and caloric intake of mice fed the control diet and mice fed a diet supplemented with 10% w/w C6 diesters of β-hydroxybutyrate. The mice fed the diet supplemented with C6 diesters of β-hydroxybutyrate exhibited greater β-hydroxybutyrate plasma concentrations, even as part of a normal diet with normal caloric intake, and reached the targeted 500 μM threshold.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of reducing epileptiform activity in the brain of a subject and/or treating in said subject one or more conditions selected from the group consisting of Alzheimer's disease, epilepsy, Parkinson's disease, heart failure, traumatic brain injury, stroke, hemorrhagic shock, acute lung injury after fluid resuscitation, acute kidney injury, myocardial infarction, myocardial ischemia, diabetes, glioblastoma multiforme, diabetic neuropathy, prostate cancer, amyotrophic lateral sclerosis, Huntington's disease, cutaneous T cell lymphoma, multiple myeloma, peripheral T cell lymphoma, HIV, and Niemann-Pick Type C disease said method comprising:

administering to said subject, a therapeutically effective amount of a compound of the Formula:

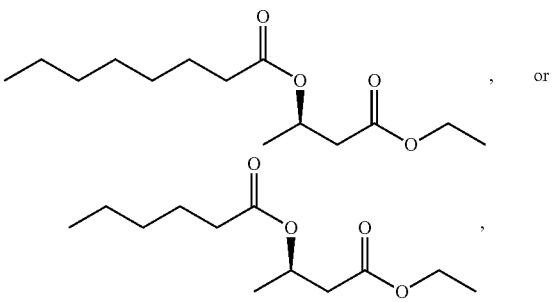

or a compound of Formula II:

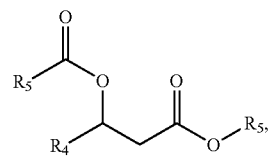

or salts, solvates or hydrates thereof, wherein:

$R_4$ is H or C(1-6) alkyl or substituted alkyl; and $R_5$ and $R_6$ are independently unsubstituted or substituted straight chain C(4-30) alky.

2. The method of claim 1, wherein the therapeutically effective amount is sufficient to reduce epileptiform activity in the brain of the subject.

3. The method of claim 2, wherein said method comprises a method of reducing epileptiform activity in the brain of the subject.

4. The method of claim 1, wherein said compound comprises a compound of Formula II.

5. The method of claim 4, wherein R4 is an unsubstituted C(1-6) alkyl.

6. The method of claim 5, wherein R4 is methyl.

7. The method of claim 4, wherein R5 and R6 are independently unsubstituted C(6-18) alkyl.

8. The method of claim 4, wherein $R_5$ and $R_6$ are independently unsubstituted C6 alkyl or independently unsubstituted C8 alkyl.

9. The method of claim 4, wherein said compound is compound of Formula IIa:

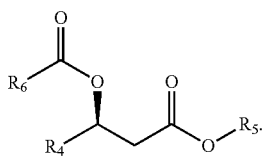

Formula IIa

10. The method of claim 4, wherein said compound is a compound of Formula IIb:

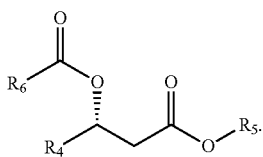

Formula IIb

11. The method of claim 4, wherein said compound is compound having the formula:

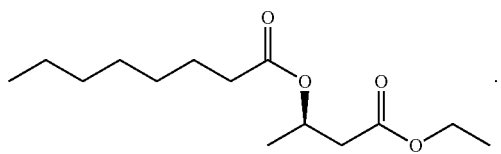 [SMILES: CCCCCCCC(=O)O[C@H](C)CC(=O)OCC]

12. The method of claim 1, wherein said compound is compound having the formula:

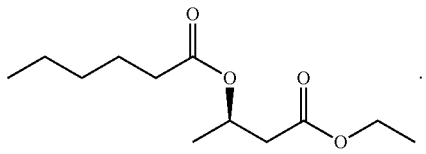 [SMILES: CCCCCC(=O)O[C@H](C)CC(=O)OCC]

13. The method of claim 1, wherein said compound is compound having the formula:

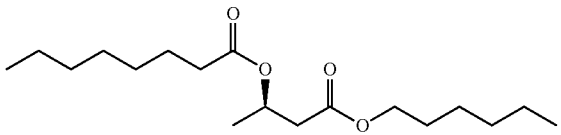

14. The method of claim 1, wherein said compound is compound having the formula:

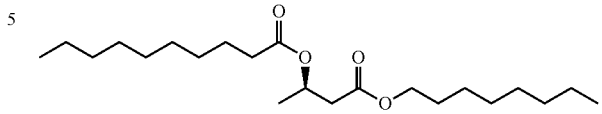

15. The method of claim 1, wherein said compound is compound having the formula:

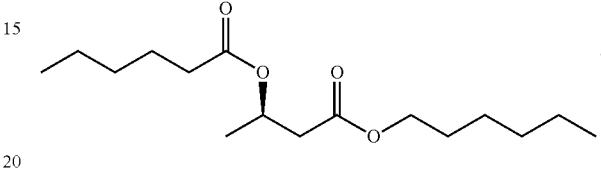

16. The method of claim 1, wherein said compound is administered as an oral preparation.

17. The method of claim 16, wherein said oral preparation comprises a preservative and/or a flavoring agent.

18. The method of claim 17, wherein said oral preparation comprises water.

19. The method of claim 18, wherein said oral preparation comprises a syrup or an elixir.

20. The method of claim 18, wherein said oral preparation comprises a suspension.

21. The method of claim 17, wherein said oral preparation comprises a binder.

22. The method of claim 21, wherein said oral preparation comprises a binder selected from the group consisting of cellulose, methylcellulose, hydroxymethylcellulose, polypropylpyrrolidone, polyvinylpyrrolidone, gelatin, gum arabic, poly(ethylene glycol), sucrose, and starch.

23. The method of claim 17, wherein said oral preparation comprises a flavoring agent.

24. The method of claim 23, wherein said oral preparation comprises a flavoring agent selected from the group consisting of citric acid, menthol, glycine, and orange powder.

25. The method of claim 17, wherein said oral preparation comprises a preservative.

26. The method of claim 25, wherein said oral preparation comprises a preservative selected from the group consisting of sodium benzoate, sodium bisulfate, methylparaben, and propylparaben.

27. The method of claim 1, wherein compound is administered as a food supplemented with said compound(s).

28. The method of claim 27, wherein said food comprises one or more additional components of a ketogenic diet.

* * * * *